(12) United States Patent
Ye

(10) Patent No.: US 11,844,846 B2
(45) Date of Patent: Dec. 19, 2023

(54) STYRYLBENZOTHIAZOLE DERIVATIVES AND USES IN IMAGING METHODS

(71) Applicant: Emory University, Atlanta, GA (US)

(72) Inventor: Keqiang Ye, Lilburn, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 204 days.

(21) Appl. No.: 17/055,935

(22) PCT Filed: May 16, 2019

(86) PCT No.: PCT/US2019/032592
§ 371 (c)(1),
(2) Date: Nov. 16, 2020

(87) PCT Pub. No.: WO2019/222454
PCT Pub. Date: Nov. 21, 2019

(65) Prior Publication Data
US 2021/0260224 A1    Aug. 26, 2021

Related U.S. Application Data

(60) Provisional application No. 62/725,615, filed on Aug. 31, 2018, provisional application No. 62/672,230, filed on May 16, 2018.

(51) Int. Cl.
*A61K 51/04* (2006.01)
*C07B 59/00* (2006.01)

(52) U.S. Cl.
CPC ........ *A61K 51/0453* (2013.01); *C07B 59/002* (2013.01)

(58) Field of Classification Search
CPC .......................... A61K 51/0453; C07B 59/002
USPC ....................................................... 424/1.89
See application file for complete search history.

(56) References Cited

U.S. PATENT DOCUMENTS

| | | | |
|---|---|---|---|
| 8,163,928 B2 | 4/2012 | Gravenfors et al. | |
| 8,641,903 B2 | 2/2014 | Voccia et al. | |
| 2005/0260126 A1* | 11/2005 | Kudo ................... | C07D 417/06 424/1.11 |
| 2007/0031328 A1* | 2/2007 | Kung .................... | C07C 213/08 424/1.11 |
| 2012/0214994 A1* | 8/2012 | Chi ....................... | C07D 471/04 546/281.1 |
| 2015/0258175 A1 | 9/2015 | Yu et al. | |
| 2015/0366776 A1 | 12/2015 | Chung et al. | |

FOREIGN PATENT DOCUMENTS

| | | |
|---|---|---|
| CN | 101410393 A | 4/2009 |
| CN | 102300589 A | 12/2011 |
| WO | 2002074347 | 9/2002 |
| WO | 2003006070 | 1/2003 |
| WO | 2004035522 | 4/2004 |
| WO | 2004075882 | 9/2004 |
| WO | 2004100998 | 11/2004 |
| WO | 2005013889 | 2/2005 |
| WO | 2005088308 | 9/2005 |
| WO | 2006008496 | 1/2006 |
| WO | 2010063701 | 6/2010 |
| WO | 2015051188 | 4/2015 |

OTHER PUBLICATIONS

Filho et al. New J. Chem. 2017, 41, 13760-13772. (Year: 2017).*
Ferriz et al. Curr. Pharmaceutical Des. 2010, 16, 1033-2052. (Year: 2010).*
Morais et al. Bioorg. Med. Chem. 2011, 19, 7698-7710. (Year: 2011).*
Bolton, "Radiohalogen Incorporation Into Organic Systems", J. Lab. Comp. Radiopharm., 2002, vol. 45, No. 2, pp. 485-528.
Braak et al., Idiopathic Parkinson's Disease: Possible Routes by Which Vulnerable Neuronal Types May Be Subject to Neuroinvasion by an Unknown Pathogen, J. Neural Transm. 2003; vol. 110, No. 5, pp. 517-536.
Brooks, Positron Emission Tomography and Single-Photon Emission Computed Tomography in Central Nervous System Drug Development, NeuroRx 2005, 2(2), 226-236.
Brundin et al., How Strong is the Evidence that Parkinson's Disease is a Prion Disorder, Current Opinion in Neurology, vol. 29, No. 4, Aug. 1, 2016, pp. 459-466.
Chinese Patent Application No. 2019800317559, "Office Action" dated Jun. 24, 2022, 10 pages with English translation.
Cohen et al., Using Pittsburgh Compound B for in Vivo PET Imaging of Fibrillar Amyloid-Beta, Advances in pharmacology, vol. 64, 2012, pp. 27-81.
Crouzel et al., (1987) Recommendations for a practical production of [11C]methyl iodide Appl. Radiat. Isot. Int. J. Appl. Instrum. Part A 38, 601-603.
Da Silva et al., Efficient Enzymatic Preparation of 13N-Labelled Amino Acids: Towards Multipurpose Synthetic Systems, Chem. Eur. J. 2016, 22, 13619.
European Application No. 19803324.3, Extended European Search Report dated Dec. 13, 2021, 16 pages.
Goodman et al., Synthesis and characterization of iodine-123 labeled 2beta-carbomethoxy-3beta-(4'-((Z)-2-iodoethenyl)phenyl)nortropane. J Med Chem, 2003, 46(6):925-35.
International Application No. PCT/US2019/032592, International Preliminary Report on Patentability dated Nov. 26, 2020, 9 pages.
International Application No. PCT/US2019/032592, International Search Report and Written Opinion dated Jul. 3, 2019, 10 pages.
Jewett et al., (1992) A Simple Synthesis of [11C]Methyl Triflate Appl. Radiat. Isot. 43, 1383-1385.

(Continued)

*Primary Examiner* — Michael G. Hartley
*Assistant Examiner* — Sean R Donohue
(74) *Attorney, Agent, or Firm* — Kilpatrick Townsend & Stockton, LLP

(57) ABSTRACT

This disclosure relates to styrylbenzothiazole derivatives for use as in vivo imaging agents for the diagnosis of Parkinson's disease (PD) or other degenerative disorders or conditions of the central nervous system. Early diagnosis is particularly advantageous as neuroprotective treatment can be applied to healthy neural cells to delay or even prevent the onset of debilitating clinical symptoms.

8 Claims, 17 Drawing Sheets

(56) References Cited

OTHER PUBLICATIONS

Jewett et al., (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York.

Kabalaka et al., Synthesis of radioiodinated aryl iodides via boronate precursors. Nucl Med Biol. Nov. 2002;29(8):841-3.

Kabalaka et al., A facile synthesis of radioiodinated (Z)-vinyl iodides via vinylboronates. Nucl Med Biol. May 2003:30(4):369-72.

Kabalaka et al., A Facile No-Carrier-Added Radioiodination Procedure Suitable for Radiolabeling Kits, Nucl.Med.Biol. 2004; vol. 31, No. 7, pp. 935-938.

Klunk et al., Imaging Brain Amyloid in Alzheimer's Disease with Pittsburgh Compound-B, Ann. Neurol. 2004, vol. 55, No. 3, pp. 306-319.

Kotzbauer, et al. Current Status of the Development of PET Radiotracers for Imaging Alpha Synuclein Aggregates in Lewy Bodies and Lewy Neurites, Clinical and Translational Imaging, 2017, vol. 5, pp. 3-14.

Li et al., Synthesis of structurally identical fluorine-18 and iodine isotope labeling compounds for comparative imaging. Bioconjug Chem, 2003, 14(2):287-94.

Marazano, et al., Synthesis of methyl iodide-11C and formaldehyde-11C Appl. Radiat. Isot. 28, 1977, pp. 49-52.

Maziere et al., 76Br-beta-CBT, a PET tracer for investigating dopamine neuronal uptake. Nucl Med Biol, 1995, 22(8):993-7.

Masuda et al., Small Molecule Inhibitors of α-Synuclein Filament Assembly, Biochemistry; vol. 45, No. 19, 2006, pp. 6085-6094.

Mathis et al., Synthesis and Evaluation of 11c-labeled 6-substituted 2-arylbenzothiazoles as Amyloid Imaging Agents, J Med Chem, vol. 46, No. 13, 2003, pp. 2740-2754.

Plisson et al., Synthesis and in vivo evaluation of fluorine-18 and iodine-123 labeled 2beta-carbo(1-fluorethoxxy)-3beta-(4'-((Z)-2 iodoethenyl)phenyl)nortropane as a candidate serotonin transporter imaging agent, J Med Chem. 2007, 50(19):4553-60.

Plisson et al., Synthesis, radiosynthesis, and biological evaluation of carbon-11 and iodine-123 labeled 2beta-carbomethoxy-3beta-[4'-((Z)-2-haloethenyl)phenyl]tropanes. J Med Chem, 2004, 47(5):1122-35.

Safriel et al., MR Spectroscopy in the Diagnosis of Cerebral Amyloid Angiopathy Presenting as a Brain Tumor, American Journal of Neuroradiology, vol. 25, No. 10, Dec. 31, 2004, pp. 1705-1708.

Serdons et al., 6-Methoxy-2-(4'-[18F]fluorophenyl)-1,3-benzothiazole and 6-methyl-2-(4'-[18F]fluorophenyl)-1,3-benzothiazole as potential amyloid imaging agents, . Nuc. Med.; 47(Suppl.I): 31P) 2006 (Abstract).

Spillantini et al., α-Synuclein in Lewy Bodies, Nature, vol. 388, 1997, pp. 839-840.

Volpicelli-Daley et al., (2014) Addition of exogenous α-Synuclein Pre-formed fibrils to Primary Neuronal Cultures to seed recruitment of endogenous α-Synuclein to Lewy body and Lewy Neurite-like aggregates, Nat. Protoc., vol. 9, No. 9, pp. 2135-2146.

Watkins et al., (1988) A Captive Solvent Method for Rapid N-[11C]Methylation of Secondary Amides Application to the Benzodiazepine, 4'-Chlorodiazepam (RO5-4864) Appl. Radiat. Isot. 39, 441-444.

Wilson et al., (1996) In vivo evaluation of [11C] and [15F]-labeled cocaine analogues as potential dopamine transporter ligands for positron emission tomography. Nucl. Med. Biol. 23, 141-146.

Chinese Application No. 201980031755.9, Office Action dated Jan. 19, 2023, 4 pages.

Chinese Application No. 201980031755.9, "Office Action," dated Jun. 14, 2023, 11 pages.

* cited by examiner

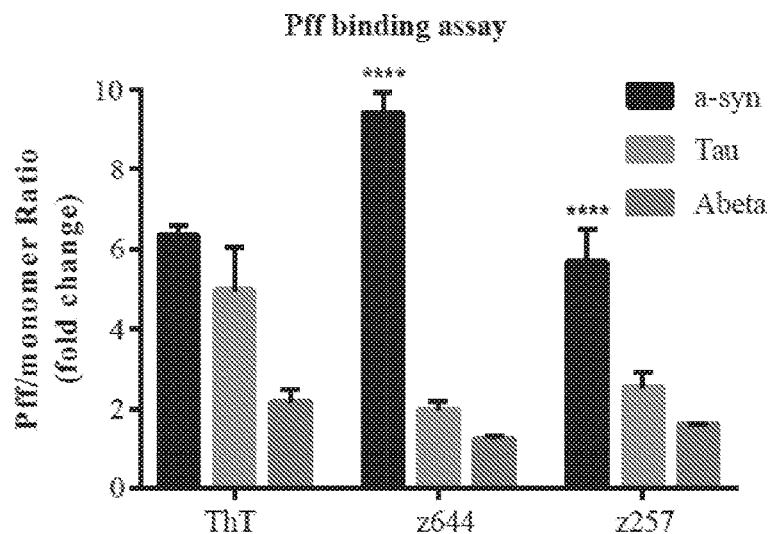
FIG. 1B
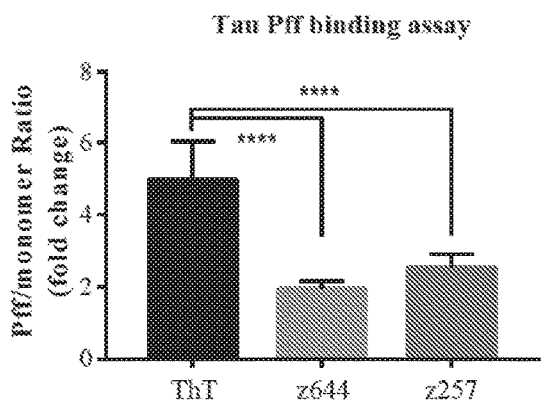 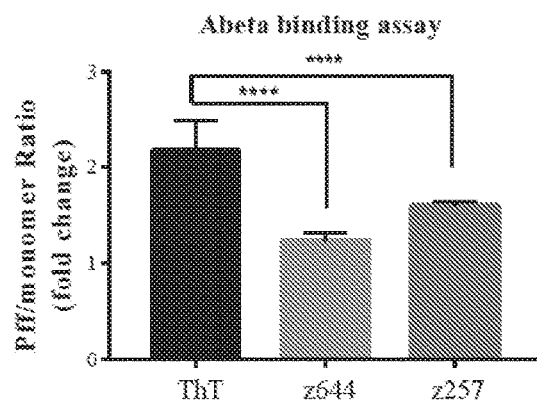
FIG. 1C              FIG. 1D

| CAS number | Structure | formula |
|---|---|---|
| EU-001-01A | 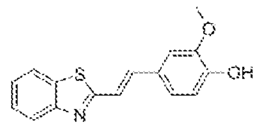 | $C_{16}H_{13}NO_2S$ |
| EU-001-01B | 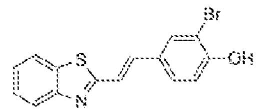 | $C_{15}H_{10}BrNOS$ |
| EU-002-01A | 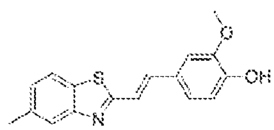 | $C_{17}H_{15}NO_2S$ |
| EU-002-01B | 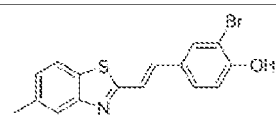 | $C_{16}H_{12}BrNOS$ |
| EU-003-01A a-syn | 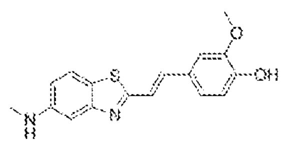 | $C_{17}H_{16}N_2O_2S$ |
| EU-003-01B a-syn | 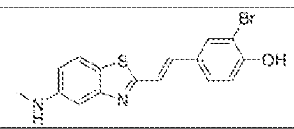 | $C_{16}H_{13}BrN_2OS$ |
| EU-004-01A Abeta | 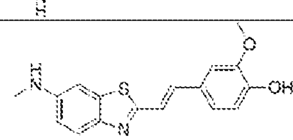 | $C_{17}H_{16}N_2O_2S$ |
| EU-004-01B Abeta | 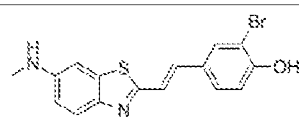 | $C_{16}H_{13}BrN_2OS$ |
| EU-004-02A | 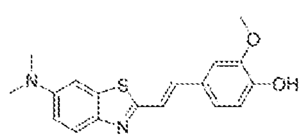 | $C_{18}H_{18}N_2O_2S$ |
| EU-004-02B | 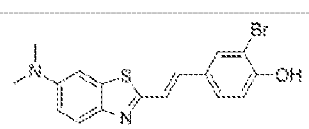 | $C_{17}H_{15}BrN_2OS$ |
| EU-004-03A | 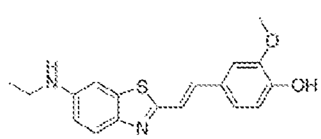 | $C_{18}H_{18}N_2O_2S$ |

FIG. 1E

| | | |
|---|---|---|
| EU-004-03B | | $C_{17}H_{15}BrN_2OS$ |
| EU-005-01A | | $C_{18}H_{18}N_2O_2S$ |
| EU-005-01B | | $C_{17}H_{15}BrN_2OS$ |
| EU-005-02A | | $C_{19}H_{20}N_2O_2S$ |
| EU-005-02B | | $C_{18}H_{17}BrN_2OS$ |
| EU-005-03A | | $C_{19}H_{20}N_2O_2S$ |
| EU-005-03B | | $C_{18}H_{17}BrN_2OS$ |
| Compound 1(TJ1) | | $C_{18}H_{17}NO_2S$ |

STYRYLBENZOTHIAZOLE DERIVATIVES AND USES IN IMAGING METHODS

CROSS-REFERENCE TO RELATED APPLICATIONS

This application is the National Stage of International Application No. PCT/US2019/032592 filed May 16, 2019, which claims the benefit of U.S. Provisional Application No. 62/672,230 filed May 16, 2018, and U.S. Provisional Application No. 62/725,615 filed Aug. 31, 2018. The entirety of each of these applications is hereby incorporated by reference for all purposes.

STATEMENT REGARDING FEDERALLY SPONSORED RESEARCH

This invention was made with government support under AG051538 awarded by the National Institutes of Health. The government has certain rights in the invention.

BACKGROUND

Parkinson's disease (PD) may be characterized by the progressive development of Lewy bodies (LB) and Lewy neurites (LN). These LB and LN consist mostly of aggregations of the protein α-synuclein (Spillantini et al 1997 Nature; 388: 839-40), which is found in healthy nerve cells as an unfolded membrane-bound protein. Alpha(α)-synuclein detaches from the membrane and takes on a β-sheet conformation which permits aggregation and consequent formation of LB and LN.

Kotzbauer et al. report PET radiotracers for imaging alpha synuclein aggregates in Lewy bodies and Lewy neurites. Clinical and Translational Imaging, 2016, 5, 3-14. 6-[$^{18}$F]-Fluoro-L-dopa is used as a PET tracer to evaluate the function of dopaminergic neurons. The SPECT tracer [$^{123}$I]-2-[β]-carbomethoxy-3-[β]-(4-iodophenyl)-tropane is used to evaluate the function of the monoamine vesicular transporter. WO 2004/075882 discloses an in vivo imaging method to diagnose the presence of abnormally folded or aggregated protein and/or amyloid fibril or amyloid in a subject where the method comprises administration of a radiolabeled inositol derivative. WO 2004/075882 report in vivo imaging methods can be applied for the diagnosis of PD. See also WO 2010/063701, WO 2004/100998, and WO 2005/013889.

The above-described in vivo imaging techniques target the disease process at a stage when LB and LN are present in the CNS. At this stage, clinical symptoms are evident, and about 80% of striatal dopamine neurons and 50% of nigral neurons are lost. As the neurons of the CNS cannot regenerate on their own after cell death, neuroprotective treatment will only benefit neurons if still alive at the time of diagnosis. It would be advantageous for patients to get treatment to curb disease progression as early as possible. There is therefore a need for a method to identify PD before significant loss of neurons.

SUMMARY

This disclosure relates to styrylbenzothiazole derivatives for use as in vivo imaging agents for the diagnosis of Parkinson's disease (PD) or other degenerative disorders or conditions of the central nervous system. Early diagnosis is particularly advantageous as neuroprotective treatment can be applied to healthy neural cells to delay or even prevent the onset of debilitating clinical symptoms.

In certain embodiments, the styrylbenzothiazole derivatives are compound of Formula I:

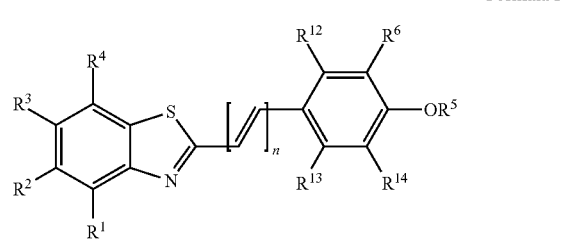

Formula I or a salt or solvate thereof, wherein:
n is 1 to 10;
$R^{1-4}$ and $R^{12-14}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl; wherein at least one $R^{1-4}$ comprises an in vivo imaging moiety; $R^5$ is hydrogen, $C_{1-6}$ carboxyalkyl or $C_{1-6}$ alkyl; and $R^6$ is halogen, hydroxyl, $C_{1-6}$ alkoxy, $C_{1-6}$ alkyl, $C_{2-6}$ alkenyl, or $C_{2-6}$ alkynyl.

In certain embodiments, $R^{12}$ is hydrogen, halogen, hydroxyl, $C_{1-6}$ alkoxy, $C_{1-6}$ alkyl, $C_{2-6}$ alkenyl, or $C_{2-6}$ alkynyl; $R^{13}$ is hydrogen, halogen, hydroxyl, $C_{1-6}$ alkoxy, $C_{1-6}$ alkyl, $C_{2-6}$ alkenyl, or $C_{2-6}$ alkynyl; and $R^{14}$ is hydrogen, halogen, hydroxyl, $C_{1-6}$ alkoxy, $C_{1-6}$ alkyl, $C_{2-6}$ alkenyl, or $C_{2-6}$ alkynyl.

In certain embodiments, $R^{12}$ and $R^{13}$ are hydrogen, and $R^{14}$ is hydroxy or $C_{1-6}$ alkoxy.

In certain embodiments, the in vivo imaging moiety is selected from $^{99m}$Tc, $^{11}$C, $^{13}$N, $^{18}$F, $^{123}$I, and $^{124}$I.

In certain embodiments, $R^6$ is $C_{1-6}$ alkoxy or halogen.

In certain embodiments, $R^5$ is hydrogen.

In certain embodiments, $R^2$ is $C_{1-6}$ alkyl and $R^3$ is an amino group —NR$^9$R$^{10}$, wherein $R^9$ and $R^{10}$ are independently hydrogen or an R group as defined in Formula I, and $R^9$ comprises the in vivo imaging moiety.

In certain embodiments, n is 1 or 2.

In certain embodiments, the styrylbenzothiazole derivatives are compound of Formula II:

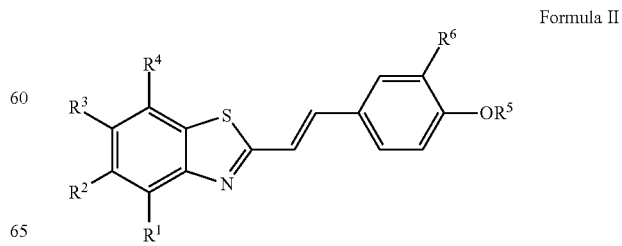

Formula II or a salt or solvate thereof, wherein:
$R^{1-4}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl; wherein at least one $R^{1-4}$ comprises an in vivo imaging moiety; $R^5$ is hydrogen, $C_{1-6}$ carboxyalkyl or $C_{1-6}$ alkyl; and $R^6$ is halogen, hydroxyl, $C_{1-6}$ alkoxy, $C_{1-6}$ alkyl, $C_{2-6}$ alkenyl, or $C_{2-6}$ alkynyl.

In certain embodiments, the in vivo imaging moiety is selected from $^{99m}$Tc, $^{11}$C, $^{13}$N, 18F, $^{123}$I and $^{124}$I.

In certain embodiments, $R^6$ is $C_{1-6}$ alkoxy or halogen.

In certain embodiments, $R^5$ is hydrogen.

In certain embodiments, $R^2$ is $C_{1-6}$ alkyl and $R^3$ is an amino group —NR$^9$R$^{10}$, wherein R$^9$ and R$^{10}$ are independently hydrogen or an R group as defined in Formula II, and R$^9$ comprises the in vivo imaging moiety.

In certain embodiments, this disclosure relates to methods of imaging comprising: a) administering a compound as described herein to a subject: b) scanning an area of the subject for an in vivo imaging moiety; c) locating the in vivo imaging moiety in an area of the subject; and d) creating an image of the subject indicating the location of the in vivo imaging moiety.

In certain embodiments, this disclosure relates to methods of brain imaging comprising: a) administering a compound as described herein to a subject: b) scanning the brain of the subject for an in vivo imaging moiety; c) locating the in vivo imaging moiety in an area of the brain of the subject; and d) creating an image of the subject indicating the location of the in vivo imaging moiety.

In certain embodiments, this disclosure relates to methods of detecting pre-formed fibrils (PFFs) of alpha-Synuclein in the brain comprising: a) administering a compound as described herein to a subject: b) scanning the brain of the subject for an in vivo imaging moiety; c) locating the in vivo imaging moiety in an area of the brain of the subject; and d) creating an image of the subject indicating the location the in vivo imaging moiety indicating the presence of pre-formed fibrils (PFFs) of alpha-synuclein.

In certain embodiments, this disclosure relates to methods of diagnosis and treating a subject with or at risk of developing Parkinson's disease comprising: a) administering a compound as described herein to a subject: b) scanning the brain of the subject for an in vivo imaging moiety; c) locating the in vivo imaging moiety in an area of the brain of the subject; and d) creating an image of the subject indicating the location the in vivo imaging moiety indicating the presence of pre-formed fibrils (PFFs) of alpha-Synuclein; and e) diagnosing the subject with or at risk of developing Parkinson's disease. In certain embodiments, treating is administering an effective amount of an anti-Parkinson's agent. In certain embodiments, the anti-Parkinson's agent is a dopamine agonist, such as ropinirole, pramipexole, and rotigotine; safinamide; amantadine; selegiline and/or rasagiline; trihexyphenidyl and/or benztropine; tolcapone and/or entacapone; levodopa, and/or carbidopa; or combinations thereof.

In certain embodiments, this disclosure relates to methods of preparing compounds disclosed herein comprising mixing starting materials and optionally reagents under conditions such that the products are formed.

In certain embodiments, this disclosure relates to pharmaceutical compositions comprising compounds disclosed herein and a pharmaceutically acceptable excipient.

BRIEF DESCRIPTION OF THE DRAWINGS

FIG. 7B shows compound structures.

DETAILED DESCRIPTION

Figure 1A:
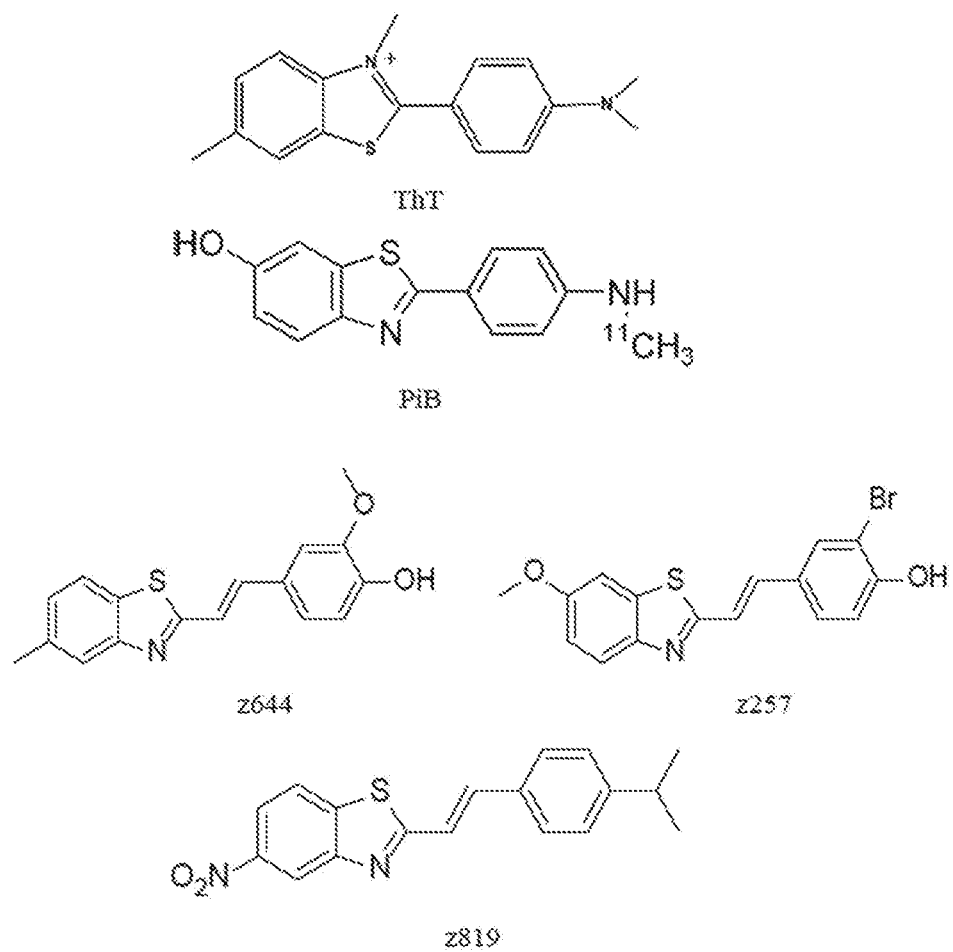
FIG. 1A illustrates the chemical structure of certain compounds used in experiments disclosed herein.
Figure 1G:
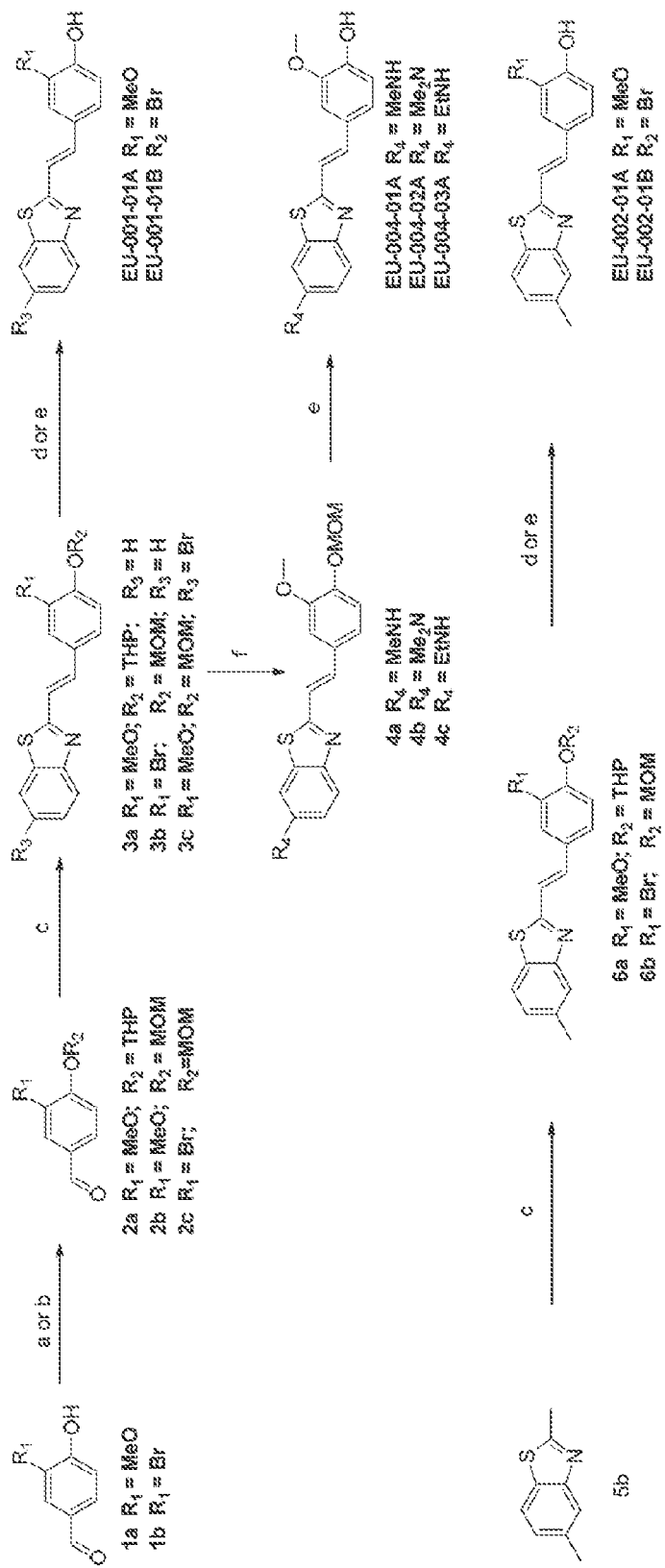
FIG. 1G illustrates the synthesis of compounds disclosed herein. Reagent and conditions: (a) (for 2a) DHP, PPTs, THF, reflux; (b) (for 2b,c) MOMBr, TEA, CH$_2$Cl$_2$, rt; (c) benzothiazole, NaH, THF, rt; (d) TsOH, MeOH, rt; (e) TFA, CH2Cl2, 0° C. then rt; (f) EtNH$_2$, Pd$_2$(dba)$_3$, XantPhos, Cs$_2$CO$_3$, dioxane, 90° C.
Figure 1H:
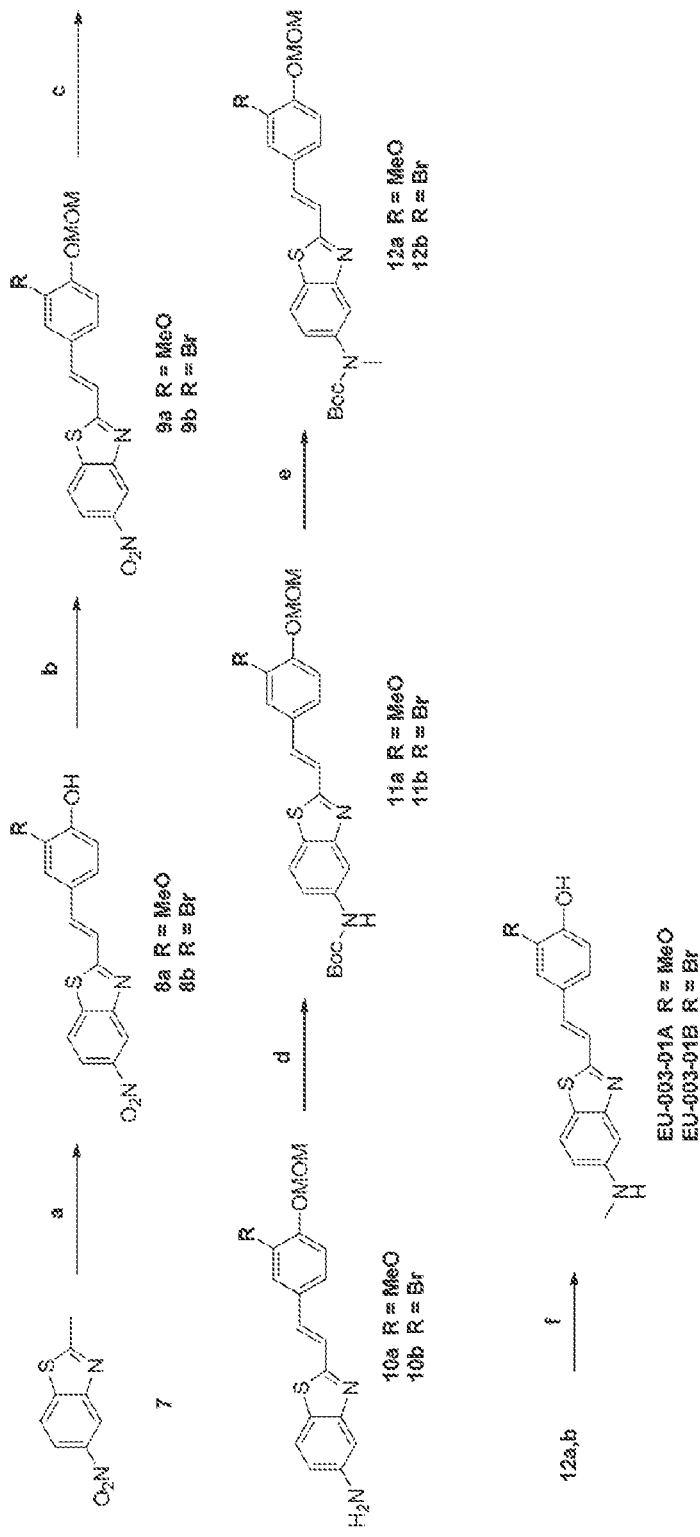
FIG. 1H illustrates the synthesis of compounds disclosed herein. Reagent and conditions: (a) 2-bromo-4-methylphenol, H$_2$SO$_4$, dioxane, 100° C.; (b) MOMBr, TEA, CH$_2$Cl$_2$, rt; (c) Zn, NH$_4$Cl, MeOH, rt; (d) Boc$_2$O, 80° C.; (e) MeI, NaH, DMF, rt; (f) TFA, CH$_2$Cl$_2$, rt.
Figure 1I:
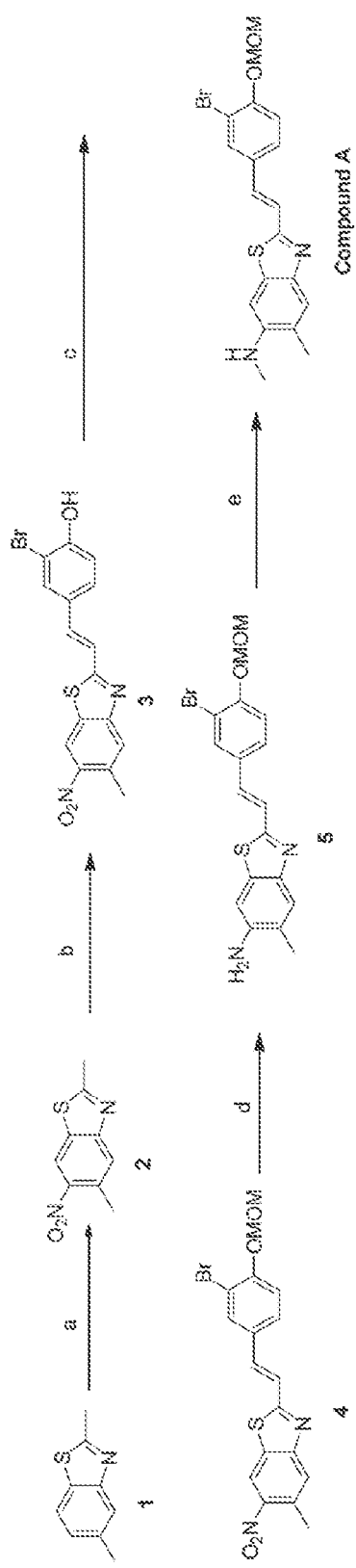
FIG. 1I illustrates the synthesis of compounds disclosed herein. Reagents and conditions: (a) HNO$_3$, H$_2$SO$_4$, 0° C.-rt; (b) 3-bromo-4-hydroxybenzaldehyde, H$_2$SO$_4$, dioxane, 100° C.; (c) MOMBr, K$_2$CO$_3$, DMF, 70° C.; (d) Fe, NH$_4$Cl, MeOH, rt; (e) MeI, K$_2$CO$_3$, DMF, 30° C.
Figure 1J:
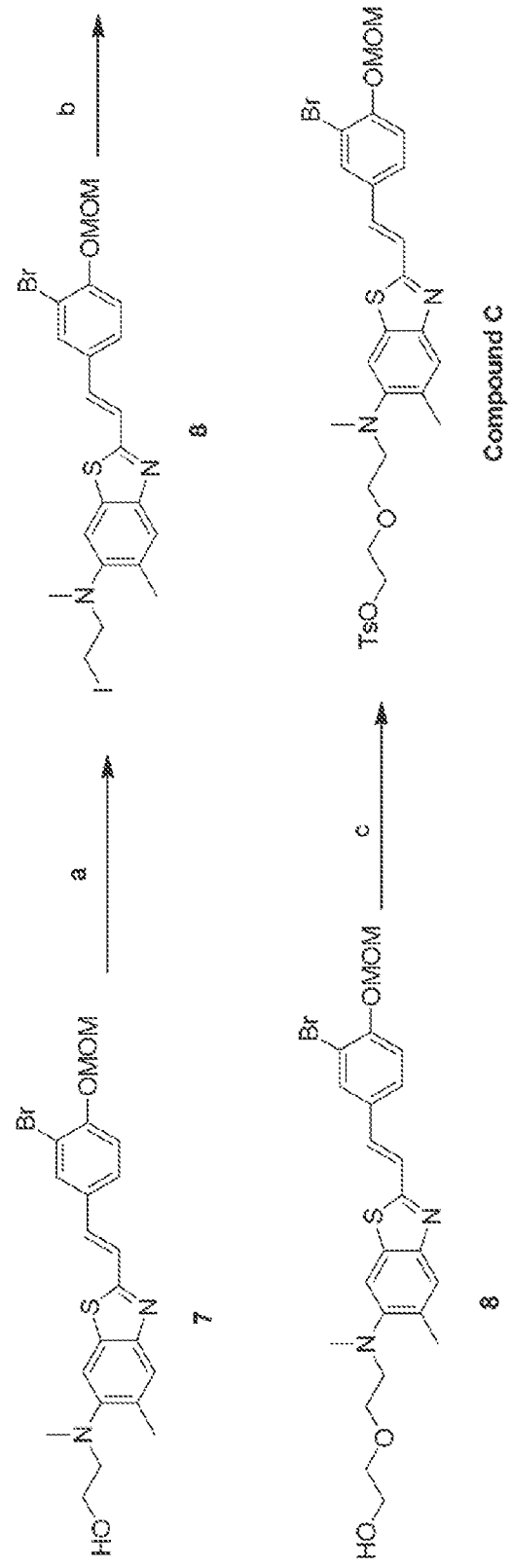
FIG. 1B shows data of an in vitro binding assay with pre-formed fibrils (PFFs) of α-Synuclein.
FIG. 1C shows data of an in vitro binding assay with pre-formed fibrils (PFFs) of Tau.
FIG. 1D shows data of an in vitro binding assay AD.
FIG. 1E illustrates the chemical structure of compounds disclosed herein.
FIG. 1F illustrates the chemical structure of compounds disclosed herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The "subject" of the disclosure is preferably a mammal, preferably an intact mammalian body in vivo. In an especially preferred embodiment, the subject of the disclosure is a human.

"Positron emission tomography" (PET) refers to an imaging technique that produces an image, e.g., three-dimensional image, by detecting pairs of gamma rays emitted indirectly by a positron-emitting radionuclide tracer. Images of tracer concentration within the area are then constructed by computer analysis. A radioactive tracer is administered to a subject e.g., into blood circulation. Typically, there is a waiting period while tracer becomes concentrated in areas of interest; then the subject is placed in the imaging scanner. As the radionuclide undergoes positron emission decay, it emits a positron, an antiparticle of the electron with opposite charge, until it decelerates to a point where it can interact with an electron, producing a pair of (gamma) photons moving in approximately opposite directions. These are detected in a scanning device. The technique typically utilizes simultaneous or coincident detection of the pair of photons moving in approximately opposite direction (the scanner typically has a built-in slight direction-error tolerance). Photons that do not arrive in pairs (i.e. within a timing-window) are typically ignored. One typically localizes the source of the photons along a straight line of coincidence (also called the line of response, or LOR). This data is used to generate an image.

The term "radionuclide" or "radioactive isotope" refers to molecules of enriched isotopes that exhibit radioactive decay (e.g., emitting positrons). Such isotopes are also referred to in the art as radioisotopes. A radionuclide tracer does not include radioactive primordial nuclides but does include a naturally occurring isotopes that exhibit radioactive decay with an isotope distribution that is enriched, e.g., is several fold greater than natural abundance. In certain embodiments, is contemplated that the radionuclides are limited to those with a half live of less than 1 hour and those with a half-life of more than 1 hour but less than 24 hours. Radioactive isotopes are named herein using various commonly used combinations of the name or symbol of the element and its mass number (e.g., $^{18}F$, F-18, or fluorine-18).

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Methods of Use

In one aspect, this disclosure relates to an in vivo imaging agent for use in a method to determine the presence of, or susceptibility to, Parkinson's disease (PD), wherein said in vivo imaging agent comprises a styrylbenzothiazole derivative labelled with an in vivo imaging moiety, said method comprising:

(i) administering to a subject a detectable quantity of said in vivo imaging agent;
(ii) allowing said administered in vivo imaging agent of step (i) to bind to α-synuclein deposits in the autonomic nervous system (ANS) of said subject;
(iii) detecting signals emitted by said bound in vivo imaging agent of step (ii) using an in vivo imaging method;
(iv) generating an image representative of the location and/or amount of said signals; and,
(v) using the image generated in step (iv) to determine of the presence of, or susceptibility to, PD.

In certain embodiments, this disclosure relates to uses of a styrylbenzothiazole derivative labelled with an in vivo imaging moiety disclosed herein for imaging methods. In certain embodiments, this disclosure relates to imaging method comprising: a) administering a styrylbenzothiazole derivative labelled with an in vivo imaging moiety disclosed herein containing an element isotopically enriched with an element providing a radionuclide, such as a nitrogen-13, carbon-11, or fluorine-18 radionuclide, to a subject; and b) scanning the subject for emissions. In certain embodiments, the method further comprises the step of detecting the emissions and creating an image indicating or highlighting the location of the styrylbenzothiazole derivative containing radionuclide in an area of the subject.

After a styrylbenzothiazole derivative labelled with an in vivo imaging moiety disclosed herein is administered to a subject, the subject is then imaged. The styrylbenzothiazole derivative can be administered at any suitable dose. The subject can be imaged using any suitable imaging apparatus, for example an apparatus capable of gathering a magnetic resonance image (MRI), a positron emission tomogram (PET scan) or a computer tomogram (CT scan).

In certain embodiments, the styrylbenzothiazole derivative disclosed herein are labeled with a radionuclide suitable for imaging with gamma, PET or SPECT imaging technology, preferably an isotope suitable for PET imaging. In other embodiments, the compounds described herein are labeled with $^{11}$C, or $^{13}$C, for example by incorporating into the carbons of the compounds, for MRI or MRS imaging. In other embodiments, the compounds described herein are labeled with a dye, for example, a near-infrared dye, suitable for optical imaging.

In certain embodiments, this disclosure relates to methods comprising: a) administering a styrylbenzothiazole derivative labelled with an in vivo imaging moiety disclosed herein containing a radionuclide to a subject and b) scanning the subject for emissions so that an image is created or the location of the radionuclide is identified or tracked.

In certain embodiments, the subject had a memory deficiency identified by a prior test or has α-synuclein deposits identified by a prior test, and are seeking a diagnosis, or the subject had an existing diagnosis of Parkinson's disease or other neurodegenerative disorder and are having further monitoring. In certain embodiments, the subject is asymptomatic and used for an early Parkinson's disease detection.

Symptoms of Parkinson's disease are all related to voluntary and involuntary motor function and may start on one side of the body. Symptoms are typically mild at first and will progress over time.

The term "α-synuclein deposits" refers to insoluble proteinaceous inclusions comprising the protein α-synuclein. Lewy bodies (LB) and Lewy neurites (LN) are well-known insoluble proteinaceous inclusions wherein α-synuclein is the main component, and in PD have been reported to be present in the central nervous system (CNS) as well as in the ANS. However, PD is conventionally considered as a disease of the CNS and known in vivo imaging methods for the detection of PD target α-synuclein deposits present in the CNS.

The "central nervous system" (CNS) is that part of the nervous system in vertebrates consisting of the brain and the spinal cord. In the CNS, endothelial cells are packed together more tightly than in the rest of the body by means of "tight junctions", which are multifunctional complexes that form a seal between adjacent epithelial cells, preventing the passage of most dissolved molecules from one side of the epithelial sheet to the other. This forms the blood-brain barrier (BBB), which blocks the movement of all molecules except those that cross cell membranes by means of lipid solubility (such as oxygen, carbon dioxide, ethanol, and steroid hormones) and those that are allowed in by specific transport systems (such as sugars and some amino acids). Substances with a molecular weight higher than 500 Da (such as antibodies) generally cannot cross the BBB by passive diffusion, while smaller molecules often can. In order for an in vivo imaging agent to come into contact with a target in the CNS, its chemical structure has to be tailored for passage across the BBB, or alternatively the in vivo imaging agent has to be administered directly into the CNS using relatively invasive procedures.

The peripheral nervous system (PNS) resides or extends outside the CNS. Unlike the CNS, the PNS is not protected by the BBB. The peripheral nervous system is divided into the somatic nervous system and the autonomic nervous system. The "autonomic nervous system" (ANS) (also known as the visceral nervous system) is the part of the PNS that acts as a control system, maintaining homeostasis in the body. These activities are generally performed without conscious control or sensation. Whereas most of its actions are involuntary, some, such as breathing, work in tandem with the conscious mind. Its main components are its sensory system, motor system (comprised of the parasympathetic nervous system and sympathetic nervous system), and the enteric nervous system (ENS; controls the gastrointestinal system).

In certain embodiments, this disclosure relates to methods comprising administering a detectable quantity of an in vivo imaging agent to a subject. In certain embodiments, this disclosure relates to methods of generating a diagnostically-useful image, administration to the subject of said in vivo imaging agent can be understood to be a preliminary step necessary for facilitating generation of said image. In an alternative embodiment the method of the disclosure can be said to begin by providing a subject to whom a detectable quantity of an in vivo imaging agent has been administered. "Administering" the in vivo imaging agent means introducing the in vivo imaging agent into the subject's body, and is preferably carried out parenterally, preferably intravenously. The intravenous route represents an efficient way to deliver the in vivo imaging agent throughout the body of the subject.

The term "in vivo imaging agent" broadly refers to a compound which can be detected following its administration to the mammalian body in vivo. The in vivo imaging agent of the present disclosure comprises a styrylbenzothiazole derivative labelled with an in vivo imaging moiety. The term "labelled with an in vivo imaging moiety" means either (i) that a particular atom of the styrylbenzothiazole derivative is an isotopic version suitable for in vivo detection, or (ii) that a group comprising said in vivo imaging moiety is conjugated to said styrylbenzothiazole derivative. In certain embodiments, the in vivo imaging agent has binding affinity for α-synuclein in the range 0.1 nM-50 μM, preferably 0.1 nM-100 μM and preferably 0.1-100 nM.

Masuda et al (2006 Biochemistry; 45: 6085-94) describe an assay for testing the ability of compounds to bind to α-synuclein in vitro. In the assay, a test compound is incubated with a solution of α-synuclein at 37° C. for 72 hours, followed by addition of the detergent sarkosyl (sodium lauroyl sarcosinate) to facilitate determination of the relative proportions of soluble and insoluble α-synuclein. $IC_{50}$ values for the test compounds can be calculated by quantifying the amount of sarkosyl-insoluble α-synuclein. This assay can therefore be used to test the suitability of a particular in vivo imaging agent for the present disclosure.

An "in vivo imaging moiety" may be detected either externally to the human body, or via use of detectors designed for use in vivo, such as intravascular radiation or optical detectors such as endoscopes, or radiation detectors designed for intra-operative use.

The "detection" step of the method of the disclosure involves the detection of signals either externally to the human body or via use of detectors designed for use in vivo, such as intravascular radiation or optical detectors such as endoscopes (e.g. suitable for detection of signals in the gut), or radiation detectors designed for intra-operative use. This detection step can also be understood as the acquisition of signal data.

The "in vivo imaging method" selected for detection of signals emitted by said in vivo imaging moiety depends on the nature of the signals. Therefore, where the signals come from a paramagnetic metal ion, magnetic resonance imaging (MRJ) is used, where the signals are gamma rays, single photon emission tomography (SPECT) is used, where the signals are positrons, positron emission tomography (PET) is used, and where the signals are optically active, optical imaging is used. All are suitable for use in the method of the present disclosure, with PET and SPECT are preferred, as they are least likely to suffer from background and therefore are diagnostically useful.

The "generation" step of the method of the disclosure is carried out by a computer which applies a reconstruction algorithm to the acquired signal data to yield a dataset. This dataset is then manipulated to generate images showing areas of interest within the subject.

In Vivo Imaging Moieties

In certain embodiments, the in vivo imaging moiety is preferably chosen from: (i) a radioactive metal ion; (ii) a paramagnetic metal ion; (iii) a gamma-emitting radioactive halogen; (iv) a positron-emitting radioactive non-metal; (v) a reporter suitable for in vivo optical imaging. In vivo imaging agents may be conveniently prepared by reaction of a precursor compound with a suitable source of the in vivo imaging moiety. A "precursor compound" comprises a derivative of the in vivo imaging agent, designed so that chemical reaction with a convenient chemical form of the in vivo imaging moiety occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity. The precursor compound may optionally comprise a protecting group for certain functional groups of the precursor compound.

By the term, "protecting group" is meant a group which inhibits or suppresses undesirable chemical reactions, but which is designed to be sufficiently reactive that it may be cleaved from the functional group in question under mild enough conditions that do not modify the rest of the molecule. After deprotection, the desired in vivo imaging agent is obtained. Protecting groups are well-known to those skilled in the art and are suitably chosen from, for amine groups: Boc (where Boc is terZ-butyloxycarbonyl), Fmoc (where Fmoc is fluorenylmethoxycarbonyl), trifluoroacetyl, allyloxycarbonyl, Dde (i.e. 1-(4,4-dimethyl-2,6-dioxocyclohexylidene)ethyl) or Npys (i.e. 3-nitro-2-pyridine sulfonyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and methoxybenzyl. The use of protecting groups is described in "Protective Groups in Organic Synthesis," Theorodora W. Greene and Peter G. M. Wuts, (Third Edition, John Wiley & Sons, 1999).

The term "hydroxyl protecting group" or "O-protected" as used herein refers to those groups intended to protect an OH group against undesirable reactions during synthetic procedures and which can later be removed to reveal the hydroxyl group. Hydroxy protecting groups include moieties such as allyl, benzyl, methoxymethyl, ethoxyethyl, methyl thiomethyl, benzyloxymethyl, t-butyl, trityl, methoxytrityl, tetrahydropyranyl, 2-napthylmethyl, p-methoxybenzyl, o-nitrobenzyl, 9-Phenylxanthyl, silyl groups such as trimethylsilyl, triethylsilyl, triisopropylsilyl, t-butyldimethylsilyl, t-butyldiphenylsilyl, phenyldimethylsilyl, acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl, 4-bromobenzoyl, 4-nitrobenzoyl, and the like; and sulfonyl groups such as benzenesulfonyl, p-toluenesulfonyl and the like.

When the in vivo imaging moiety is a radioactive metal ion, i.e. a radiometal, suitable radiometals can be either positron emitters such as $^{64}$Cu, $^{48}$V, $^{52}$Fe, $^{55}$Co, $^{94m}$Tc or $^{68}$Ga; γ-emitters such as $^{99m}$Tc, $^{111}$In, $^{113}$In, or $^{67}$Ga. Preferred radiometals are $^{99m}$Tc, $^{64}$Cu, $^{68}$Ga and $^{111}$In. Preferred radiometals are γ-emitters, especially $^{99m}$Tc.

When the in vivo imaging moiety is a paramagnetic metal ion, suitable such metal ions include: Gd(III), Mn(II), Cu(II), Cr(III), Fe(III), Co(II), Er(II), Ni(II), Eu(III) or Dy(UI). Preferred paramagnetic metal ions are Gd(III), Mn(II) and Fe(III), with Gd(III) being especially preferred. When the imaging moiety comprises a metal ion, it is preferably present as a metal complex of the metal ion with a synthetic ligand. By the term "metal complex" is meant a coordination complex of the metal ion with one or more ligands. It is strongly preferred that the metal complex is "resistant to transchelation", i.e. does not readily undergo ligand exchange with other potentially competing ligands for the metal coordination sites. Potentially competing ligands include other excipients in the preparation in vitro (e.g. radioprotectants or antimicrobial preservatives used in the preparation), or endogenous compounds in vivo (e.g. glutathione, transferrin or plasma proteins). The term "synthetic" has its conventional meaning, i.e. man-made as opposed to being isolated from natural sources e.g. from the mammalian body. Such compounds have the advantage that their manufacture and impurity profile can be fully controlled.

Suitable ligands for use in the present disclosure which form metal complexes resistant to transchelation include: chelating agents, where 2-6, preferably 2-4, metal donor atoms are arranged such that 5- or 6-membered chelate rings result (by having a non-coordinating backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes, and phosphines. Phosphines form such strong metal complexes that even monodentate or bidentate phosphines form suitable metal complexes. The linear geometry of isonitriles and diazenides is such that they do not lend themselves readily to incorporation into chelating agents and are hence typically used as monodentate ligands. Examples of suitable isonitriles include simple alkyl isonitriles such as tert-butylisonitrile, and ether-substituted isonitriles such as MIBI (i.e. 1-isocyano-2-methoxy-2-methylpropane). Examples of suitable phosphines include tetrofosmin, and monodentate phosphines such as tris(3-methoxypropyl)phosphine. Examples of suitable diazenides include the HYNIC series of ligands i.e. hydrazine-substituted pyridines or nicotinamides.

When the metal ion is technetium, suitable chelating agents which form metal complexes resistant to transchelation include, but are not limited to: (i) diaminedioximes; (ii) $N_3S$ ligands having a thioltriamide donor set such as MAG3 (mercaptoacetyltriglycine) and related ligands; or having a diamidepyridinethiol donor set such as Pica, (iii) $N_2S_2$ ligands having a diaminedithiol donor set such as BAT or ECD (i.e. ethylcysteinate dimer), or an amideaminedithiol donor set such as MAMA; (iv) N4 ligands which are open chain or macrocyclic ligands having a tetraamine, amidetriamine or diamidediamine donor set, such as cyclam, monoxocyclam dioxocyclam; and, (v) $N_2O_2$ ligands having a diaminediphenol donor set. Examples of chelates that are particularly suitable for complexing $^{99m}Tc$ are described in WO 2003/006070 and WO 2006/008496.

Where a compound is labelled with a gamma-emitting radioactive halogen, suitable precursor compounds are those which comprise a derivative which either undergoes electrophilic or nucleophilic halogenation or undergoes condensation with a labelled aldehyde or ketone. Examples of the first category are: (a) organometallic derivatives such as a trialkylstannane (eg. trimethylstannyl or tributylstannyl), or a trialkylsilane (eg. trimethylsilyl) or an organoboron compound (e.g. boronate esters or organotrifluoroborates); (b) a non-radioactive alkyl bromide for halogen exchange or alkyl tosylate, mesylate or triflate for nucleophilic halogenation; (c) aromatic rings activated towards electrophilic halogenation (e.g. phenols, phenylamines) and aromatic rings activated towards nucleophilic halogenation (e.g. aryl iodonium salt aryl diazonium, aryl trialkylammonium salts or nitroaryl derivatives).

The precursor compound for radiohalogenation preferably comprises: a non-radioactive halogen atom such as an aryl iodide or bromide (to permit radioiodine exchange); an activated aryl ring (e.g. a phenol or phenylamine); an organometallic substituent (e.g. trialkyltin, trialkylsilyl or organoboron compound); or an organic substituent such as triazenes or a good leaving group for nucleophilic substitution such as an iodonium salt. Preferably, for radiohalogenation, the precursor compound comprises an activated aryl ring or an organometallic substituent, said organometallic substituent preferably being trialkyltin.

A preferred gamma-emitting radioactive halogen is radioiodine. Precursor compounds and methods of introducing radioiodine into organic molecules are described by Bolton (J. Lab. Comp. Radiopharm., 2002, 45: 485-528). Suitable boronate ester organoboron compounds and their preparation are described by Kabalaka et al (Nucl.Med.Biol., 2003; 29: 841-843 and 30: 369-373). Suitable organotrifluoroborates and their preparation are described by Kabalaka et al (Nucl.Med.BioL, 2004; 31: 935-938).

Radioactive iodine can be attached aryl groups via $Sn(alkyl)_3$ or phenol (OH) intermediates. Alkyl in this case is preferably methyl or butyl. These groups contain substituents which permit radioiodine substitution onto the aromatic ring. Alternative substituents containing radioactive iodine can be synthesized by direct iodination via radioiodine exchange. The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine. The source of the radioiodine is chosen from iodide ion or the iodonium ion (I+). Preferably, the chemical form is iodide ion, which is typically converted to an electrophilic species by an oxidant during radiosynthesis.

In certain embodiments, the in vivo imaging moiety is a positron-emitting radioactive moiety. Such positron emitters include: $^{11}C$, $^{13}N$, $^{15}O$, $^{17}F$, $^{18}F$, $^{75}Br$, $^{76}Br$ or $^{124}I$. Preferred positron-emitting radioactive moieties are $^{11}C$, $^{13}N$, $^{18}F$ and $^{124}I$, especially $^{11}C$ and $^{18}F$, especially $^{18}F$. Techniques for introduction of these in vivo imaging moieties are well-known to those of skill in the art of positron emission tomography (PET) imaging. Some of these techniques are now described.

Where a compound is labelled with $^{11}C$, one approach to labelling is to react a precursor compound which is the desmethylated version of a methylated compound with [$^{11}C$]methyl iodide. It is also possible to incorporate $^{11}C$ by reacting Grignard reagent of the particular hydrocarbon chain of the desired labelled compound with [$^{11}C$]$CO_2$. $^{11}C$ could also be introduced as a methyl group on an aromatic ring, in which case the precursor compound would include a trialkyltin group or a $B(OH)_2$ group. As the half-life of $^{11}C$ is 20.4 minutes, it is important that the intermediate $^{11}C$ moieties have high specific activity and consequently are produced using a reaction process which is as rapid as possible.

To label a compound with a radioactive isotope of fluorine the radiofluorine atom may form part of a fluoroalkyl or fluoroalkoxy group, since alkyl fluorides are resistant to in vivo metabolism. Fluoroalkylation may be carried out by reaction of a precursor compound containing a reactive group such as phenol, thiol and amide with a fluoroalkyl group. Alternatively, the radiofluorine atom may be attached via a direct covalent bond to an aromatic ring such as a benzene ring. For such aryl systems, $^{18}F$-fluoride nucleophilic displacement from an aryl diazonium salt, aryl nitro compound or an aryl quaternary ammonium salt are suitable routes to aryl-$^{18}F$ derivatives. Radiofluorination may be carried out via direct labelling using the reaction of F-fluoride with a suitable chemical group in the precursor compound having a good leaving group, such as an alkyl bromide, alkyl mesylate or alkyl tosylate.

As the half-life of $^{18}F$ is 109.8 minutes, it is important that the intermediate $^{18}F$ moieties have high specific activity and, consequently, are produced using a reaction process which is as rapid as possible. Further details of synthetic routes to $^{18}F$-labelled derivatives are described by Bolton, J. Lab. Comp. Radiopharm., 2002; 45: 485-528.

When the in vivo imaging moiety is a reporter suitable for in vivo optical imaging, the reporter is any moiety capable of detection either directly or indirectly in an optical imaging procedure. The reporter might be a light scatterer (e.g. a colored or uncolored particle), a light absorber or a light emitter. More preferably, the reporter is a dye such as a chromophore or a fluorescent compound. The dye can be any dye that interacts with light in the electromagnetic spectrum with wavelengths from the ultraviolet light to the near infrared. Preferably, the reporter has fluorescent properties.

Preferred organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, naphthoquinones, indanthrenes, phthaloylacridones, trisphenoquinones, azo dyes, intramolecular and intermolecular charge-transfer dyes and dye complexes, tropones, tetrazines, Fe(dithiolene) complexes, Co(benzenedithiolate) complexes, iodoaniline dyes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots). Particular examples of chromophores which may be used include: fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

Particularly preferred are dyes which have absorption maxima in the visible or near infrared (NIR) region, between 400 nm and 3 m, particularly between 600 nm and 1300 nm. Optical imaging modalities and measurement techniques include, but not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarization, luminescence, fluorescence lifetime, quantum yield, and quenching.

In certain embodiments, some suitable α-synuclein binders are also reporters suitable for in vivo optical imaging. Examples of such α-synuclein binders include styrylbenzothiazole derivatives described more in detail below. These compounds can alternatively be labelled with other in vivo imaging moieties if desired.

In a preferred embodiment, the in vivo imaging moiety of the present disclosure is a radioactive metal ion, a gamma-emitting radioactive halogen, or a positron-emitting radioactive non-metal. The suitable and preferred embodiments of each are as presented above. Particularly preferred in vivo imaging moieties of the present disclosure are $^{99m}$Tc, $^{11}$C, $^{18}$F and $^{123}$I.

Radionuclides are isotopically labeled forms of compounds disclosed herein including isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S $^{18}$F, and $^{36}$Cl. Such isotopically labeled compounds are useful in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," NeuroRx 2005, 2(2), 226-236, and references cited therein. Isotopically labeled compounds of this disclosure and prodrugs thereof can generally be prepared by carrying out the procedures disclosed in the schemes or in the examples and preparations described herein by substituting a readily available isotopically labeled reagent for a non-isotopically labeled reagent.

In certain embodiments, compounds disclosed herein are substituted with $^{13}$N, Nitrogen-13. One can produce [$^{13}$N] NH$_3$, ammonium with nitrogen-13 ($^{13}$N) in an cyclotron by using the $^{16}$O(p,alpha)$^{13}$N nuclear reaction. One can irradiate EtOH in water at 18 MeV protons (22 mA beam current), pressure in the range 5-10 bar into the target during bombardment to reach integrated currents (0.1-1 mAh). See Da Silva et al. Efficient Enzymatic Preparation of 13N-Labelled Amino Acids: Towards Multipurpose Synthetic Systems, Chem. Eur. J. 2016, 22, 13619.

In certain embodiments, compounds disclosed herein are substituted with $^{18}$F, Flurone-18. Radiofluorination reactions are typically nucleophilic substitutions. Aromatic nucleophilic substitutions with fluoride usually require activated aromatic rings, bearing both a good leaving group (e.g. a halogen, a nitro- or a trimethylammonium group) and a strong electron-withdrawing substituent (e.g. a nitro-, cyano- or acyl group) preferably placed para to the leaving group, whereas aliphatic nucleophilic substitutions typically utilize leaving group (usually a halogen or a sulphonic acid derivative such as mesylate, tosylate, or triflate).

One can produced [$^{18}$F] fluoride by irradiation of water (containing H$_2$$^{18}$O) with protons resulting in the reaction $^{18}$O(p,n)$^{18}$F. For production efficiency and radiochemical purity, it is desirable to use water that is as highly enriched as possible. The [$^{18}$F] isotope is then separated from water and processed for production of a radiopharmaceutical agent. Typically, fluoride recovery is based on ion exchange resins. The recovery is carried out in two steps (extraction and elution): first the anions (not only fluoride) are separated from the enriched [$^{18}$O] water and trapped on a resin and then, said anions, including [$^{18}$F] fluoride, are eluted into a mixture containing water, organic solvents, a base, also called activating agent or phase transfer agent or phase transfer catalyst, such as the complex potassium carbonate, Kryptofix® 222 (K$_2$CO$_3$-K$_{222}$) or a tetrabutylammonium salt. Typical labeling methods use low water content solutions. An evaporation step may follow the recovery of the [$^{18}$F]fluoride, e.g., azeotropic evaporation of acetonitrile or other low boiling temperature organic solvent.

Alternatively, the extraction process is performed by passing the [$^{18}$F] aqueous solution on a solid support as reported in U.S. Pat. No. 8,641,903. This solid support is typically loaded with a trapping agent, e.g., compound comprising a quaternary amine that is adsorbed on the solid support and allows the [$^{18}$F] activity to be trapped because of its positive charge. The solid support is then flushed with a gas or a neutral solvent to remove or push out most of the residual water. The [$^{18}$F] is at last eluted in an organic solvent or in a mixture of organic solvents and is usable for the labelling of precursor compounds.

The compounds described herein could also be labeled by radionuclide bromine or iodine through traditional labeling procedures such as tributyltin derivatives. (See, for example, Plisson et al., Synthesis and in vivo evaluation of fluorine-18 and iodine-123 labeled 2beta-carbo(2-fluoroethoxy)-3beta-(4'-((Z)-2 iodoethenyl)phenyl)nortropane as a candidate serotonin transporter imaging agent. J Med Chem, 2007, 50(19):4553-60; Plisson et al, Synthesis, radiosynthesis, and biological evaluation of carbon-11 and iodine-123 labeled 2beta-carbomethoxy-3beta-[4'-((Z)-2-haloethenyl)phenyl] tropanes. J Med Chem, 2004, 47(5):1122-35; Li et al, Synthesis of structurally identical fluorine-18 and iodine isotope labeling compounds for comparative imaging. Bioconjug Chem, 2003, 14(2):287-94; Goodman et al., Synthesis and characterization of iodine-123 labeled 2beta-carbomethoxy-3beta-(4'-((Z)-2-iodoethenyl)phenyl) nortropane. J Med Chem, 2003, 46(6):925-35; Maziere et al, [76]Br-beta-CBT, a PET tracer for investigating dopamine neuronal uptake. Nucl Med Biol, 1995, 22(8):993-7.

In certain embodiments, compounds disclosed herein contain $^{11}$C, carbon-11. Methods of preparing $^{11}$C intermediates are provided in the art. Example of such methods are disclosed in, for example: Jewett et al. (1992) A Simple Synthesis of [$^{11}$C]Methyl Triflate Appl. Radiat. Isot. 43, 1383-1385; Crouzel et al. (1987) Recommendations for a practical production of [$^{11}$C]methyl iodide Appl. Radiat. Isot. Int. J. Appl. Instrum. Part A 38, 601-603; Jewett et al. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; Marazano, et al. (1977) Synthesis of methyl iodide-$^{11}$C and formaldehyde-[11]C Appl. Radiat. Isot. 28, 49-52; Watkins et al. (1988) A Captive Solvent Method for Rapid N-[$^{11}$C]Methylation of Secondary Amides Application to the Benzodiazepine, 4'-Chlorodiazepam (RO5-4864) Appl. Radiat. Isot. 39, 441-444; and Wilson et al., (1996) In vivo evaluation of [$^{11}$C] and [[15]F]-labeled cocaine analogues as potential dopamine transporter ligands for positron emission tomography. Nucl. Med. Biol. 23, 141-146.

Styrylbenzothiazole Derivatives

Quantification and distribution of the α-Syn aggregates in LBs and LNs would better define the natural disease course of PC. It was found that styrylbenzothiazole derivatives such as those which are compounds within the scope of Formula I, bind to α-Synuclein.

In certain embodiments, the styrylbenzothiazole derivatives are compound of Formula I:

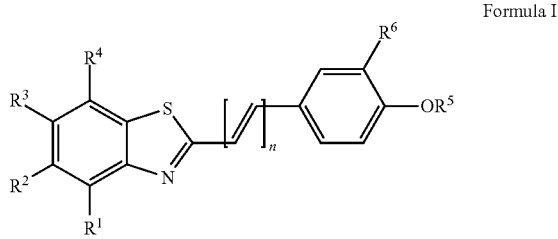

Formula I or a salt or solvate thereof, wherein:

n is 1 to 10;

$R^{1-4}$ and $R^{12-14}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl; wherein at least one $R^{1-4}$ comprises an in vivo imaging moiety; $R^5$ is hydrogen, $C_{1-6}$ carboxyalkyl or $C_{1-6}$ alkyl; and $R^6$ is halogen, hydroxyl, $C_{1-6}$ alkoxy, $C_{1-6}$ alkyl, $C_{2-6}$ alkenyl, or $C_{2-6}$ alkynyl.

In certain embodiments, n is 1 or 2.

In certain embodiments, $R^{12}$ is hydrogen, halogen, hydroxyl, $C_{1-6}$ alkoxy, $C_{1-6}$ alkyl, $C_{2-6}$ alkenyl, or $C_{2-6}$ alkynyl; $R^{13}$ is hydrogen, halogen, hydroxyl, $C_{1-6}$ alkoxy, $C_{1-6}$ alkyl, $C_{2-6}$ alkenyl, or $C_{2-6}$ alkynyl; and $R^{14}$ is hydrogen, halogen, hydroxyl, $C_{1-6}$ alkoxy, $C_{1-6}$ alkyl, $C_{2-6}$ alkenyl, or $C_{2-6}$ alkynyl.

In certain embodiments, $R^{12}$ and $R^{13}$ are hydrogen, and $R^{14}$ is hydroxy or $C_{1-6}$ alkoxy.

In certain embodiments, $R^{12}$ is hydrogen, hydroxyl, amino, or methoxy.

In certain embodiments, $R^{13}$ is hydrogen, hydroxyl, amino, or methoxy.

In certain embodiments, $R^{14}$ is hydrogen, hydroxyl, amino, or methoxy.

In certain embodiments, the in vivo imaging moiety is selected from $^{99m}$Tc, $^{11}$C, $^{13}$N, $^{18}$F, $^{123}$I, and $^{124}$I.

In certain embodiments, $R^6$ is $C_{1-6}$ alkoxy or halogen.

In certain embodiments, $R^5$ is hydrogen.

In certain embodiments, $R^2$ is $C_{1-6}$ alkyl and $R^3$ is an amino group —NR$^9$R$^{10}$, wherein R$^9$ and R$^{10}$ are independently hydrogen or an R group as defined in Formula I, and R$^9$ comprises the in vivo imaging moiety.

In one preferred embodiment, said styrylbenzothiazole derivatives is a compound of Formula II:

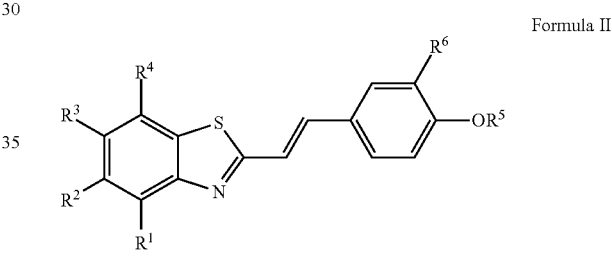

Formula II or a salt or solvate thereof, wherein:

$R^{1-4}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl;

$R^5$ is hydrogen, $C_{1-6}$ carboxyalkyl, $C_{1-6}$ alkyl, or hydroxyl protecting group;

$R^6$ is halogen, hydroxyl, $C_{1-6}$ alkoxy, $C_{1-6}$ alkyl, $C_{2-6}$ alkenyl, or $C_{2-6}$ alkynyl.

In certain embodiments, the styrylbenzothiazole derivatives are compound of Formula II:

Formula II

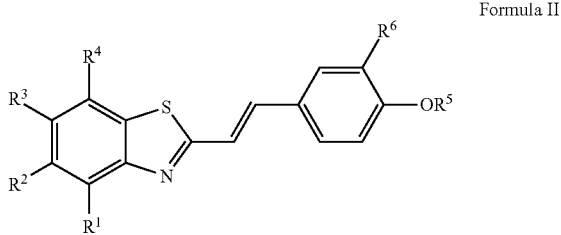

or a salt or solvate thereof, wherein:

$R^{1-4}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —$OCH_2OR'$, wherein R' is H or $C_{1-6}$ alkyl; wherein at least one $R^{1-4}$ or $R^{1-6}$ comprises an in vivo imaging moiety; $R^5$ is hydrogen, $C_{1-6}$ carboxyalkyl or $C_{1-6}$ alkyl; and $R^6$ is halogen, $C_{1-6}$ alkoxy, $C_{1-6}$ alkyl, $C_{2-6}$ alkenyl, or $C_{2-6}$ alkynyl.

In certain embodiments, the in vivo imaging moiety is selected from $^{11}C$, $^{13}N$, $^{18}F$ and $^{124}I$.

In certain embodiments, $R^6$ is $C_{1-6}$ alkoxy or halogen.

In certain embodiments, $R^5$ is hydrogen or a hydroxyl protecting group.

In certain embodiments, $R^6$ is $C_{1-6}$ alkoxy or halogen and $R^5$ is hydrogen.

In certain embodiments, $R^2$ is $C_{1-6}$ alkyl and $R^3$ is an amino group —$NR^9R^{10}$, wherein $R^9$ and $R^{10}$ are independently hydrogen or an R group as defined in Formula II, and $R^9$ comprises the in vivo imaging moiety.

In certain embodiments, the styrylbenzothiazole derivatives are compound of Formula III:

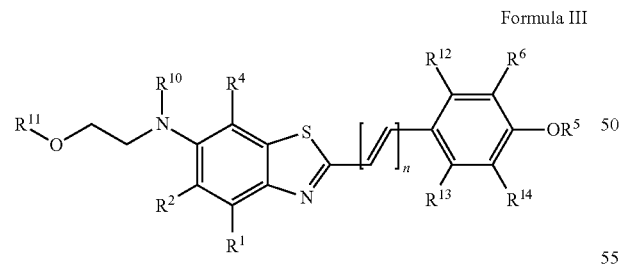

Formula III or a salt or solvate thereof, wherein:

n is 1 to 10;

$R^1$, $R^4$ and $R^{12-14}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —$OCH_2OR'$, wherein R' is H or $C_{1-6}$ alkyl; $R^2$ is hydrogen or $C_{1-6}$ alkyl; $R^5$ is hydrogen, $C_{1-6}$ carboxyalkyl, $C_{1-6}$ alkyl or hydroxyl protecting group; and $R^6$ is halogen, hydroxyl, $C_{1-6}$ alkoxy, $C_{1-6}$ alkyl, $C_{2-6}$ alkenyl, or $C_{2-6}$ alkynyl; $R^{10}$ is hydrogen or $C_{1-6}$ alkyl or an R group of formula III, and $R^{11}$ is $C_{1-6}$ alkyl or an R group comprising an in vivo imaging moiety, such as $C_{1-6}$ haloalkyl, $C_{2-6}$ haloalkenyl, or $C_{2-6}$ haloalkynyl.

In certain embodiments, n is 1 or 2.

In certain embodiments, $R^{12}$ is hydrogen, halogen, hydroxyl, $C_{1-6}$ alkoxy, $C_{1-6}$ alkyl, $C_{2-6}$ alkenyl, or $C_{2-6}$ alkynyl; $R^{13}$ is hydrogen, halogen, hydroxyl, $C_{1-6}$ alkoxy, $C_{1-6}$ alkyl, $C_{2-6}$ alkenyl, or $C_{2-6}$ alkynyl; and $R^{14}$ is hydrogen, halogen, hydroxyl, $C_{1-6}$ alkoxy, $C_{1-6}$ alkyl, $C_{2-6}$ alkenyl, or $C_{2-6}$ alkynyl.

In certain embodiments, $R^{12}$ is hydrogen, hydroxyl, amino, or methoxy.

In certain embodiments, $R^{13}$ is hydrogen, hydroxyl, amino, or methoxy.

In certain embodiments, $R^{14}$ is hydrogen, hydroxyl, amino, or methoxy.

In certain embodiments, $R^{12}$ and $R^{13}$ are hydrogen, and $R^{14}$ is hydroxy or $C_{1-6}$ alkoxy.

In certain embodiments, the in vivo imaging moiety is selected from $^{11}C$, $^{13}N$, $^{18}F$ and $^{124}I$.

In certain embodiments, $R^6$ is $C_{1-6}$ alkoxy or halogen.

In certain embodiments, $R^5$ is hydrogen or hydroxyl protecting group.

In certain embodiments, $R^6$ is $C_{1-6}$ alkoxy or halogen and $R^5$ is hydrogen.

In certain embodiments, $R^{11}$ is $C_{1-6}$ alkyl, $C_{1-6}$ haloalkyl, $C_{1-6}$ aminoalkyl comprising an in vivo imaging moiety.

In certain embodiments, the styrylbenzothiazole derivatives are compound of Formula IV:

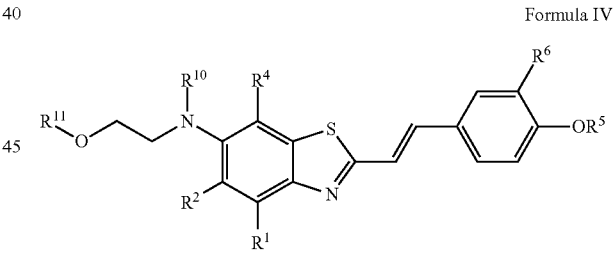

Formula IV or a salt or solvate thereof, wherein:

$R^1$ and $R^4$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —$OCH_2OR'$, wherein R' is H or $C_{1-6}$ alkyl; $R^2$ is hydrogen or $C_{1-6}$ alkyl; $R^5$ is hydrogen, $C_{1-6}$ carboxyalkyl, $C_{1-6}$ alkyl or hydroxyl protecting group; and $R^6$ is halogen, hydroxyl, $C_{1-6}$ alkoxy, $C_{1-6}$ alkyl, $C_{2-6}$ alkenyl, or $C_{2-6}$ alkynyl; $R^{10}$ is hydrogen or $C_{1-6}$ alkyl or an R group of formula IV, and $R^{11}$ is $C_{1-6}$ alkyl or an R group comprising an in vivo imaging moiety, such as $C_{1-6}$ haloalkyl, $C_{2-6}$ haloalkenyl, or $C_{2-6}$ haloalkynyl.

In certain embodiments, the in vivo imaging moiety is selected from $^{11}C$, $^{13}N$, $^{18}F$ and $^{124}I$.

In certain embodiments, $R^6$ is $C_{1-6}$ alkoxy or halogen.

In certain embodiments, $R^5$ is hydrogen or hydroxyl protecting group.

In certain embodiments, $R^6$ is $C_{1-6}$ alkoxy or halogen and $R^5$ is hydrogen.

In certain embodiments, $R^{11}$ is $C_{1-6}$ alkyl, $C_{1-6}$ haloalkyl, $C_{1-6}$ aminoalkyl comprising an in vivo imaging moiety.

In certain embodiments, the styrylbenzothiazole derivatives are compound of Formula V:

Formula V

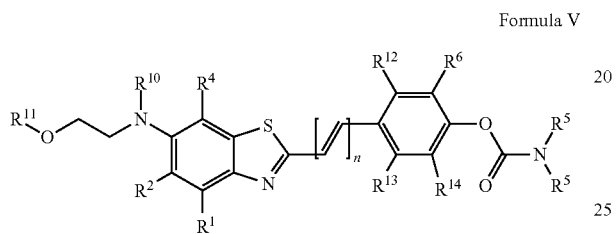

or a salt or solvate thereof, wherein:

n is 1 to 10;

$R^1$, $R^4$ and $R^{12-14}$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl; $R^2$ is hydrogen or $C_{1-6}$ alkyl; $R^5$ is, individually and independently at each occurrence, hydrogen, $C_{1-6}$ alkyl, $C_{2-6}$ alkenyl, or $C_{2-6}$ alkynyl; and $R^6$ is halogen, hydroxyl, $C_{1-6}$ alkoxy, $C_{1-6}$ alkyl, $C_{2-6}$ alkenyl, or $C_{2-6}$ alkynyl; $R^{10}$ is hydrogen or $C_{1-6}$ alkyl or an R group of formula V, and $R^{11}$ is $C_{1-6}$ alkyl or an R group comprising an in vivo imaging moiety, such as $C_{1-6}$ haloalkyl, $C_{2-6}$ haloalkenyl, or $C_{2-6}$ haloalkynyl.

In certain embodiments, n is 1 or 2.

In certain embodiments, $R^{12}$ is hydrogen, hydroxyl, amino, or methoxy.

In certain embodiments, $R^{13}$ is hydrogen, hydroxyl, amino, or methoxy.

In certain embodiments, $R^{14}$ is hydrogen, hydroxyl, amino, or methoxy.

In certain embodiments, $R^{12}$ and $R^{13}$ are hydrogen, and $R^{14}$ is hydroxy or $C_{1-6}$ alkoxy.

In certain embodiments, the in vivo imaging moiety is selected from $^{11}C$, $^{13}N$, $^{18}F$ and $^{124}I$.

In certain embodiments, $R^6$ is halogen.

In certain embodiments, $R^5$ is $C_{1-6}$ alkyl group.

In certain embodiments, $R^{11}$ is $C_{1-6}$ alkyl, $C_{1-6}$ haloalkyl, $C_{1-6}$ aminoalkyl comprising an in vivo imaging moiety.

In certain embodiments, the styrylbenzothiazole derivatives are compound of Formula VI:

Formula VI

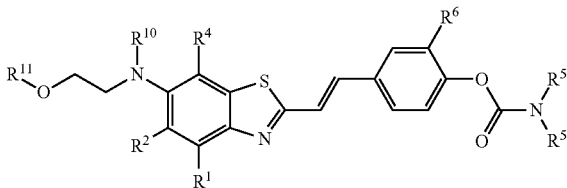

or a salt or solvate thereof, wherein:

$R^1$ and $R^4$ are each independently hydrogen, or an R group selected from, $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl; $R^2$ is hydrogen or $C_{1-6}$ alkyl; $R^5$ is, individually and independently at each occurrence, hydrogen, $C_{1-6}$ alkyl, $C_{2-6}$ alkenyl, or $C_{2-6}$ alkynyl; and $R^6$ is halogen, hydroxyl, $C_{1-6}$ alkoxy, $C_{1-6}$ alkyl, $C_{2-6}$ alkenyl, or $C_{2-6}$ alkynyl; $R^{10}$ is hydrogen or $C_{1-6}$ alkyl or an R group of formula VI, and $R^{11}$ is $C_{1-6}$ alkyl or an R group comprising an in vivo imaging moiety, such as $C_{1-6}$ haloalkyl, $C_{2-6}$ haloalkenyl, or $C_{2-6}$ haloalkynyl.

In certain embodiments, the in vivo imaging moiety is selected from $^{11}C$, $^{13}N$, $^{18}F$ and $^{124}I$.

In certain embodiments, $R^6$ is halogen.

In certain embodiments, $R^5$ is $C_{1-6}$ alkyl group.

In certain embodiments, $R^{11}$ is $C_{1-6}$ alkyl, $C_{1-6}$ haloalkyl, $C_{1-6}$ aminoalkyl comprising an in vivo imaging moiety.

Suitable salts according to the disclosure include (i) physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycolic, gluconic, succinic, methanesulfonic, and para-toluenesulfonic acids; and (ii) physiologically acceptable base salts such as ammonium salts, alkali metal salts (for example those of sodium and potassium), alkaline earth metal salts (for example those of calcium and magnesium), salts with organic bases such as triethanolamine, N-methyl-D-glucamine, piperidine, pyridine, piperazine, and morpholine, and salts with amino acids such as arginine and lysine.

Suitable solvates according to the disclosure include those formed with ethanol, water, saline, physiological buffer and glycol.

The term "alkyl" alone or in combination, means a straight-chain or branched-chain alkyl radical containing preferably from 1 to 6 carbon atoms, more preferably from 1 to 4 carbon atoms, preferably 1 to 3 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl.

The term "alkenyl" denotes an unsaturated straight-chain or branched aliphatic hydrocarbon group containing one double bond. Examples groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" denotes an unsaturated straight-chain or branched aliphatic hydrocarbon group containing one triple bond. Examples include groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Unless otherwise specified, the term "alkoxy", alone or in combination, means an alkyl ether radical wherein the term alkyl is as defined above. Examples of suitable alkyl ether radicals include, but are not limited to, methoxy, ethoxy, n-propoxy, isopropoxy, n-butoxy, iso-butoxy, sec-butoxy, tert-butoxy.

Unless otherwise specified, the term "cycloalkyl", alone or in combination, means a saturated or partially saturated monocyclic, bicyclic or tricyclic alkyl radical wherein each cyclic moiety contains preferably from 3 to 8 carbon atom ring members, more preferably from 3 to 7 carbon atom ring members, preferably from 4 to 6 carbon atom ring members, and which may optionally be a benzo fused ring system which is optionally substituted as defined herein with respect to the definition of aryl. Examples of such cycloalkyl radicals include, but are not limited to, cyclopropyl, cyclobutyl, cyclopentyl, cyclohexyl, cycloheptyl, octahydronaphthyl, 2,3-dihydro-1H-indenyl, adamantyl.

The term "hydroxyl" refers to a —OH group. The terms "hydroxyalkyl", "hydroxyalkenyl" and "hydroxyalkynyl", as used herein, refer to at least one hydroxy group appended to the parent molecular moiety through an alkyl, alkenyl, alkynyl, or alkoxy, respectively.

The term "halo" means a substituent selected from fluorine, chlorine, bromine or iodine. The terms "haloalkyl", "haloalkenyl", "haloalkynyl", "haloalkoxy" as used herein, refer to at least one halo group appended to the parent molecular moiety through an alkyl, alkenyl, alkynyl, or alkoxy, respectively. Preferred halo substituents are fluoro, bromo, and iodo.

The term "thiol" means an —SH group. The terms "thioalkyl, "thioalkenyl", "thioalkylnyl", "thioalkoxy" as used herein, refer to at least one thiol group appended to the parent molecular moiety through an alkyl, alkenyl, alkynyl, or alkoxy, respectively.

The term "cyano" as used herein refers to a —CN group. The terms "cyanoalkyl", "cyanoalkenyl", "cyanoalkynyl", "cyanoalkoxy" as used herein, refer to at least one cyano group appended to the parent molecular moiety through an alkyl, alkenyl, alkynyl, or alkoxy, respectively. Representative examples of cyanoalkyl include, but are not limited to, cyanomethyl, 2-cyanoethyl, and 3-cyanopropyl.

The term "nitro" means an —NO$_2$ group. The terms "nitroalkyl", "nitroalkenyl", "nitroalkynyl", "nitroalkoxy" as used herein, refer to at least one nitro group appended to the parent molecular moiety through an alkyl, alkenyl, alkynyl, or alkoxy, respectively.

The term "amino" means the group —NR$^9$R$^{10}$, wherein R$^9$ and R$^{10}$ are independently hydrogen or an R group as defined above for Formula I. The terms "aminoalkyl", "aminoalkenyl", "aminoalkynyl", "aminoalkoxy" as used herein, refer to at least one amino group appended to the parent molecular moiety through an alkyl, alkenyl, alkynyl, or alkoxy, respectively.

The term "carboxyl" means the group —COOH and the term "carboxyalkyl" refers to an alkyl group as defined herein wherein at least one carboxyl group is appended to the parent molecular moiety.

"Aryl" means aromatic rings or ring systems having 3 to 10 carbon atoms, and 5-10 members, in the ring system, e.g. phenyl or naphthyl. The term "heteroatom" refers to an N, S or O atom taking the place of a carbon in the ring system.

In a preferred embodiment, when said styrylbenzothiazole derivative is a compound of Formula I, said in vivo imaging agent is a compound of Formula II:

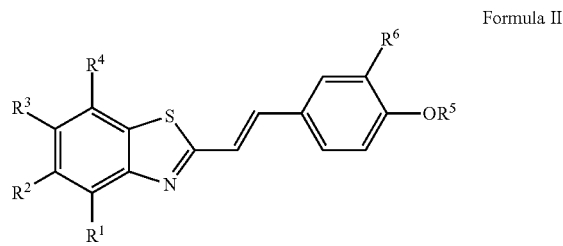

Formula II or a salt or solvate thereof, wherein:
each R$^1$-R$^4$, is independently hydrogen or an R group as defined above for Formula I, or comprises an in vivo imaging moiety as defined herein; and,
R$^5$ is hydrogen, C$_{1-6}$ carboxyalkyl, C$_{1-6}$ alkyl, or hydroxyl protecting group;
R$^6$ is halogen, hydroxyl, C$_{1-6}$ alkoxy, C$_{1-6}$ alkyl, C$_{2-6}$ alkenyl, or C$_{2-6}$ alkynyl.

In certain embodiments, R$^3$ is an amino group —NR$^9$R$^{10}$, wherein R$^9$ and R$^{10}$ are independently hydrogen or an R group as defined in Formula I, and R$^9$ comprises an in vivo imaging moiety as defined herein.

In certain embodiments, R$^5$ is hydrogen and R$^6$ is C$_{1-6}$ alkoxy or a halogen such as Br.

In certain embodiments, R$^3$ is an amino group —NR$^9$R$^{10}$, wherein R$^9$ and R$^{10}$ are independently hydrogen or an R group as defined in Formula I, or R$^9$ is an in vivo imaging moiety as defined herein, R$^{10}$ is hydrogen or an R group as defined in Formula I, and R$^2$ is C$_{1-6}$ alkyl.

In certain embodiments, at least one of R$^1$-R$^4$ comprises an in vivo imaging moiety as defined herein.

Mathis et al (J Med Chem 2003; 46: 2740-54) and Klunk et al (Ann. Neurol. 2004; 55: 306-19) describe synthesis of a particular $^{11}$C-labelled compounds; and Serdons et al (2006 J. Nuc. Med.; 47(Suppl.1): 31P) reports direct aromatic nucleophilic substitution of an $^{18}$F-atom for a nitro group to form an $^{18}$F-labelled compound. These reported methods can be easily adapted by the skilled person e.g. using known methods of labelling as described above, to obtain a range of in vivo imaging agents of Formula I. To obtain labelled versions of these compounds, straightforward application of known methods of introducing in vivo imaging moieties can be used, as described earlier.

Methods to obtain $^{99m}$Tc labelled in vivo imaging agents of Formula I are described in WO 02/1074347. The methods therein can be easily adapted using the above-described techniques for adding metal-chelate complexes and other in vivo imaging moieties to obtain further in vivo imaging agents suitable for use in the present disclosure.

Pharmaceutical Compositions

The in vivo imaging agent of the disclosure is preferably administered as a "pharmaceutical composition" which comprises said in vivo imaging agent, together with a biocompatible carrier, in a form suitable for mammalian administration.

The "biocompatible carrier" is a fluid, especially a liquid, in which the in vivo imaging agent as defined herein is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counter-ions), sugars (e.g. glucose or sucrose), sugar alcohols (e.g. sorbitol or mannitol), glycols (e.g. glycerol), or other non-ionic polyol materials (e.g. polyethylene glycols, propylene glycols and the like). The biocompatible carrier medium may also comprise biocompatible organic solvents such as ethanol. Such organic solvents are useful to solubilize more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

Such pharmaceutical compositions are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm volume) which contains multiple patient doses, whereby single patient doses can be withdrawn into clinical grade syringes at various time intervals during the viable lifetime of the preparation to suit the clinical situation. Pre-filled syringes are designed to contain a single human dose, or "unit dose", and are therefore preferably a disposable or other syringe suitable for clinical use. Where the pharmaceutical composition is a radiopharmaceutical composition, the pre-filled syringe may optionally be provided with a syringe shield to protect the operator from radioactive dose. Suitable such radiopharmaceutical syringe shields are known in the art and preferably comprise either lead or tungsten.

The pharmaceutical composition may be prepared from a kit. Alternatively, it may be prepared under aseptic manufacture conditions to give the desired sterile product. The pharmaceutical composition may also be prepared under non-sterile conditions, followed by terminal sterilization using e.g. gamma-irradiation, autoclaving, dry heat or chemical treatment (e.g. with ethylene oxide).

Diagnosis and Treatment Monitoring

The protein α-synuclein is found in healthy nerve cells as an unfolded membrane-bound protein. In response to pathological stimuli during the pathophysiology of a synucleinopathy, α-synuclein detaches from the membrane and takes on a β-sheet conformation, leading to aggregation and formation of LB and LN. A "synucleinopathy" is a neurodegenerative disease characterized by the presence of α-synuclein deposits in the neurons and the glia. Parkinson's disease (PD), dementia with Lewy bodies (DLB) and multiple system atrophy (MSA) are known examples of synucleinopathies. It has been postulated that α-synuclein deposits are present in the ANS in the early stages of PD (Braak et al J. Neural Transm. 2003; 110: 517-36), and as such the method of the present disclosure is useful in the early diagnosis of PD.

The present disclosure therefore also provides a method for the determination of the presence of, or susceptibility to, PD, said method as described above in relation to the in vivo imaging agent of the disclosure. Early diagnosis of PD, or of a susceptibility to PD, is advantageous as the disease process can be treated at early stage and treat disease before the onset of symptoms. Currently there is no such early diagnostic method such that by the time of diagnosis the patient has lost the majority of the nigrostriatal neurons controlling motor function, and application of neuroprotective agents is only beneficial for the remaining nigrostriatal neurons.

In a yet further aspect, the method of the present disclosure as described herein may be performed repeatedly, each performance being at a temporally distinct point in time, and wherein the images obtained in step (iv) are compared. Such a method is useful in monitoring the progression of PD. In a preferred embodiment, the method is performed before, during and/or after implementation of a treatment regimen, in order to determine the effectiveness of said treatment regimen.

In another aspect, the present disclosure provides a styryl-benzothiazole derivative as defined herein for use in the preparation of an in vivo imaging agent for use in any of the methods defined herein.

In a further aspect, the present disclosure provides an in vivo imaging agent as defined herein for use in the manufacture of a medicament suitable for use in either the method of diagnosis, or the method of treatment monitoring as described above.

EXAMPLES

Screening Hit Identification and Optimization

A selective Lewy body PET (positron emission tomography) tracer has been synthesized that specifically recognizes aggregated α-Syn but not Aβ or Tau deposits. Employing several cycles of counter-screenings with in vitro fibrils, intra-neuronal aggregates, neurodegenerative diseases' brain sections from various animal models and patients, a benzothiazole-vinylphenol derivative was synthesized that distinctively diagnoses A53T α-Syn Lewy bodies but not senile plaques or Neurofibrillary tangles (NFT) in numerous animal models using microPET. [$^{18}$F]F0502B showed a high binding affinity for synthetic α-Syn but not Aβ or Tau fibrils, preferential binding to dense α-Syn granular cores in brain sections, and excellent brain uptake and rapid clearance in mice. Therefore, [$^{18}$F]F0502B is a promising agent for imaging Lewy bodies in Synucleinopathies.

A series of derivatives were screened and synthesized, and performed in vitro α-Syn, Aβ and Tau fibrils binding assays. The top structural backbones were further optimized via organic synthesis, followed by counter-screenings using in vitro fibrils, in primary neurons with these aggregates, binding assays with brain sections containing Lewy bodies, Aβ-enriched senile plaques and NFT (neurofibrillary tangles) with hyperphosphorylated and truncated Tau as the major components. The top candidates' in vivo pharmacokinetics (PK) and brain exposures were compared. Finally, a novel benzothiazole-vinyl-phenol derivative (F0502B) was obtained. [$^{18}$F]fluorinated Lewy body imaging compound of F0502B specifically recognized α-Syn versus Aβ and Tau fibrils in vitro and in vivo. It selectively labeled Lewy bodies in A53T α-Syn PD mice but not senile plaques or NFT in 3×Tg, 5×FAD or Tau P301S mice. It displayed barely detectable signals in the brain of wild-type C57BL/6J mice.

The general strategy that was employed to screen the candidate Lewy body PET agents is summarized as follows: (a) To perform in vitro binding assay with Pre-formed fibrils (PFFs) of α-Syn and counter-screening with Tau and Aβ PFFs; (b) To test the positive compounds in the neuronal models with aggregated α-Syn, Tau or AD; (c) To screen with the brain slides from α-Syn mutant A53T virus injected WT mice, and counter-screen with aged 3×Tg (containing both senile plaques and NFT), and aged Tau P301S (NFT) brain sections; (d) to screen the patient brain sections from DLB and MSA against AD; (e) To determine the binding kinetics between α-Syn PFFs and positive hits; (f) To determine the candidates in vivo brain/plasma (B/P) ratios and the brain permeability; (g) To determine the in vivo PET images in α-Syn A53T with candidates and compare its images in 5XFAD and Tau P301S mice.

Figure 7A:
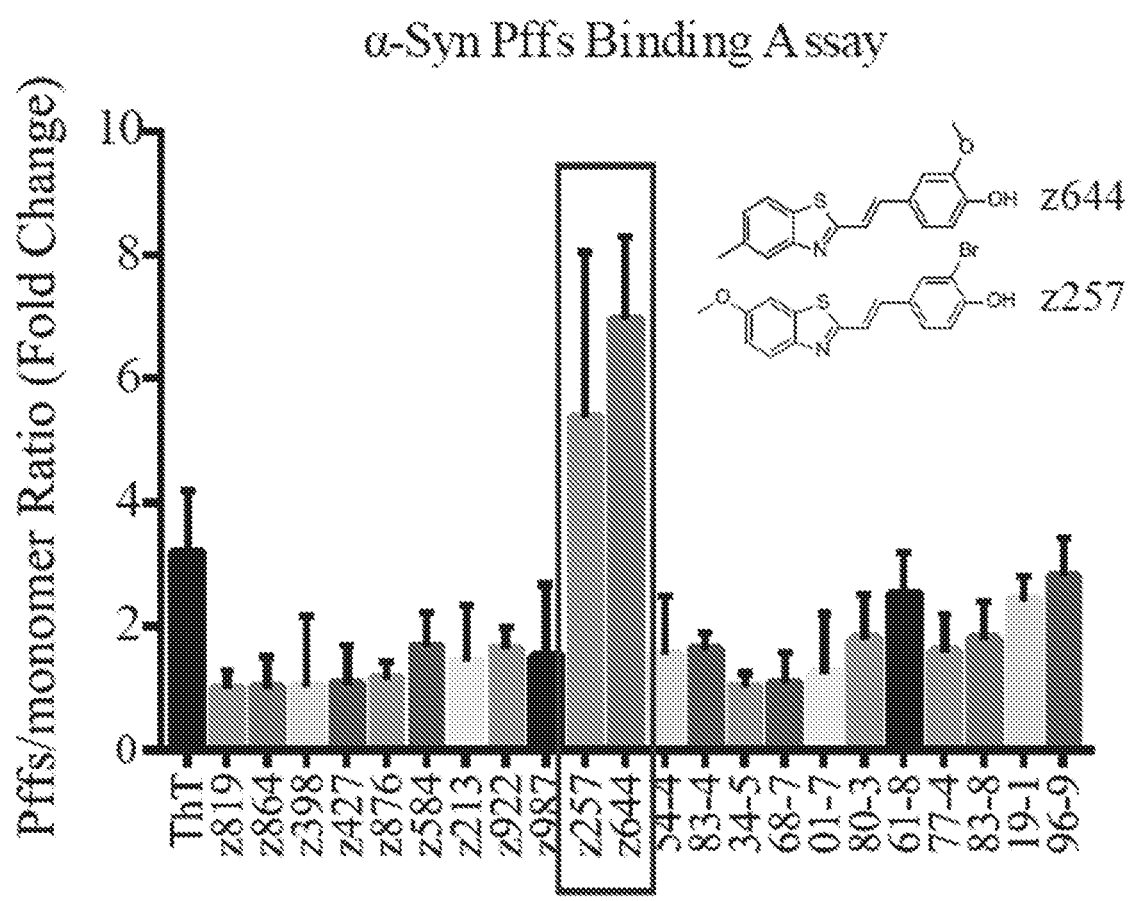
FIG. 7A shows data on screening candidate compounds with α-Syn Pff binding assay by using spectrophotometric assay.
Figure 7B:
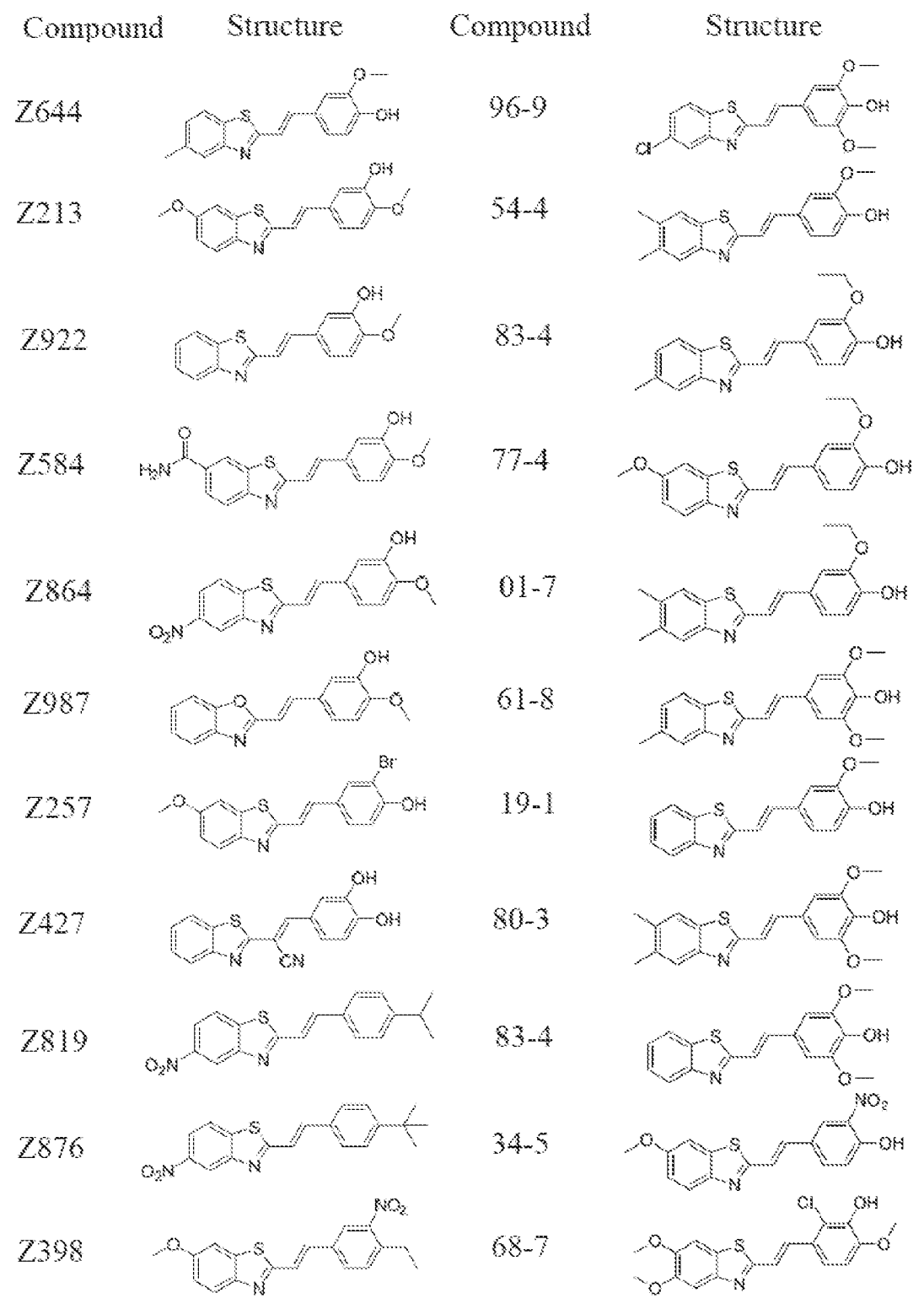

To perform in vitro binding assay, commercial compounds were screened (See FIG. 7B). The summary of the binding activities toward α-Syn fibrils and positive control ThT was depicted in FIG. 7A, and both z644 and z257 displayed most robust binding activities toward α-Syn PFFs. Counter-screening revealed that both of them exhibited much higher binding effects toward α-Syn than Aβ or Tau PFFs, whereas ThT non-selectively interacted with these PFFs. Quantification revealed that both z644 and z257 showed much weaker binding effects toward Aβ or Tau PFFs.

Figure 2A:
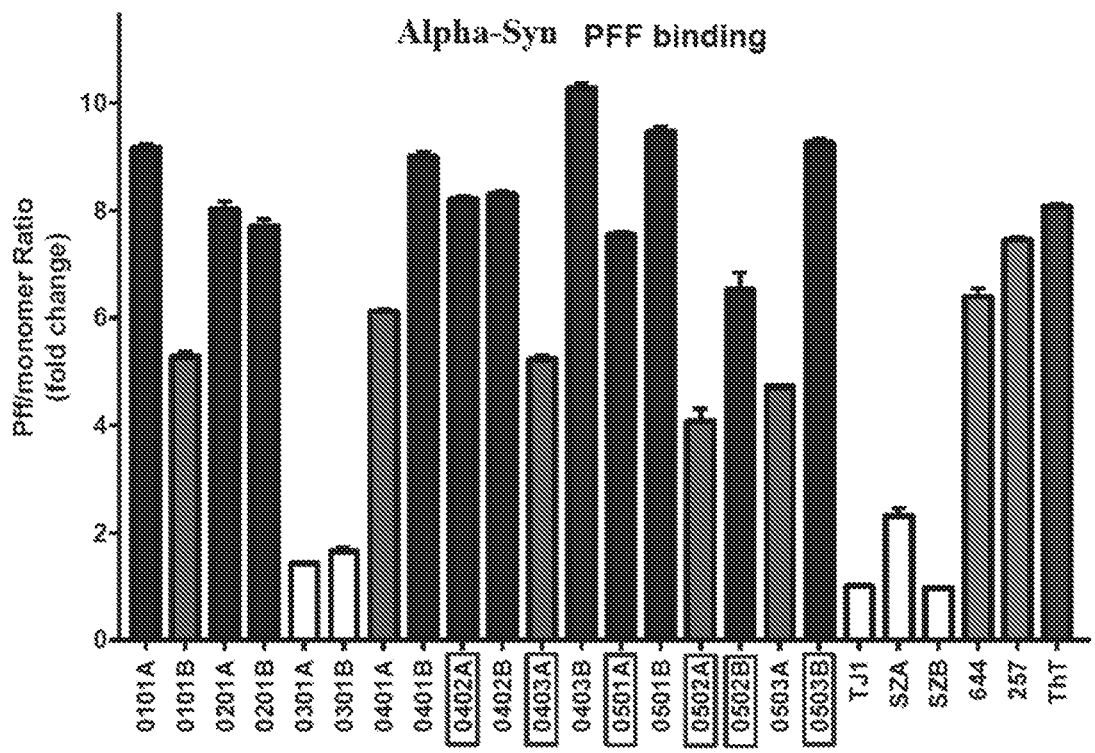
FIG. 2A shows binding data or compounds disclosed herein for Alpha-Syn PFFs.

A series of derivatives were synthesized by including an amino group and a methyl group on benzothiazole to increase the brain permeability and fluorescent signals. The derivatives were subsequently subjected to α-Syn PFFs binding assay and counter-screening with Tau and Aβ PFFs. Compounds that displayed noticeable α-Syn PFFs binding effect but modestly associated with Aβ or Tau PFFs are highlighted in the red box (FIG. 2A). These compounds were screened on the neuronal α-Syn, Tau and Aβ aggregation model for the binding selectivity. Primary cultured neurons were infected with AAV-α-Syn, AAV-Tau FL for 7 days, then treated with α-Syn, Tau or Aβ PFFs. In a few days, the positive compounds were added in the primary neurons with indicated aggregates and analyzed under fluorescent microscopy. Of these tested compounds, EU04-03A, EU05-02A and EU05-02B selectively yielded the positive signals in α-Syn aggregated neurons but negligible effects in neurons with Aβ or Tau aggregates.

Screen the Positive Compounds on the Brain Slides with Lewy Bodies

To further explore whether the positive compounds selectively bind to the Lewy bodies, α-Syn A53T patient-derived mutant virus injected WT mice brain slices were employed. These mice display extensive Lewy bodies in the SN. Moreover, NFT abundant Tau P301S mice, A3-enriched 5×FAD and 3×Tg mice that possess both were utilized. The Lewy bodies were labeled with p-α-Syn S129 antibody and the concrete aggregates were also stained with the fluorescent signals from EU05-02B, which barely recognized senile plaques or NFT. As a positive control, ThT co-localized with all of these aggregates in the brain sections. Other compounds displayed weak signals toward Lewy bodies, though none of the tested compounds were reactive with NFT. However, both z257 and z644 associated with senile plaques.

Ex vivo screening was extended into human DLB, MSA and AD patient samples. EU05-02B showed robust signals with LBs and LNs in DLB and MSA patient brains but did not stain senile plaques or NFT in AD. Other compounds including EU04-03A and EU05-02A etc also co-stained with Lewy bodies and barely recognized AT8 positive Tau NFT or Aβ aggregates in AD brains. Since there are detectable α-Syn aggregates in AD patient brains, these compounds colocalized with p-S129 positive α-Syn inclusions. Based on these data, several compounds were selected for further interrogation.

Optimized EU05-02B (F0502B) Selectively Binds to Lewy Bodies

To address whether the selected compounds penetrate the brain, a plasma-brain ratio study was performed with EU04-03A, EU05-02A and EU05-02B. Strikingly, both EU04-03A and EU05-02B swiftly penetrated the brain and exhibited much higher brain permeability compared to EU05-02A. Though EU04-03A displayed higher brain permeability than EU05-02B, considering the specificity toward α-Syn versus Aβ and Tau, and in vivo half-life for rapid brain clearance for a potential PET tracer, EU05-02B was chosen for further in vivo imaging assays.

A fluorescent titration assay was conducted. The fluorescent emission intensities were determined with 0.08 μM of various fibrils in the presence of 5 μM of the small molecules. EU-05-02B but not EU-05-02A and EU-04-03A showed specific association with the PFFs. Fluorescent binding assay revealed that EU05-02B displayed partial binding selectivity toward α-Syn PFFs versus Aβ and Tau fibrils. Since $^{18}$F possesses much longer half-life and is much more favorable than 11C for clinical PET usage, the N-methyl group on EU05-02B was label using an N-2-(2-fluoroethoxy)ethyl-N-methyl group. Notably, F0502B specifically associated with α-Syn fibrils but barely bound to Aβ or Tau fibrils. Neuronal culture binding and Lewy body staining from the brain sections of A53T PD mice and MSA and DLB patients validated F0502B specifically associated with α-Syn aggregates but not senile plaques or NFT from 5×FAD, 3×Tg and Tau P301S mice or AD patients.

F0502B In Vivo PK Study and B/P Ratios

To ensure that F0502B meets a PET tracer's kinetic criteria with rapid penetration into the brain and swift wash out, an in vivo PK study was performed in mice with i.v. injection of 5 mg/kg of F0502B. The half-life of F0502B was t1/2=1.16 h with Cl rate approximately 3.92 L/h/kg. It was almost completely decayed at 8 h in the plasm. Remarkably, F0502B swiftly entered the brain and accumulated in the brain compared to the plasma. Quantification of F0502B concentrations in the brain versus plasma showed that the B/P ratios increased from 4.16 at 0.5 h to 13.37 at 1 h and climaxed with 25.96 at 4 h.

F0502B was preferentially enriched in the brain. F0502B (5 mg/kg) was administrated via i.v. injection into mice infected with viral A53T in PD mice, 5XFAD and Tau P301S mice and age-matched control mice (8 months old). In 2 h, the mice were sacrificed and stained the mouse brain sections with anti-Aβ, AT8 and p-S129 and ThS, respectively. As negative control, WT mice did not reveal any anti-AD, AT8 and p-S129 co-staining signals for F0502B or ThS. By contrast, the aggregated Lewy bodies stained by anti-p-S129 were colocalized with both F0502B and ThS. Nevertheless, the senile plaques in 5×FAD mice and 3×Tg mice and NFT in 3×Tg and Tau P301S mice were robustly stained by ThS but not F0502B. Hence, these in vivo data with F0502B support that F0502B selectively stains the Lewy bodies that are positive with anti-p-α-Syn S129 in A53T PD mouse model, but it does not co-stain Aβ or Tau aggregates that are positive for ThS in various AD mouse models.

18F-Labeled Synthetic Route for Radiochemistry

Figure 4:
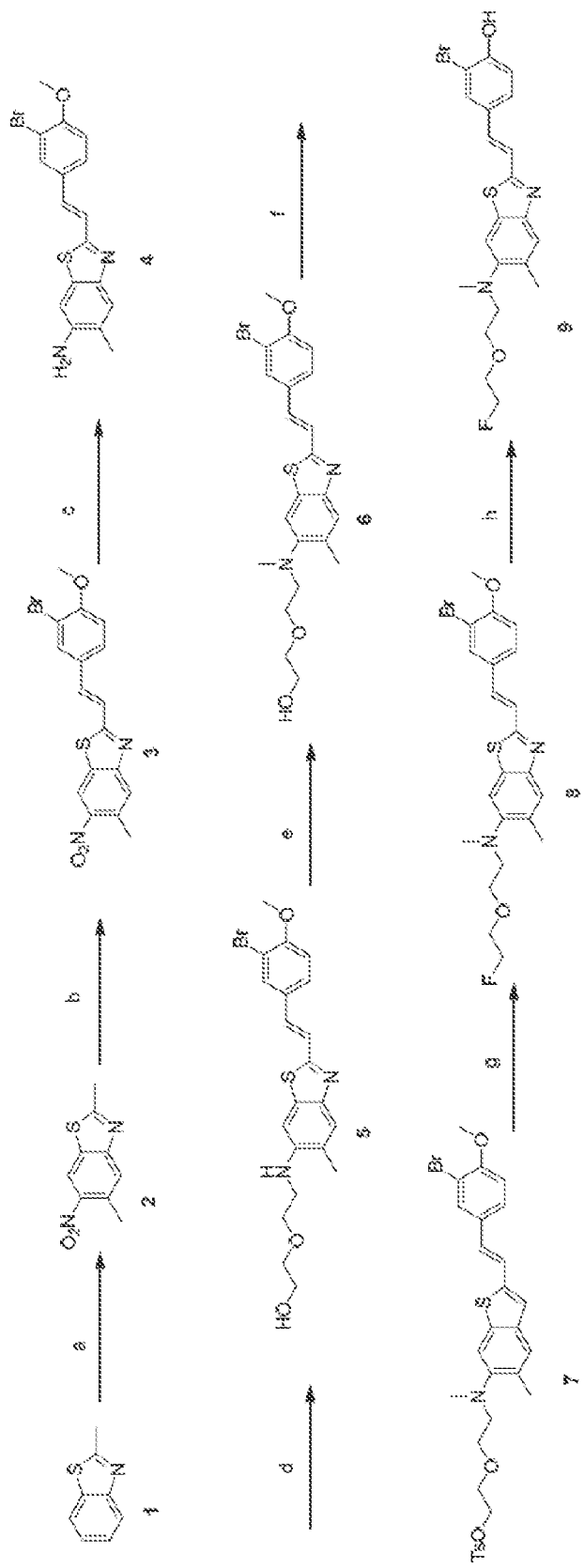
FIG. 4 illustrates the synthesis of compounds disclosed herein. Reagents and conditions: (a) HNO$_3$, H$_2$SO$_4$, 0° C.-rt; (b) 3-bromo-4-methoxybenzaldehyde, H$_2$SO$_4$, dioxane, 100° C.; (c) Fe, NH$_4$Cl, MeOH, 80° C.; (d) 2-(2-iodoethoxy) ethanol, K$_2$CO$_3$, DMF, 85° C.; (e) MeI, K$_2$CO$_3$, DMF, 30° C.; (f) TsCl, TEA, DCM, rt; (g) KF/Kryptofix® 222, CH$_3$CN, 60° C.; (h) EtSNa, DMF, 100° C.
Figure 5A:
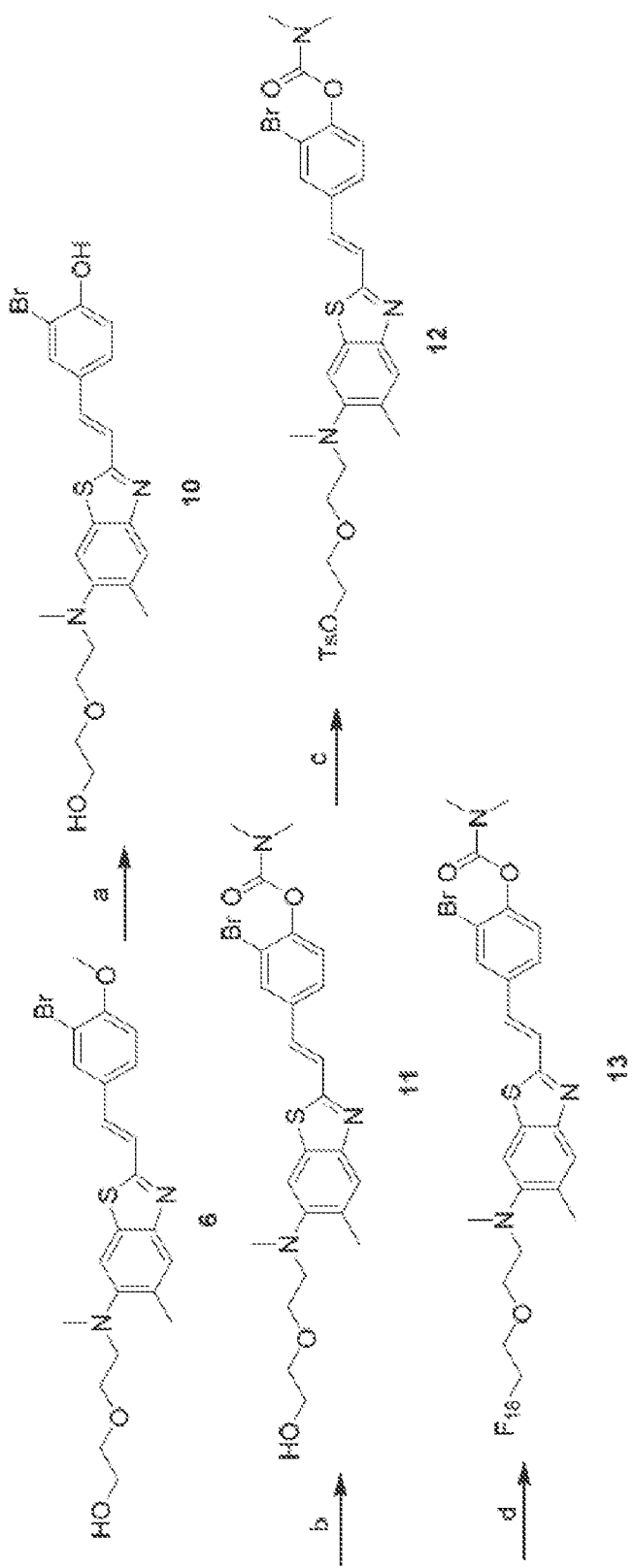
FIG. 5A illustrates the synthesis of compounds disclosed herein. Reagents and conditions: (a) EtSNa, DMF, 130° C.; (b) dimethylcarbamoyl chloride, K$_2$CO$_3$, CH$_3$CN, 90° C.; (c) TsCl, TEA, DCM, rt; (d) KF/Kryptofix® 222, CH$_3$CN, 60° C.
Figure 5B:
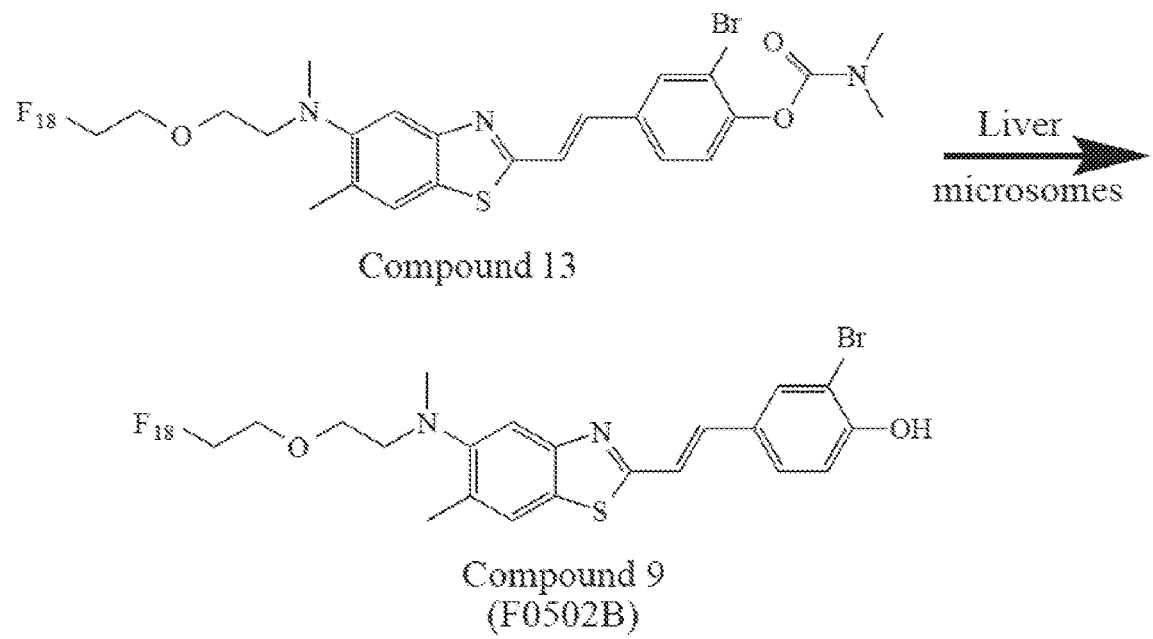
FIG. 5B illustrates compound 13 decaying into F0502B.
Figure 5C:
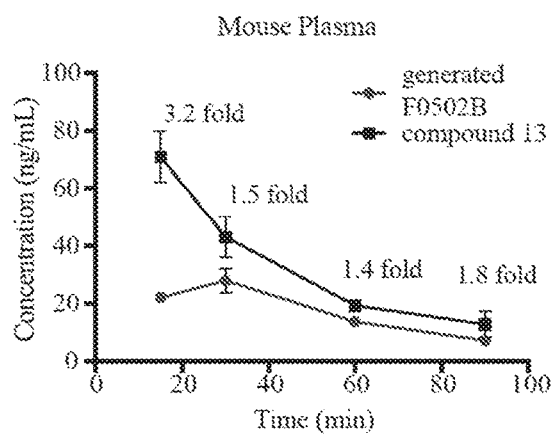
FIG. 5C shows in vivo PK study of Compound 13 decaying into F0502B in Tg mice with compound 13. Data indicates compound 13 and generated F0502B concentrations in mice plasma after injection compound 13 from 15 min to 90 min.
Figure 5D:
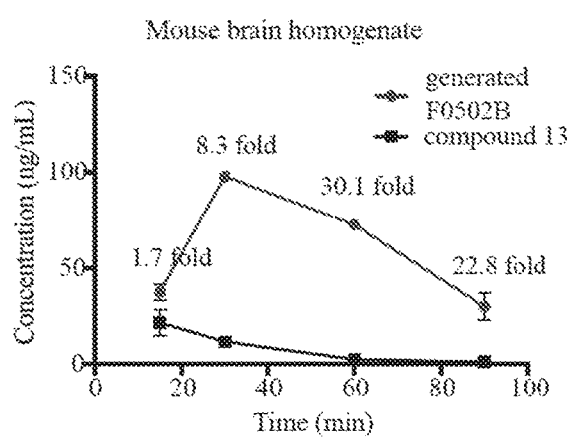
FIG. 5D shows data on compound 13 and generated F0502B concentrations in mice brain after injection compound 13 from 15 min to 90 min.
Figure 5E:
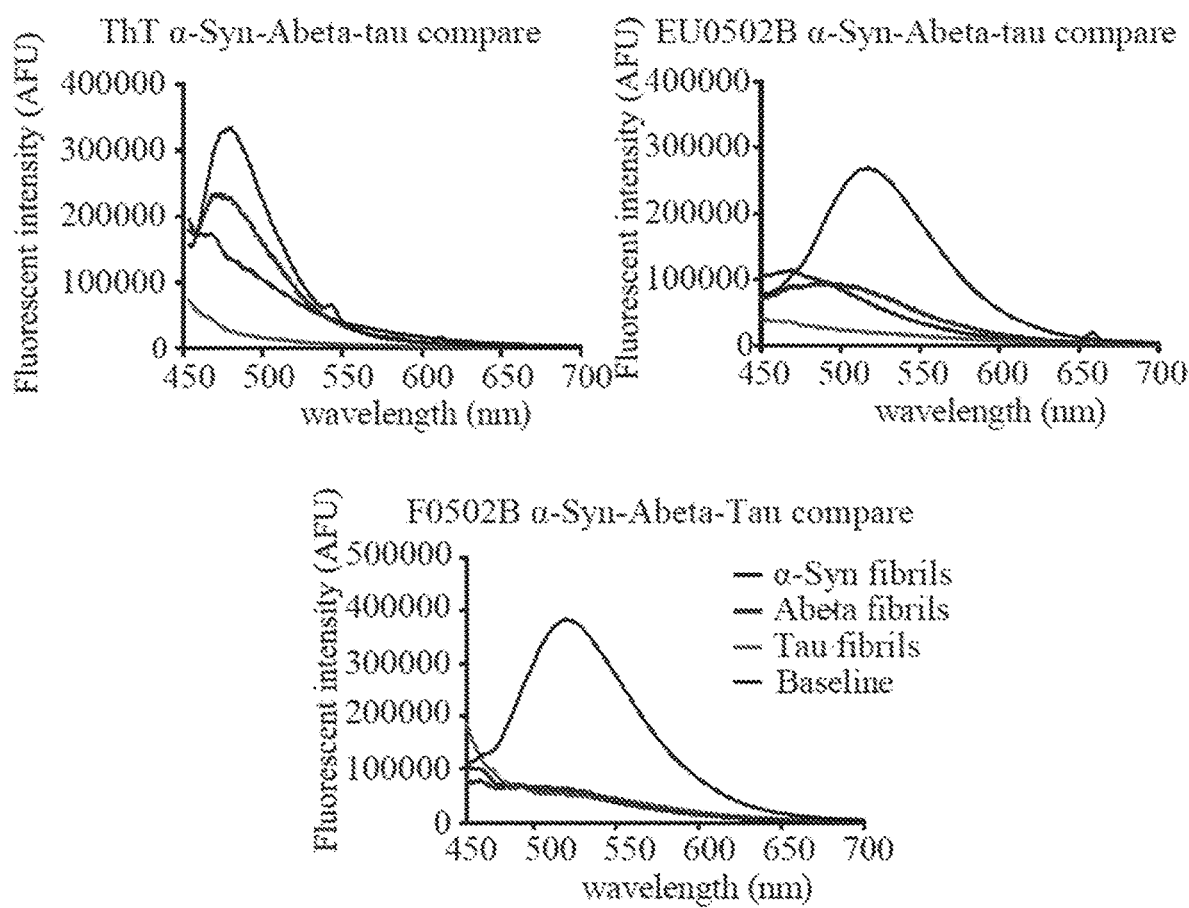
FIG. 5E shows data on quantification of binding affinities demonstrated that ThT and EU05-02B binding with α-Syn.
Figure 6A:
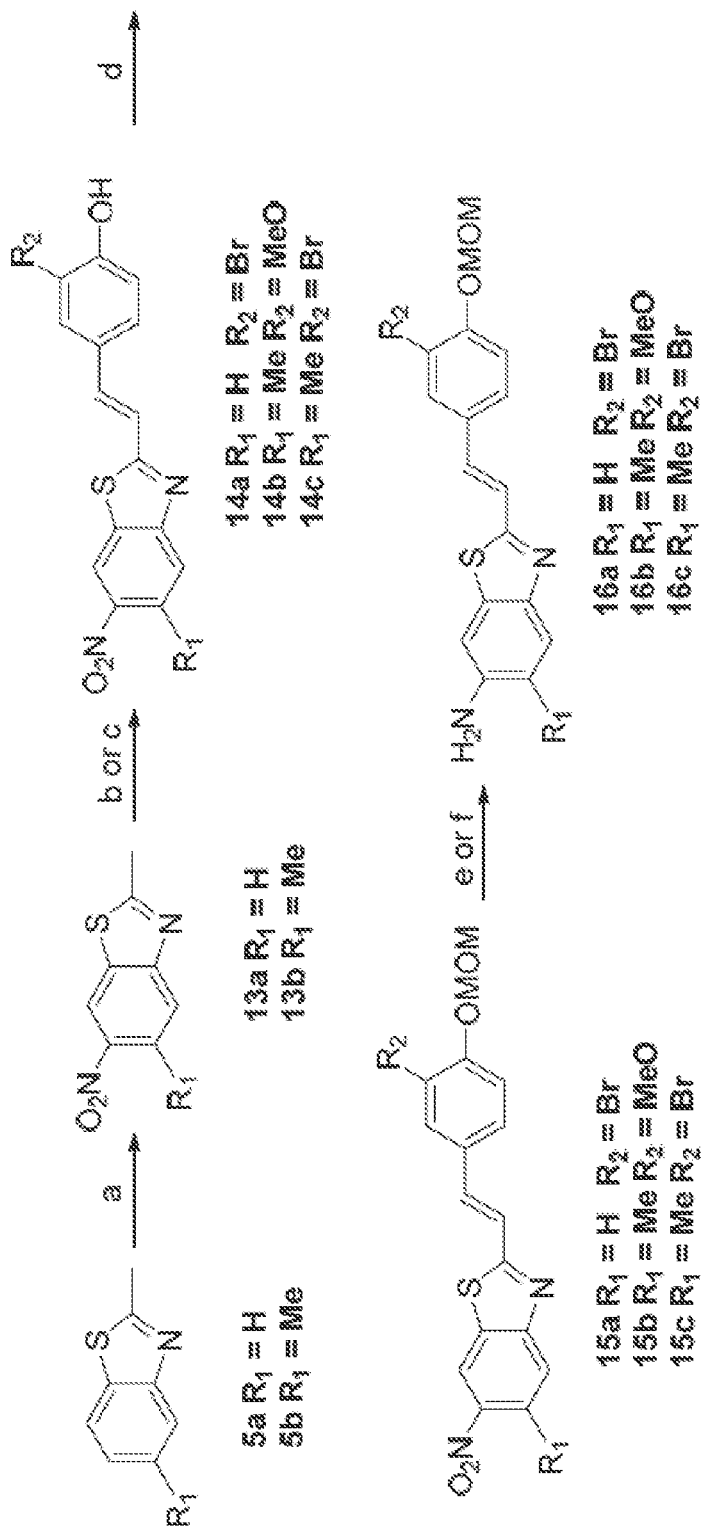
FIG. 6A illustrates the preparation of compounds disclosed herein. Reagent and conditions: (a) HNO₃, H₂SO₄, 0° C.-rt; (b) (for 14a,c) H₂SO₄, dioxane, 1b, rt; (c) (for 14b) H₂SO₄, dioxane, 1a, rt; (d) MOMBr, TEA, DCM, rt; (e) (for 16a and 16b) Zn, NH₄Cl, EtOH, rt; (f) (for 16c) Zn, NH₄Cl, MeOH, rt.
Figure 6B:
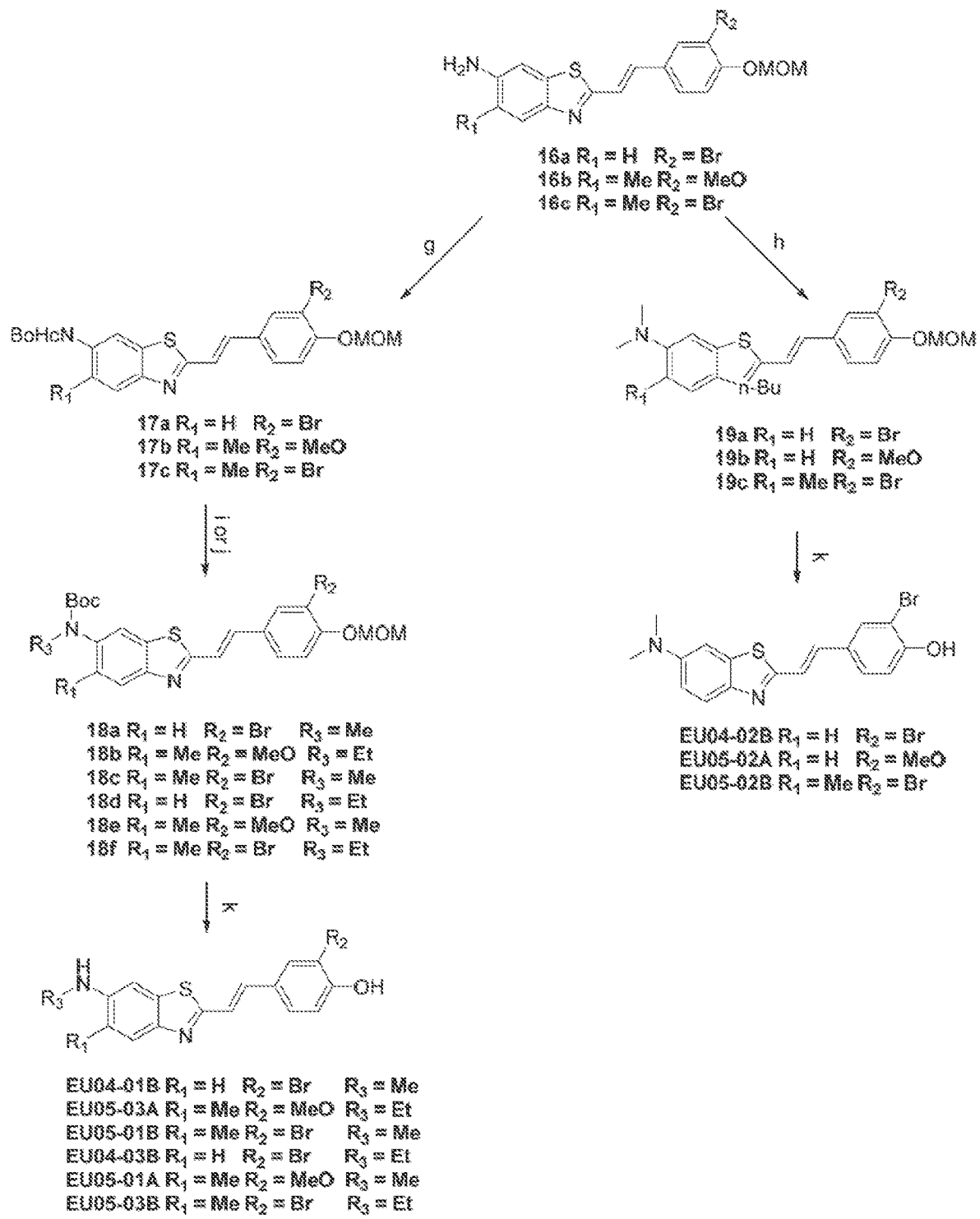
FIG. 6B illustrates the preparation of compounds disclosed herein. Reagent and conditions: (g) Boc₂O, 60° C.; (h) aq. HCHO, NaBH₃CN, 0° C.; (i) (for 18a, 18c and 18e) MeI, NaH, 0° C.; (j) (for 18b, 18d and 18f) EtI, NaH, 0° C.; (k) TFA, 0° C.

Preliminary data indicates that F0502B selectively associates with Lewy bodies but not Aβ or NFT aggregates in vitro or in vivo. To further characterize this promising putative PET tracer, an $^{18}$F-labeled synthetic route was developed. Since the phenol group is labile during fluorination, a TsO— was employed to replace the methoxy phenyl precursor. The F-labeled compound 8 was subsequently demethylated with EtSNa into F0502B (compound 9) (FIG. 4). Alternatively, an N,N,-dimethylcarbamate protected prodrug (compound 13) was synthesized (FIG. 5A). TsO-replaced precursor (compound 12) was readily fluorinated with KF, yielding F-labeled compound 13. In vitro liver microsomes hydrolysis assay revealed that compound 13 transformed into F0502B with more than 90% of yield after 1 h incubation (FIG. 5B). To ascertain that compound 13 could swiftly decay into F0502B in mice, an in vivo PK study was conducted. Compound 13 was decreased in the plasma, and F0502B was concomitantly escalated at 30 min and subsequently declined (FIG. 5C). By contrast, the newly generated F0502B expeditiously augmented in the brain with a peak at 30 min (FIG. 5D).

Fibrils binding assay showed that compound 13 did not specifically interact with α-Syn, Aβ or Tau aggregates, alleviating the concerns that the remnant compound 13 in the brain might interfere with F0502B imaging signals, though compound 8 somehow interacted with both α-Syn and Aβ but not Tau fibrils. Two hours after tail injection of 2 mg/kg of compound 13 into various animal models showed that brain generated F0502B selectively stained Lewy body in A53T mice but not senile plaques or NFT in various AD mouse models. The p-S$_{129}$ positive Lewy bodies in A53T PD mice were further confirmed by anti-aggregated α-Syn 5G2 antibody.

Quantification of F0502B Interaction with α-Syn Fibrils Versus Aβ and Tau Fibrils

[$^{18}$F]F0502B was evaluated in vitro and ex vivo binding assays to validate its specificity. α-Syn, Tau and Aβ PFFs were respectively incubated with increasing concentrations of [$^{18}$F]F0502B. The binding data were analyzed by curve fitting using nonlinear regression to obtain Kd and Bmax values. The Kd and a Bmax manifested the specific binding affinity with different fibrils. The affinity of [$^{18}$F]F0502B for AD 1-42 or Tau fibrils was much lower than that for α-Syn fibrils. A competitive binding assay utilizing fixed concentrations of α-Syn fibrils and [$^{18}$F]F0502B showed [$^{18}$F]F0502B was selectively stripped off by increasing concentrations of cold F0502B but not EU03-01B. To determine whether a binding site identified on recombinant α-Syn fibrils is also present in PD tissues, and to determine whether the density of binding sites is high enough to image fibrillar α-Syn in vivo, experiments on the binding of [$^{18}$F]F0502B to LBD, AD patient and control brain homogenates were conducted as well as extracted α-Syn, Tau and Aβ insoluble fibrillar fractions prepared from these samples, Kd and Bmax values for the PD cases were 37.47 nM and 14.3 pmol/nmol. In contrast, the Kd and Bmax values for Aβ fibrils in AD cases were 950.4 nM and 10.8 pmol/nmol and for Tau fibrils in AD cases were 1883 nM and 6.9 pmol/nmol. These results indicate that [$^{18}$F]F0502B binding affinity in LBD or PD brains is comparable to the binding affinity for recombinant α-Syn fibrils. Autoradiography with [$^{18}$F]F0502B in human brain slices was performed. [$^{18}$F]F0502B selectively associated with the Lewy bodies in the brain sections from A53T PD mice but not in WT and AD transgenic mice. Further, [$^{18}$F]F0502B selectively associated with the Lewy bodies in the brain sections from LBD but not AD patients. The binding activities were blocked by excessive cold F0502B. Together, these findings support that F0502B specifically and tightly binds to α-Syn fibrils in the Lewy bodies.

The biodistribution of [$^{18}$F]F0502B in mice was monitored. Two hours after tail vein injection of [$^{18}$F]-compound 13 precursor into different strains of mice, a variety of organs were collected from the mice. The tissues were weighted. The radio-activities versus wet tissue weight was determined. While most of the radioactive materials were distributed in the livers or kidneys, demonstrable radioactive PET tracers were selectively enriched in the brains from A53T than wild-type, 5×FAD and Tau P301S mice, fitting with the in vivo PK findings that F0502B is brain permeable.

[$^{18}$F]F0502B Specificity in A53T PD and 5XFAD and Tau P301S Mice.

To assess the performance of the developed PET tracer in a rodent PD model, microPET-CT imaging was performed in mice by the tail vein injection of [$^{18}$F]F0505B. Brain images were obtained 1 h after administration of radioactive PET Tracer in a A53T PD model. Aged wild-type and 5XFAD mice that possess extensive senile plaques and Tau P301S mice that contain strong NFT for comparison were employed as a control. The mice were anesthetized using isoflurane and positioned in a prone position in the microPET-CT scanner with the brain in the field of view.

Following the acquisition of a CT attenuation correction scan, the mice were injected with the [$^{18}$F]-compound13 via the tail vein. Image voxel intensities represent absolute tracer concentration in units of μCi/ml. Remarkably, [$^{18}$F] F0502B PET tracer specifically lighted up the Lewy body in the SN regions in A53T PD mice; by contrast, no signals were observed in WT or Tau P301S mice, fitting with its weak binding affinity to aggregated Tau fibrils. Though radioactive signals were found in the neck of 5×FAD mice, they were outside the brain. This data indicates [$^{18}$F]-compound 13 can be used as a specific Lewy body PET tracer for diagnosing synucleinopathies.

Synthesis of Compounds

Schemes for preparing compounds are provide for in FIGS. 1G, 1H, 1I, 1J, 3, 4, and 5.

3-methoxy-4-((tetrahydro-2H-pyran-2-yl)oxy)benzaldehyde (2a)

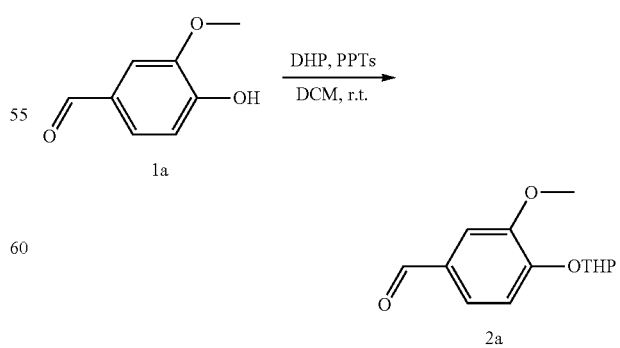

To a solution of 4-hydroxy-3-methoxybenzaldehyde 1a (10 g, 65.8 mmol) in $CH_2Cl_2$ (100 mL) was added 3,4- dihdro-2H-pyrane (16.8 g, 200 mmol) and pyridinium para-toluenesulfonate (5.78 g 0.23 mmol) at room temperature. The reaction mixture was stirred at room temperature overnight, then quenched with saturated Na$_2$CO$_3$ aqueous solution (100 mL). The organic layer was separated, washed with brine (50 mL), dried over anhydrous Na$_2$SO$_4$, filtered and concentrated. The residue was purified by silica gel column chromatography using 15% ethyl acetate in petroleum ether as eluent to give 2a as a brown oil (4.7 g, 26% yield). MS (ESI) m/z 237.0 [M+H]$^+$.

3-bromo-4-(methoxymethoxy)benzaldehyde (2b)

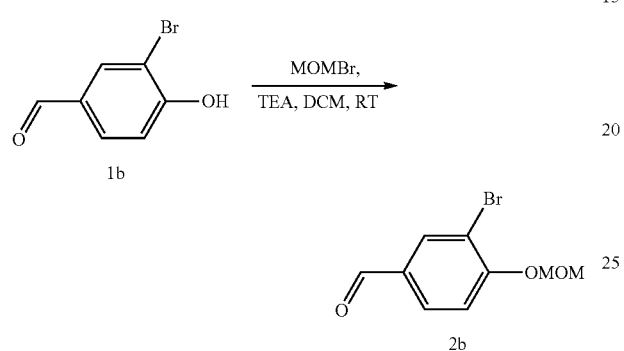

To a solution of 3-bromo-4-hydroxybenzaldehyde 1b (10.9 g, 59.9 mmol) in CH$_2$Cl$_2$ (150 mL) was added triethylamine (10.1 g, 100 mmol) and methoxymethyl bromide (9.37 g, 75.9 mmol) at 0° C. under nitrogen. The reaction mixture was stirred at room temperature for 2 h then washed with saturated NaHCO$_3$ aqueous solution (3×50 mL) and brine (2×50 mL). The organic portion was dried over anhydrous Na$_2$SO$_4$, filtered and concentrated to give 2b as a yellow oil (10.8 g, 89% yield). $^1$H NMR (400 MHz, CDCl$_3$): δ 9.86 (s, 1H), 8.09 (d, J=2.0 Hz, 1H), 7.79 (dd, J=8.4, 2.0 Hz, 1H), 7.27 (d, J=8.4 Hz, 1H), 5.35 (s, 2H), 3.53 (s, 3H); MS (ESI) m/z 244.8 and 246.8 [M+H]$^+$.

3-methoxy-4-methoxymethoxy)benzaldehyde (2c)

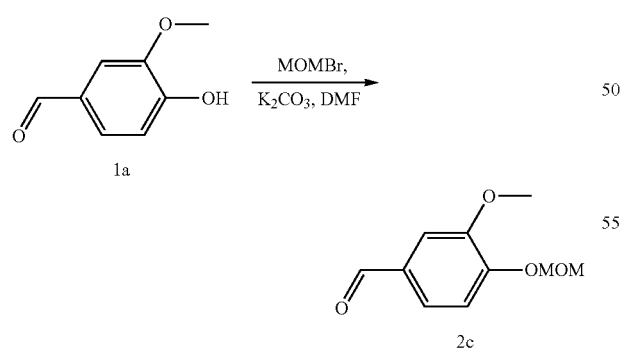

To a solution of 4-hydroxy-3-methoxybenzaldehyde 1a (20 g, 0.13 mol) in DMF (100 mL) was added K$_2$CO$_3$ (36 g, 0.26 mmol) and methoxymethyl bromide (33 g, 0.26 mmol) at 0° C. under nitrogen. The reaction mixture was stirred 60° C. for 3 h. After cooling down to room temperature, the reaction mixture was poured into water (200 mL) and extracted with ethyl acetate (3×100 mL). The combined organic layers were washed with brine (3×100 mL), dried over anhydrous Na$_2$SO$_4$, filtered and concentrated to give 2c as yellow oil (10.3 g, 40% yield). $^1$H NMR (400 MHz, CDCl$_3$): δ 9.88 (s, 1H), 7.45-7.43 (m, 2H), 7.30-7.27 (m, 1H), 5.34 (s, 2H), 3.96 (s, 3H), 3.53 (s, 3H); MS (ESI) m/z 196.9 [M+H]$^+$.

(E)-2-(3-methoxy-4-((tetrahydro-2H-pyran-2-yl)oxy)styryl)benzo[d]thiazole (3a)

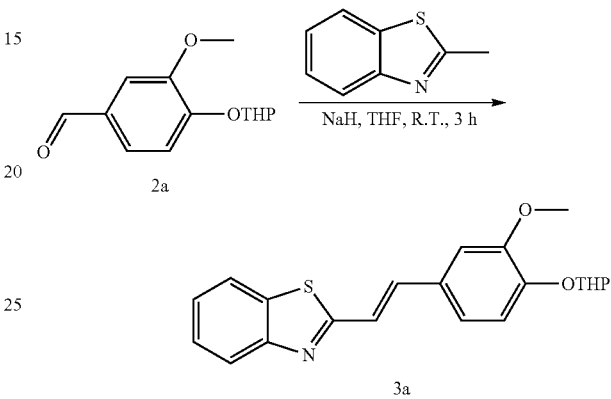

To a suspension of sodium hydride (306 mg, 7.65 mmol) in anhydrous THF (15 mL) was added 2-methylbenzothiazole (500 mg, 3.4 mmol) at 0° C. under nitrogen. The reaction mixture was stirred at room temperature for 1 h before 2a (875 mg, 3.74 mmol) was added. The reaction mixture was stirred at room temperature for another 3 h. Water (10 mL) was added and the mixture was extracted with ethyl acetate (3×20 mL). The organic layers were combined and washed with brine (10 mL), dried over anhydrous Na$_2$SO$_4$, filtered and concentrated. The residue was purified on a automated flash chromatography system (with a gradient of 50-95% of acetonitrile and water over 15 min at a flow rate of 40 mL/min) to give 3a as a yellow solid (570 mg, 46% yield). MS (ESI) m/z 368.0 [M+H]$^+$.

(E)-2-(3-bromo-4-(methoxymethoxy)styryl)benzo[d]thiazole(3b)

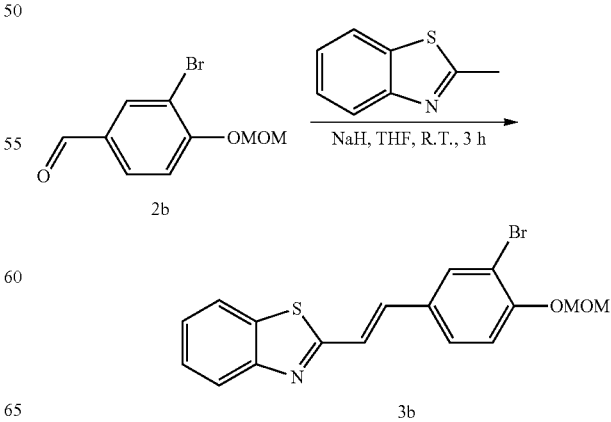

To a suspension of sodium hydride (298 mg, 7.46 mmol) in anhydrous THF (20 mL) was added 2-methylbenzothiazole (556 mg, 3.73 mmol) at 0° C. under nitrogen. The reaction mixture was stirred at 0° C. for 3 h before 2b (1.0 g, 4.10 mmol) was added. The reaction mixture was stirred at room temperature for another 3 h. Water (2 mL) was added to quench the reaction. The mixture was concentrated and the residue was purified on a automated flash chromatography system (with a gradient of 20-95% of acetonitrile and water over 15 min at a flow rate of 40 mL/min) to give 3b as a yellow solid (330 mg, 21% yield). $^1$H NMR (400 MHz, CDCl$_3$): δ 7.99 (d, J=8.4 Hz, 1H), 7.86 (d, J=7.2 Hz, 1H), 7.79 (d, J=2.0 Hz, 1H), 7.49-7.45 (m, 2H), 7.42 (d, J=16.0 Hz, 1H), 7.37 (t, J=7.2 Hz, 1H), 7.28 (d, J=16.0 Hz, 1H), 7.18 (d, J=8.8 Hz, 1H), 5.29 (s, 2H), 3.53 (s, 3H); MS (ESI) m/z 375.8 and 377.8 [M+H]$^+$.

(E)-6-bromo-2-(3-methoxy-4-(methoxymethoxy)styryl)benzo[d]thiazole (3c)

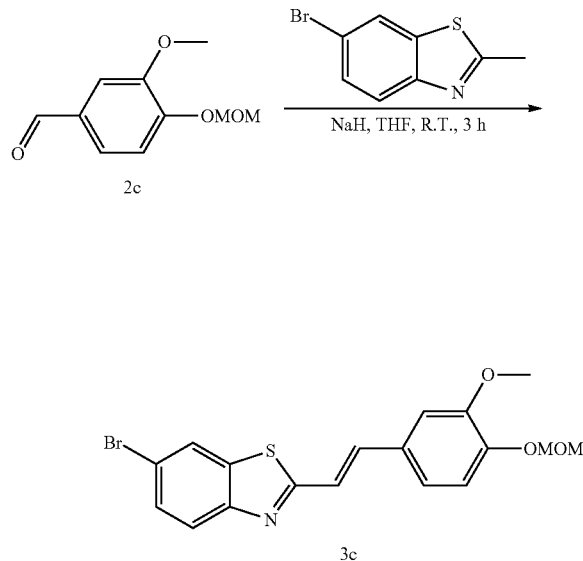

To a suspension of sodium hydride (1.19 g, 26.4 mmol) in anhydrous THF (30 mL) was added 6-bromo-2-methylbenzothiazole (3.0 g, 13.2 mmol) at 0° C. under nitrogen. The reaction mixture was stirred at room temperature for 1 h before 2c (2.8 g, 14.5 mmol) was added. The reaction mixture was stirred at room temperature for another 3 h. Water (100 mL) was added and the mixture was extracted with ethyl acetate (2×100 mL). The organic layers were combined, washed with brine (3×100 mL), dried over anhydrous Na$_2$SO$_4$, filtered and concentrated. The residue was purified by silica gel column chromatography using 10% MeOH/CH$_2$Cl$_2$ as eluent to give 3c as a yellow solid (3.3 g, 61% yield). $^1$H NMR (400 MHz, DMSO-d$_6$): δ 8.38 (d, J=2.0 Hz, 1H), 7.87 (d, J=8.4 Hz, 1H), 7.65 (dd, J=8.8, 2.0 Hz, 1H), 7.63 (d, J=16.0 Hz, 1H), 7.55 (d, J=16.0 Hz, 1H), 7.48 (d, J=1.6 Hz, 1H), 7.29 (dd, J=8.4, 1.6 Hz, 1H), 7.11 (d, J=8.4 Hz, 1H), 5.22 (s, 2H), 3.87 (s, 3H), 3.40 (s, 3H); MS (ESI) m/z 405.8 and 407.8 [M+H]$^+$.

(E)-4-(2-(benzo[d]thiazol-2-yl)vinyl)-2-methoxyphenol (EU-001-01)

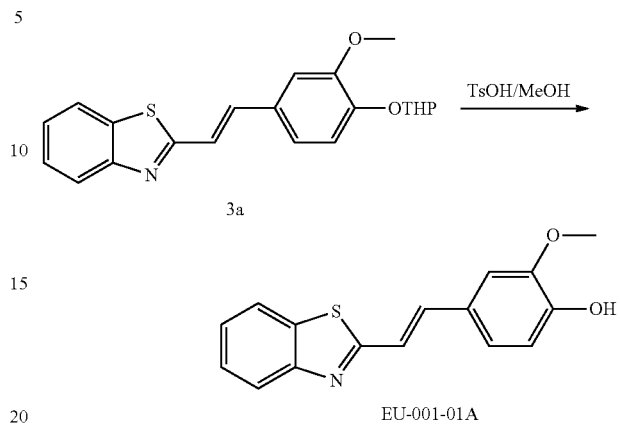

To a solution of 3a (570 mg, 1.55 mmol) in MeOH (10 mL) was added toluenesolfonic acid (53 mg, 0.31 mmol). The mixture was stirred at room temperature for 2 h. After the reaction was complete, the reaction mixture was concentrated and the residue was purified by preparative thin layer chromatography using 30% ethyl acetate in petroleum ether as eluent to afford EU-001-01A as a yellow solid (110 mg, 18% yield). $^1$H NMR (400 MHz, CD$_3$OD): δ 7.95 (d, J=8.0 Hz, 1H), 7.91 (d, J=8.0 Hz, 1H), 7.56 (d, J=16.0 Hz, 1H), 7.51 (td, J=8.4, 1.2 Hz, 1H), 7.42 (td, J=8.4, 1.2 Hz, 1H), 7.30 (d, J=16.0 Hz, 1H), 7.28 (s, 1H), 7.15 (dd, J=8.0, 2.0 Hz, 1H), 6.86 (d, J=8.4 Hz, 1H), 3.96 (s, 3H); MS (ESI) m/z 283.9 [M+H]$^+$.

(E)-4-(2-(benzo[d]thiazol-2-yl)vinyl)-2-bromophenol (EU-001-01B)

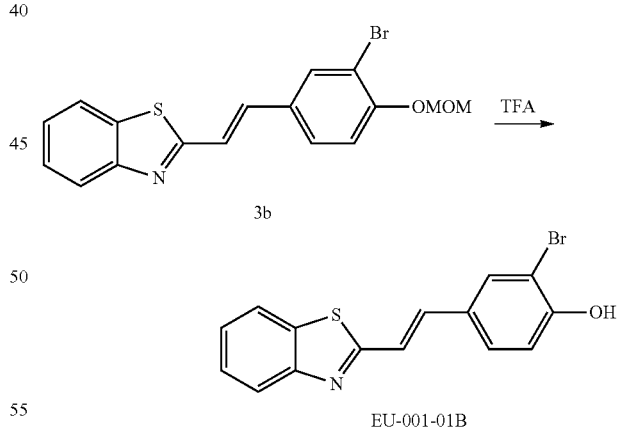

To a solution of 3b (330 mg, 0.88 mmol) in CH$_2$Cl$_2$ (4 mL) was added trifluoroacetic acid (2 mL) at 0° C. The reaction mixture was stirred at room temperature for 2 h under nitrogen atmosphere. The mixture was concentrated to give a residue, which was purified by preparatory HPLC to afford EU-001-01B as a yellow solid (105 mg, 36% yield). $^1$H NMR (400 MHz, DMSO-d$_6$): δ 10.74 (br s, 1H), 8.07 (d, J=8.0 Hz, 1H), 7.97-7.96 (m, 2H), 7.64 (dd, J=8.4, 1.6 Hz, 1H), 7.58-7.44 (m, 3H), 7.42 (t, J=7.6 Hz, 1H), 7.00 (d, J=8.8 Hz, 1H). MS (ESI) m/z 331.8 and 333.8 [M+H]$^+$.

(E)-2-(3-methoxy-4-(methoxymethoxy)styryl)-N-methylbenzo[d]thiazol-6-amine (4a)

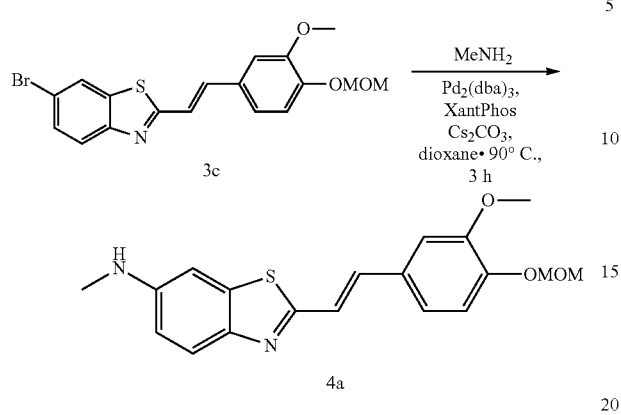

To a solution of 3c (500 mg, 1.23 mmol) in dioxane (5 mL) was added Pd$_2$(dba)$_3$ (229 mg, 0.25 mmol), 9,9-dimethyl-4,5-bis(diphenylphosphino)xanthene (145 mg, 0.25 mmol), cesium carbonate (802 mg, 2.46 mmol) and a 2.0 M solution of methylamine in THF (1.2 mL, 2.4 mmol). The mixture was stirred at 90° C. for 2 h. After cooling down to room temperature, the reaction mixture was filtered and the filtrate was concentrated. The residue was purified silica gel column chromatography using 30% ethyl acetate in petroleum ether as eluent to give 4a as a yellow solid (115 mg, 26% yield). MS (ESI) m/z 356.9 [M+H]$^+$.

(E)-2-(3-methoxy-4-(methoxymethoxy)styryl)-N,N-dimethylbenzo[d]thiazol-6-amine (4b)

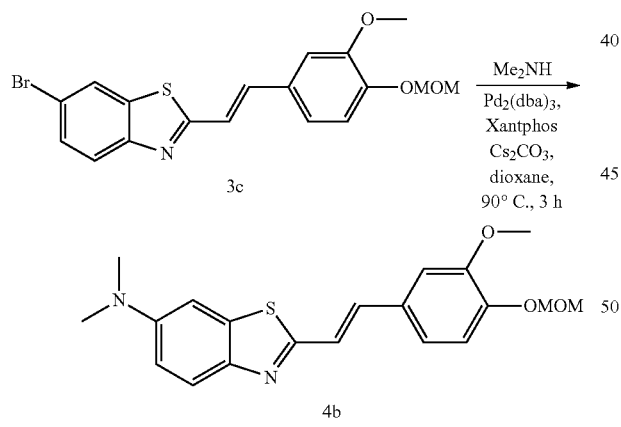

To a solution of 3c (500 mg, 1.23 mmol) in dioxane (5 mL) was added Pd$_2$(dba)$_3$ (229 mg, 0.25 mmol), 9,9-dimethyl-4,5-bis(diphenylphosphino)xanthene (145 mg, 0.25 mmol), cesium carbonate (802 mg, 2.46 mmol) and a 2.0 M solution of dimethylamine in THF (1.2 mL, 2.4 mmol). The mixture was stirred at 90° C. for 2 h. After cooling down to room temperature, the reaction mixture was filtered and the filtrate was concentrated. The residue was purified silica gel column chromatography using 30% ethyl acetate in petroleum ether as eluent to give 4b as a yellow solid (290 mg, 64% yield). MS (ESI) m/z 371.0 [M+H]$^+$.

(E)-N-ethyl-2-(3-methoxy-4-(methoxymethoxy)styryl)benzo[d]thiazol-6-amine (4c)

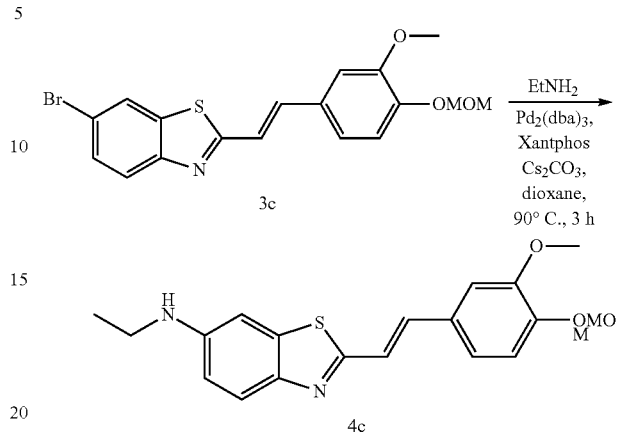

To a solution of 3c (500 mg, 1.23 mmol) in dioxane (5 mL) was added Pd$_2$(dba)$_3$ (229 mg, 0.25 mmol), 9,9-dimethyl-4,5-bis(diphenylphosphino)xanthene (145 mg, 0.25 mmol), cesium carbonate (802 mg, 2.46 mmol) and a 2.0 M solution of ethylamine in THF (1.2 mL, 2.4 mmol). The mixture was stirred at 90° C. for 2 h. After cooling down to room temperature, the reaction mixture was filtered and the filtrate was concentrated. The residue was purified silica gel column chromatography using 30% ethyl acetate in petroleum ether as eluent to give 4c as a yellow solid (310 mg, 68% yield). MS (ESI) m/z 371.0 [M+H]$^+$.

(E)-2-methoxy-4-(2-(6-(methylamino)benzo[d]thiazol-2-yl)vinyl)phenol (EU-004-01A)

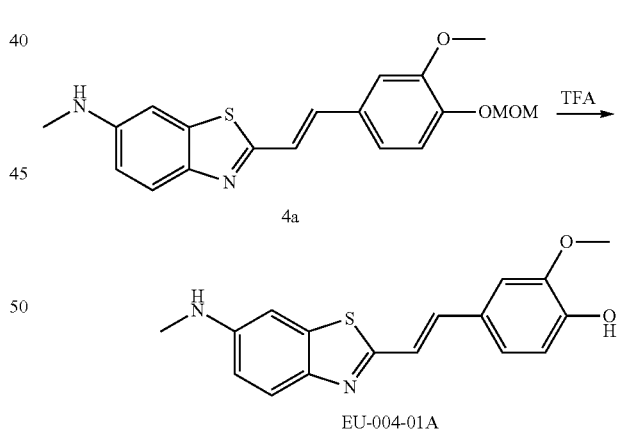

To a solution of 4a (230 mg, 0.64 mmol) in CH$_2$Cl$_2$ (4 mL) was added trifluoroacetic acid (2 mL) at 0° C. The reaction mixture was stirred at room temperature for 2 h under nitrogen atmosphere. The mixture was concentrated to give a residue, which was purified by preparatory HPLC to afford EU-004-01A as a yellow solid (105 mg, 53% yield). $^1$H NMR (400 MHz, DMSO-d$_6$): δ 9.38 (br s, 1H), 7.60 (d, J=8.8 Hz, 1H), 7.35-7.25 (m, 3H), 7.10 (dd, J=8.0, 1.6 Hz, 1H), 6.99 (d, J=2.4 Hz, 1H), 6.80 (d, J=8.0 Hz, 1H), 6.76 (dd, J=8.8, 2.4 Hz, 1H), 6.05 (q, J=5.2 Hz, 1H), 3.84 (s, 3H), 2.74 (d, J=5.2 Hz, 3H); MS (ESI) m/z 312.9 [M+H]$^+$.

(E)-4-(2-(6-(dimethylamino)benzo[d]thiazol-2-yl) vinyl)-2-methoxyphenol (EU-004-02A)

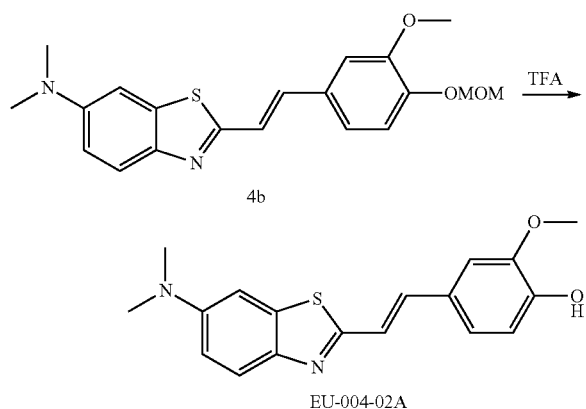

To a solution of 4b (290 mg, 0.78 mmol) in CH$_2$Cl$_2$ (4 mL) was added trifluoroacetic acid (2 mL) at 0° C. The reaction mixture was stirred at room temperature for 1 h under nitrogen atmosphere. The mixture was concentrated to give a residue, which was purified by preparatory HPLC to afford EU-004-02A as a yellow solid (110 mg, 43% yield). $^1$H NMR (400 MHz, DMSO-d$_6$): δ 9.41 (br s, 1H), 7.70 (d, J=9.2 Hz, 1H), 7.35-7.30 (m, 3H), 7.26 (d, J=2.4 Hz, 1H), 7.12 (dd, J=8.0, 1.6 Hz, 1H), 6.95 (dd, J=8.8, 2.0 Hz, 1H), 6.80 (d, J=8.0 Hz, 1H), 3.85 (s, 3H), 2.98 (s, 6H); MS (ESI) m/z 327.0 [M+H]$^+$.

(E)-4-(2-(6-(ethylamino)benzo[d]thiazol-2-yl)vinyl)-2-methoxyphenol (EU-004-03A)

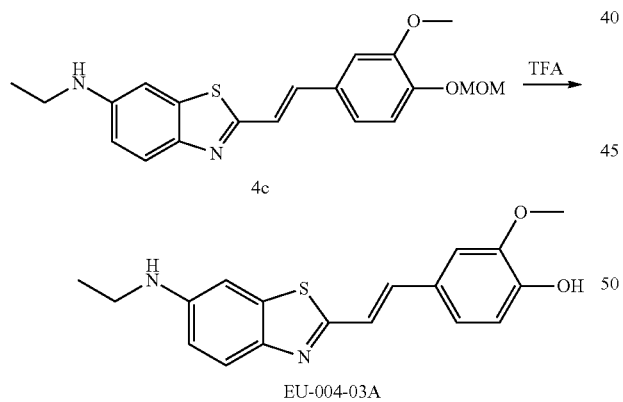

To a solution of 4c (310 mg, 0.84 mmol) in CH$_2$Cl$_2$ (4 mL) was added trifluoroacetic acid (2 mL) at 0° C. The reaction mixture was stirred at room temperature for 1 h under nitrogen atmosphere. The mixture was concentrated to give a residue, which was purified by preparatory HPLC to afford EU-004-03A as a yellow solid (110 mg, 42% yield). $^1$H NMR (400 MHz, DMSO-d$_6$): δ 9.37 (br s, 1H), 7.60 (d, J=8.8 Hz, 1H), 7.35-7.29 (m, 3H), 7.10 (dd, J=8.0, 1.6 Hz, 1H), 7.01 (d, J=2.0 Hz, 1H), 6.80-6.77 (m, 2H), 5.94 (t, J=5.2 Hz, 1H), 3.84 (s, 3H), 3.09 (q, J=6.8 Hz, 2H), 1.20 (t, J=6.8 Hz, 3H). MS (ESI) m/z 327.0 [M+H]$^+$.

(E)-2-(3-methoxy-4-((tetrahydro-2H-pyran-2-yl)oxy) styryl)-5-methylbenzo[d]thiazole (6a)

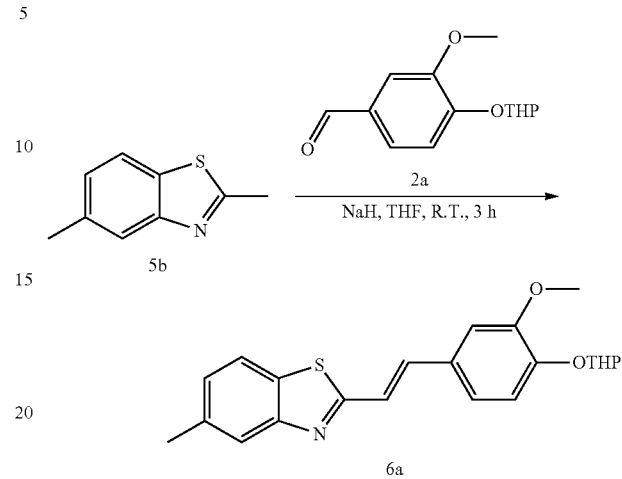

To a suspension of sodium hydride (184 mg, 4.60 mmol) in anhydrous THF (15 mL) was added 2,5-dimethylbenzothiazole 5b (300 mg, 1.84 mmol) at 0° C. under nitrogen. The reaction mixture was stirred at room temperature for 1 h before 2a (790 mg, 3.37 mmol) was added. The reaction mixture was stirred at room temperature for another 3 h. Water (20 mL) was added and the mixture was extracted with ethyl acetate (3×40 mL). The organic layers were combined and washed with brine (20 mL), dried over anhydrous Na$_2$SO$_4$, filtered and concentrated. The residue was purified on a automated flash chromatography system (with a gradient of 60-95% of acetonitrile and water over 15 min at a flow rate of 40 mL/min) to give 6a as a yellow solid (224 mg, 35% yield). MS (ESI) m/z 381.9 [M+H]$^+$.

(E)-2-(3-bromo-4-(methoxymethoxy)styryl)-5-methylbenzo[d]thiazole (6b)

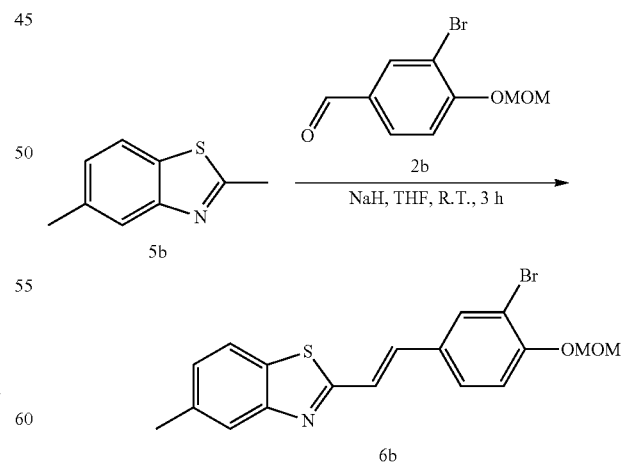

To a suspension of sodium hydride (298 mg, 7.46 mmol) in anhydrous THF (20 mL) was added 2,5-dimethylbenzothiazole 5b (607 mg, 3.73 mmol) at 0° C. under nitrogen. The reaction mixture was stirred at room temperature for 30 min before 2b (1.0 g, 4.1 mmol) was added. The mixture was stirred at room temperature for another 3 h then quenched with water (2 mL). The reaction mixture was concentrated to give a crude product, which was purified on a automated flash chromatography system (with a gradient of 20-95% of acetonitrile and water over 15 min at a flow rate of 40 mL/min) to give 6b as a yellow solid (247 mg, 16% yield). $^{1}$H NMR (400 MHz, CDCl$_3$): δ 7.78 (d, J=1.6 Hz, 2H), 7.72 (d, J=8.4 Hz, 1H), 7.47 (d, J=8.8, 2.0 Hz, 1H), 7.40 (d, J=16.0 Hz, 1H), 7.27 (d, J=16.0 Hz, 1H), 7.19 (t, J=8.4 Hz, 2H), 5.29 (s, 2H), 3.53 (s, 3H), 2.50 (s, 3H); MS (ESI) m/z 389.8 and 391.8 [M+H]$^+$.

(E)-2-methoxy-4-(2-(5-methylbenzo[d]thiazol-2-yl)vinyl)phenol (EU-002-01A)

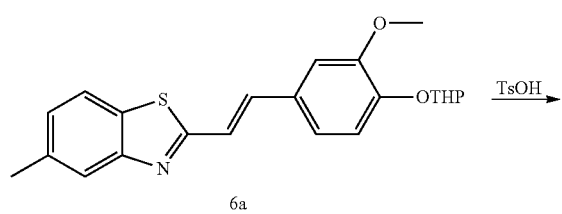

To a solution of 6a (224 mg, 0.59 mmol) in MeOH(10 mL) was added toluenesulfonic acid (20 mg, 0.12 mmol). The mixture was stirred at room temperature for 2 h under nitrogen atmosphere. The reaction mixture was concentrated, and the residue was partitioned between ethyl acetate (50 mL) and saturated NaHCO$_3$ aqueous solution (20 mL). The organic layer was dried over anhydrous Na$_2$SO$_4$, filtered and concentrated to give a residue, which was purified by preparatory HPLC to afford EU-002-01A as a yellow solid (101 mg, 59% yield). $^{1}$H NMR (400 MHz, DMSO-d$_6$): δ 9.48 (s, 1H), 7.92 (d, J=8.4 Hz, 1H), 7.74 (s, 1H), 7.52 (d, J=16.0 Hz, 1H), 7.43 (d, J=16.0 Hz, 1H), 7.39 (d, J=1.6 Hz, 1H), 7.22 (dd, J=8.4, 1.6 Hz, 1H), 7.17 (dd, J=8.4, 1.6 Hz, 1H), 6.82 (d, J=8.4 Hz, 1H), 3.85 (s, 3H), 2.45 (s, 3H); MS (ESI) m/z 297.9 [M+H]$^+$.

(E)-2-bromo-4-(2-(5-methylbenzo[d]thiazol-2-yl)vinyl)phenol (EU-002-01B)

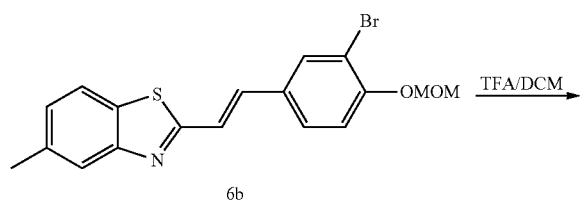

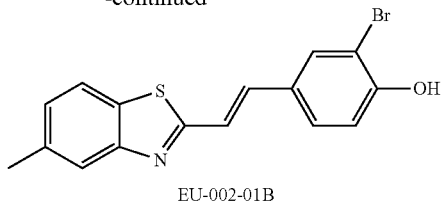

To a solution of 6b (247 mg, 0.64 mmol) in CH$_2$Cl$_2$ (4 mL) was added trifluoroacetic acid (2 mL) at 0° C. The mixture was stirred at 0° C. for 2 h under nitrogen atmosphere. The reaction mixture was concentrated to give a residue, which was purified by preparatory HPLC to afford EU-002-01B as a yellow solid (90 mg, 41% yield). $^{1}$H NMR (400 MHz, DMSO-d$_6$): δ 10.72 (br s, 1H), 7.96-7.95 (m, 1H), 7.93 (d, J=8.0 Hz, 1H), 7.76 (s, 1H), 7.63 (dd, J=8.4, 2.0 Hz, 1H), 7.48 (d, J=16.4 Hz, 1H), 7.44 (d, J=16.4 Hz, 1H), 7.50 (d, J=8.0 Hz, 1H), 7.00 (d, J=8.4 Hz, 1H), 2.45 (s, 3H). MS (ESI) m/z 345.8 and 347.8 [M+H]$^+$.

(E)-2-methoxy-4-(2-(5-nitrobenzo[d]thiazol-2-yl)vinyl)phenol (8a)

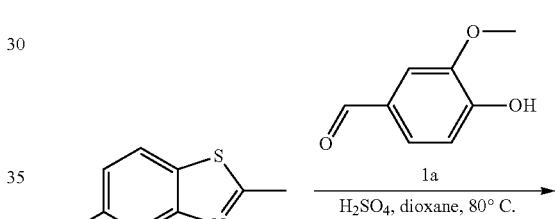

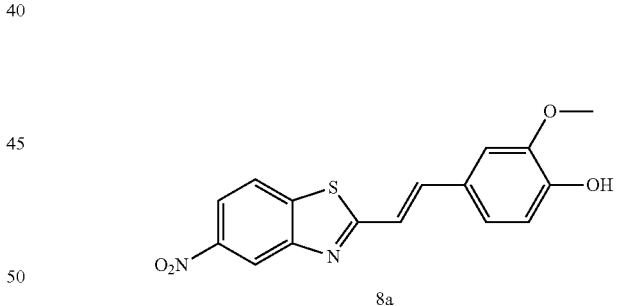

To a mixture of 7 (800 mg, 4.12 mmol) and 1a (626 mg, 4.12 mmol) in dioxane (20 mL) was added concentrate H$_2$SO$_4$ (444 mg, 4.53 mmol) at room temperature. The mixture was stirred at 100° C. for 8 h under nitrogen. After the reaction was complete, the suspension was filtered and the filter cake was washed with water (2×50 mL), saturated NaHCO$_3$ aqueous solution (2×50 mL) and water (100 mL) sequentially. The filter cake was dried under high vacuum to afford 8a (1.0 g, 76% yield) as a yellow solid. $^{1}$H NMR (300 MHz, DMSO-d$_6$): δ 9.59 (s, 1H), 8.63 (d, J=2.1 Hz, 1H), 8.32 (d, J=8.7 Hz, 1H), 8.19 (dd, J=8.7, 2.1 Hz, 1H), 7.64 (d, J=16.2 Hz, 1H), 7.50 (d, J=16.2 Hz, 1H), 7.41 (d, J=1.8 Hz, 1H), 7.19 (d, J=8.1 Hz, 1H), 6.80 (d, J=8.1 Hz, 1H), 3.83 (s, 3H); MS (ESI) m/z 328.9 [M+H]$^+$.

(E)-2-bromo-4-(2-(5-nitrobenzo[d]thiazol-2-yl)vinyl)phenol (8b)

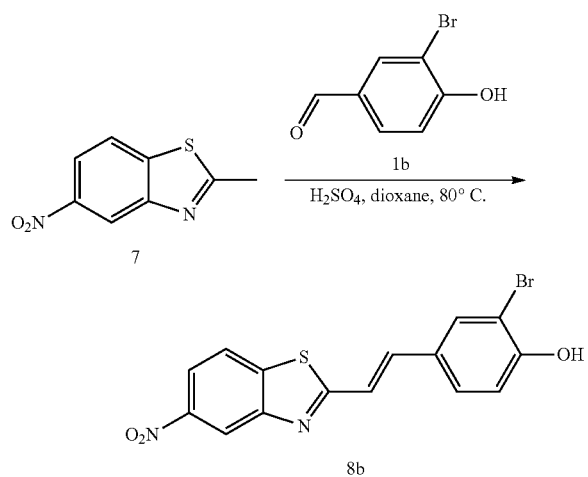

To a mixture of 7 (800 mg, 4.12 mmol) mad 1b (828 mg, 4.12 mmol) in dioxane (20 mL) was added concentrated $H_2SO_4$ (444 mg, 4.53 mmol) at room temperature. The mixture was stirred at 100° C. overnight under nitrogen. After the reaction was complete, the suspension was filtered and the filter cake was washed with saturated $NaHCO_3$ aqueous solution (50 mL), water (2×50 mL) and cold methanol (20 mL) sequentially. The filter cake was dried under high vacuum to afford 8b (1.2 g, 80% yield) as a yellow solid. $^1$H NMR (300 MHz, DMSO-$d_6$): δ 10.81 (s, 1H), 8.66 (d, J=2.1 Hz, 1H), 8.34 (d, J=9.0 Hz, 1H), 8.21 (dd, J=8.7, 1.8 Hz, 1H), 7.98 (d, J=1.8 Hz, 1H), 7.68-7.61 (m, 2H), 7.51 (d, J=16.2 Hz, 1H), 6.98 (d, J=8.4, Hz, 1H); MS (ESI) m/z 376.8 and 378.8 [M+H]$^+$.

(E)-2-(3-methoxy-4-(methoxymethoxy)styryl)-5-nitrobenzo[d]thiazole (9a)

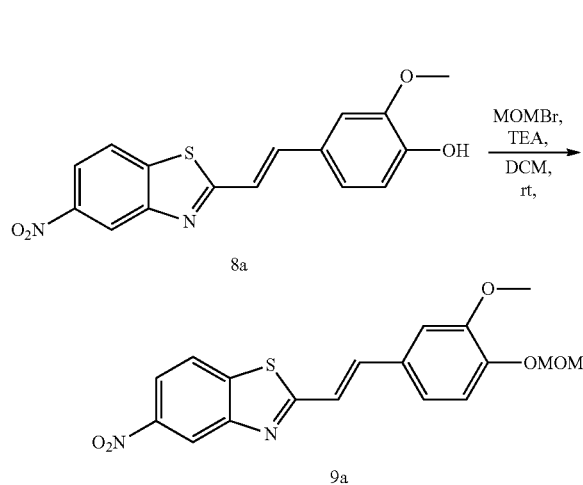

To a solution of 8a (1.0 g, 3.06 mmol) in $CH_2Cl_2$ (20 mL) was added triethylamine (930 mg, 9.2 mmol) followed by the addition of methoxymethyl bromide (765 mg, 6.12 mmol mmol) at 0° C. under nitrogen. The reaction mixture was stirred at room temperature overnight. The resulting suspension was filtered and the filter cake was washed with water (4×50 mL) to give 9a as a yellow solid (1.0 g, 87% yield). MS (ESI) m/z 372.9 [M+H]$^+$.

(E)-2-(3-bromo-4-(methoxymethoxy)styryl)-5-nitrobenzo[d]thiazole (9b)

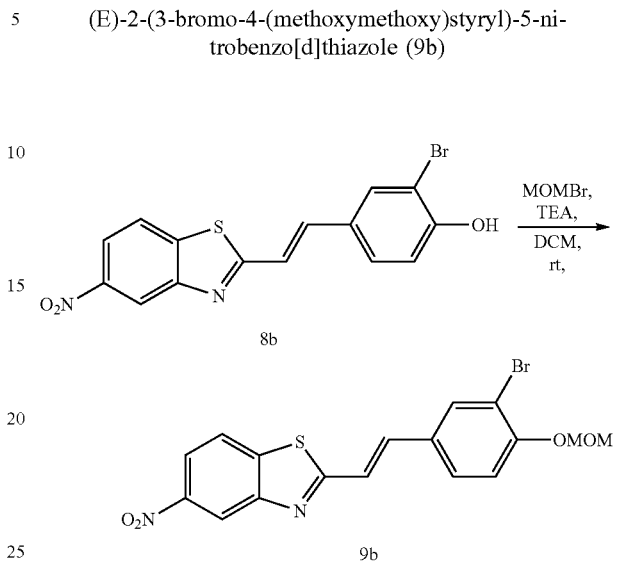

To a solution of 8b (1.2 g, 3.19 mmol) in $CH_2Cl_2$ (20 mL) was added triethylamine (970 mg, 9.6 mmol) followed by the addition of methoxymethyl bromide (798 mg, 6.38 mmol) at 0° C. under nitrogen. The reaction mixture was stirred at room temperature for 4 h. The resulting suspension was filtered and the filter cake was washed with water (4×50 mL) to give 9b as a yellow solid (1.2 g, 86% yield). MS (ESI) m/z 420.8 and 422.8 [M+H]$^+$.

(E)-2-(3-methoxy-4-(methoxymethoxy)styryl)benzo[d]thiazol-5-amine (10a)

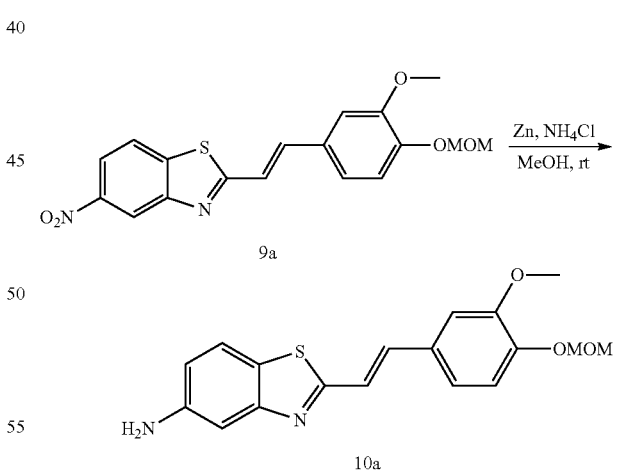

To a suspension of 9a (1.0 g, 2.69 mmol) in MeOH (50 mL) was added and ammonium chloride (726 mg, 13.4 mmol) and zinc powder (874 mg, 13.4 mmol). The mixture was stirred room temperature for 3 h. The suspension was filtered and the filter cake was washed with $CH_2Cl_2$ (100 mL). The filtrate was concentrated and the residue was washed with water (4×50 mL). The filter cake was dried under high vacuum to afford 10a as a yellow solid (800 mg, 87% yield). MS (ESI) m/z 343.0 [M+H]$^+$.

(E)-2-(3-bromo-4-(methoxymethoxy)styryl)benzo[d]thiazol-5-amine (10b)

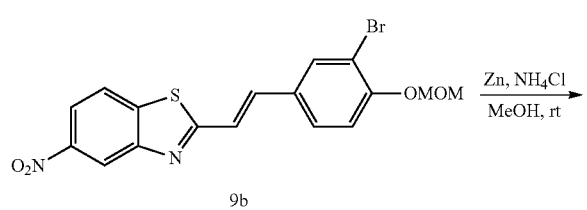

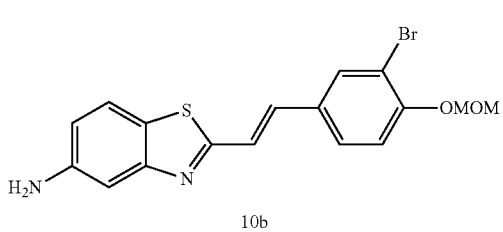

To a suspension of 9b (1.2 g, 2.84 mmol) in MeOH (50 mL) was added and ammonium chloride (768 mg, 14.2 mmol) and zinc powder (924 mg, 14.2 mmol). The mixture was stirred room temperature for 3 h. The suspension was filtered and the filter cake was washed with $CH_2Cl_2$ (200 mL). The filtrate was concentrated and the residue was washed with water (4×50 mL). The filter cake was dried under high vacuum to afford 10b as a yellow solid (1.0 g, 90% yield). MS (ESI) m/z 390.8 and 392.8 $[M+H]^+$.

(E)-tert-butyl (2-(3-methoxy-4-(methoxymethoxy)styryl)benzo[d]thiazol-5-yl)carbamate (11a)

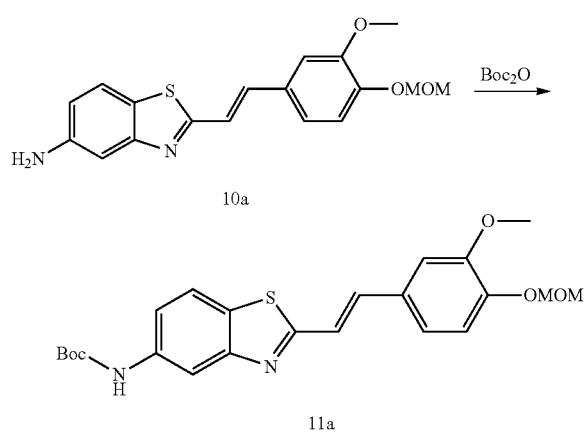

A mixture of 10a (800 mg, 2.34 mmol) and $Boc_2O$ (20 mL) was heated at 80° C. for 2 h. The excess $Boc_2O$ was removed under high vacuum and the residue was purified by silica gel column chromatography with petroleum ether then 10% ethyl acetate in petroleum ether as eluent to afford 11a as yellow oil (850 mg, 82% yield). MS (ESI) m/z 443.0 $[M+H]^+$.

(E)-tert-butyl (2-(3-bromo-4-(methoxymethoxy)styryl)benzo[d]thiazol-5-yl)carbamate (11b)

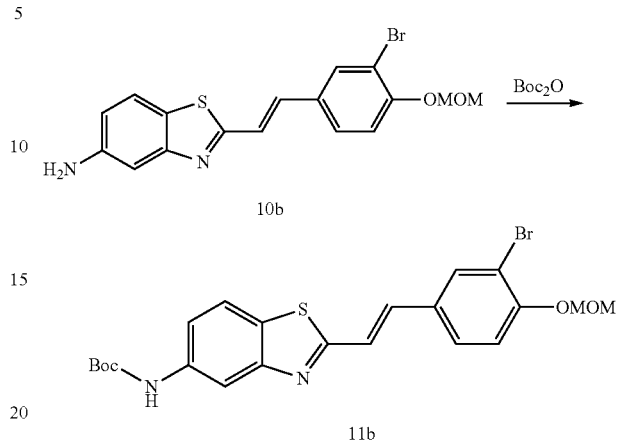

A mixture of 10b (1.0 g, 2.55 mmol) and $Boc_2O$ (30 mL) was heated at 80° C. for 2 h. The excess $Boc_2O$ was removed under high vacuum and the residue was purified by silica gel column chromatography with petroleum ether then 10% ethyl acetate in petroleum ether as eluent to afford 11b as yellow oil (800 mg, 63% yield). MS (ESI) m/z 490.9 and 492.9 $[M+H]^+$.

(E)-tert-butyl (2-(3-methoxy-4-(methoxymethoxy)styryl)benzo[d]thiazol-5-yl)(methyl)carbamate (12a)

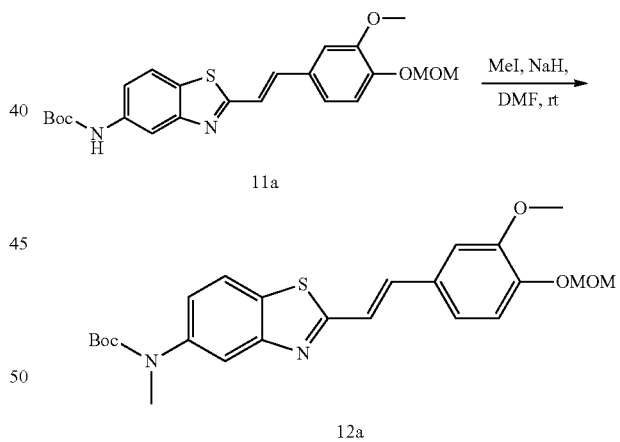

To a suspension of sodium hydride (216 mg, 5.40 mmol, 60% suspension in mineral oil) in anhydrous THF (10 mL) was added 11a (800 mg, 1.80 mmol) at 0° C. The mixture was stirred for 5 min before methyl iodide (770 mg, 5.40 mmol) was added at 0° C. under nitrogen. The reaction was stirred at room temperature for 1 h, quenched with saturated ammonium chloride aqueous solution (10 mL) and extracted with ethyl acetate (2×20 mL). The organic layers were combined, dried over anhydrous $Na_2SO_4$ and filtered. The filtrate was concentrated and the residue was purified by silica gel column chromatography with 30% ethyl acetate in petroleum ether to give 12a (450 mg, 55% yield) as a yellow oil. MS (ESI) m/z 457.0 $[M+H]^+$.

(E)-tert-butyl (2-(3-bromo-4-(methoxymethoxy)styryl)benzo[d]thiazol-5-yl)(methyl)carbamate (12b)

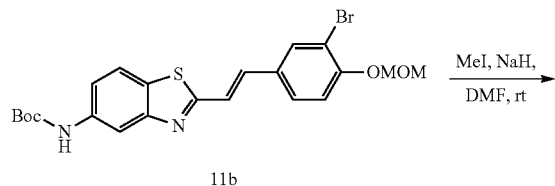

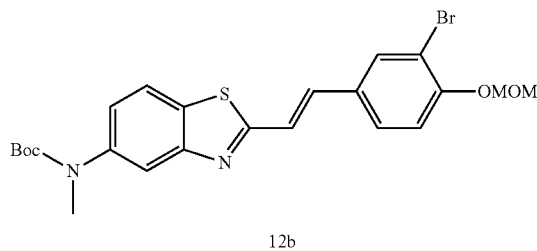

To a suspension of sodium hydride (196 mg, 4.89 mmol, 60% suspension in mineral oil) in anhydrous THF (10 mL) was added 11b (800 mg, 1.63 mmol) at 0° C. The mixture was stirred for 10 min before ethyl iodide (694 mg, 4.89 mmol) was added at 0° C. under nitrogen. The reaction was stirred at room temperature for 1 h, quenched with saturated ammonium chloride aqueous solution (5 mL) and extracted with ethyl acetate (3×20 mL). The organic layers were combined, dried over anhydrous $Na_2SO_4$ and filtered. The filtrate was concentrated and the residue was purified by silica gel column chromatography with 0-50% ethyl acetate in petroleum ether to give 12b (680 mg, 82% yield) as a yellow oil. MS (ESI) m/z 504.9 and 506.9 $[M+H]^+$.

(E)-2-methoxy-4-(2-(5-(methylamino)benzo[d]thiazol-2-yl)vinyl)phenol (EU-003-01A)

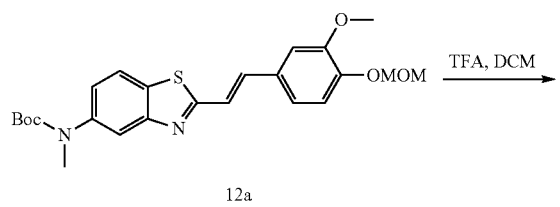

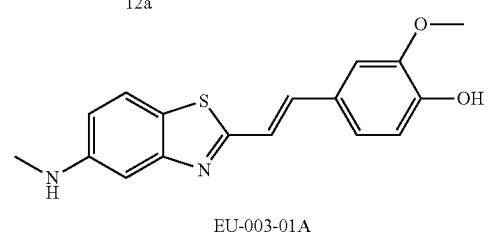

To a solution of 12a (400 mg, 0.88 mmol) in $CH_2Cl_2$ (2 mL) was added trifluoroacetic acid (2 mL) at 0° C. The mixture was stirred at this temperature for 2 h under nitrogen atmosphere. The reaction was quenched with saturated $NaHCO_3$ aqueous solution at low temperature and extracted with ethyl acetate (3×20 mL). The organic layers were combined and concentrated to give a residue, which was purified by preparatory HPLC to afford EU-003-01A as a yellow solid (117 mg, 43% yield). $^1$H NMR (400 MHz, DMSO-$d_6$): δ 9.44 (s, 1H), 7.66 (d, J=8.4 Hz, 1H), 7.45 (d, J=16.0 Hz, 1H), 7.36 (d, J=2.0 Hz, 1H), 7.35 (d, J=16.0 Hz, 1H), 7.13 (dd, J=8.4, 2.0 Hz, 1H), 6.94 (d, J=2.4 Hz, 1H), 6.80 (d, J=8.0 Hz, 1H), 6.74 (dd, J=8.8, 2.0 Hz, 1H), 5.87 (q, J=4.4 Hz, 1H), 3.85 (s, 3H), 2.74 (d, J=4.4 Hz, 3H); MS (ESI) m/z 313.0 $[M+H]^+$.

(E)-2-bromo-4-(2-(5-(methylamino)benzo[d]thiazol-2-yl)vinyl)phenol (EU-003-01B)

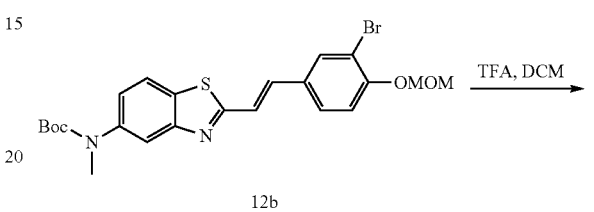

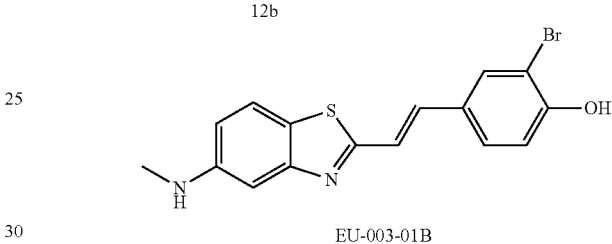

To a solution of 12b (680 mg, 1.34 mmol) in $CH_2Cl_2$ (2 mL) was added trifluoroacetic acid (2 mL) at 0° C. The mixture was stirred at 0° C. for 2 h under nitrogen atmosphere. The reaction was concentrated under low temperature and the residue was neutralized to pH=7 with saturated $NaHCO_3$ aqueous solution. The aqueous solution was extracted with ethyl acetate (2×20 mL). The organic layers were combined and concentrated to give a residue, which was purified on a automated flash chromatography system (with a gradient of 30-95% of acetonitrile and water over 15 min at a flow rate of 40 mL/min) to afford EU-003-01B as a yellow solid (180 mg, 37% yield). $^1$H NMR (300 MHz, DMSO-$d_6$): δ 10.68 (s, 1H), 7.92 (d, J=1.8 Hz, 1H), 7.67 (d, J=8.7 Hz, 1H), 7.59 (dd, J=8.4, 1.8 Hz, 1H), 7.45 (d, J=15.9 Hz, 1H), 7.36 (d, J=16.2 Hz, 1H), 6.99 (d, J=8.7 Hz, 1H), 6.95 (d, J=2.1 Hz, 1H), 6.75 (dd, J=8.7, 2.1 Hz, 1H), 5.87 (q, J=4.8 Hz, 1H), 2.74 (d, J=4.8 Hz, 3H); MS (ESI) m/z 360.8 and 362.8 $[M+H]^+$.

2-Methyl-6-nitro-benzothiazole (13a)

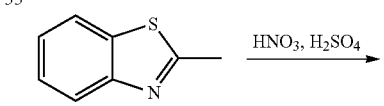

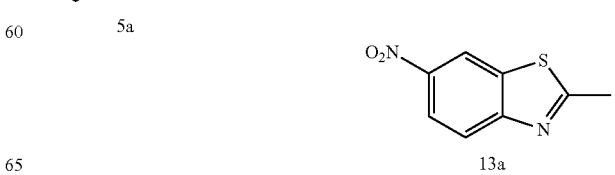

To a solution of 5a (1.76 g, 11.8 mmol) in concentrate H$_2$SO$_4$ (10 mL) was added fuming HNO$_3$ (1 mL) slowly at 0° C. The mixture was stirred at room temperature for 3 h under nitrogen atmosphere. After the reaction was completed, the reaction mixture was poured into ice-water (100 mL). The precipitate was collected by filtration and the filter cake was washed with saturated NaHCO$_3$ aqueous solution (3×10 mL), water (2×10 mL) and dried under high vacuum to afford 13a as a yellow solid (1.5 g, 66% yield). $^1$H NMR (400 MHz, CDCl$_3$): δ 8.76 (d, J=2.0 Hz, 1H), 8.32 (dd, J=8.8, 2.4 Hz, 1H), 8.02 (d, J=8.8 Hz, 1H), 2.91 (s, 3H). MS (ESI) m/z 194.8 [M+H]$^+$.

2-methyl-6-nitrobenzo[d]thiazole (13b)

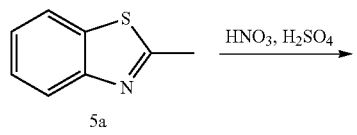

To a solution of 5b (10 g, 6.0 mol) in concentrate H$_2$SO$_4$ (60 mL) was added fuming HNO$_3$ (4 mL) slowly at 0° C. The mixture was stirred at 0° C. for 2 h under nitrogen atmosphere. After the reaction was complete, the reaction mixture was poured into ice-water (500 mL). The precipitate was collected by filtration and the filter cake was washed with saturated aqueous sodium bicarbonate (3×10 mL) and water (2×10 mL) to give the crude product, which was purified by silica gel column chromatography using 5% ethyl acetate in petroleum ether as eluent to afford 13b as a yellow solid (5.2 g, 41% yield). $^1$H NMR (400 MHz, CDCl$_3$): δ 8.52 (s, 1H), 7.85 (s, 1H), 2.88 (s, 3H), 2.72 (s, 3H); MS (ESI) m/z 208.8 [M+H]$^+$.

(E)-2-bromo-4-(2-(6-nitrobenzo[d]thiazol-2-yl)vinyl)phenol (14a)

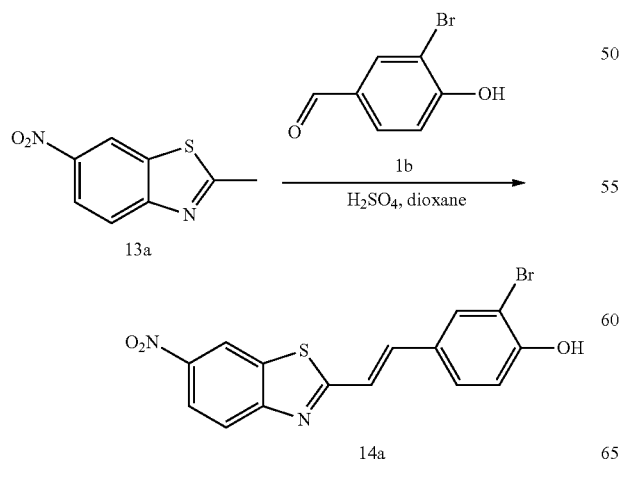

To a solution of 13a (4.1 g, 21.2 mmol) and 1b (4.25 g, 21.2 mmol) in dioxane (10 mL) was added concentrate H$_2$SO$_4$ (2.28 g, 23.3 mmol) at room temperature. The mixture was stirred at 100° C. overnight under nitrogen atmosphere. After the reaction was complete, the reaction mixture was cooling down to room temperature. The precipitate was collected by filtration and the filter cake was washed with saturated NaHCO$_3$ aqueous solution (3×10 mL), water (2×10 mL) and cold methanol (10 mL) sequentially. The solid was dried under high vacuum to afford 14a as a yellow solid (5.06 g, 64% yield). $^1$H NMR (400 MHz, DMSO-d$_6$): δ 9.12 (s, 1H), 8.31 (dd, J=9.2, 2.4 Hz, 1H), 8.09 (d, J=8.8 Hz, 1H), 8.01 (d, J=2.0 Hz, 1H), 7.72 (d, J=16.0 Hz, 1H), 6.67 (dd, J=8.4, 2.0 Hz, 1H), 7.54 (d, J=16.0 Hz, 1H), 7.01 (d, J=8.4 Hz, 1H); MS (ESI) m/z 376.8 and 378.8 [M+H]$^+$.

(E)-2-methoxy-4-(2-(5-methyl-6-nitrobenzo[d]thiazol-2-yl)vinyl)phenol (14b)

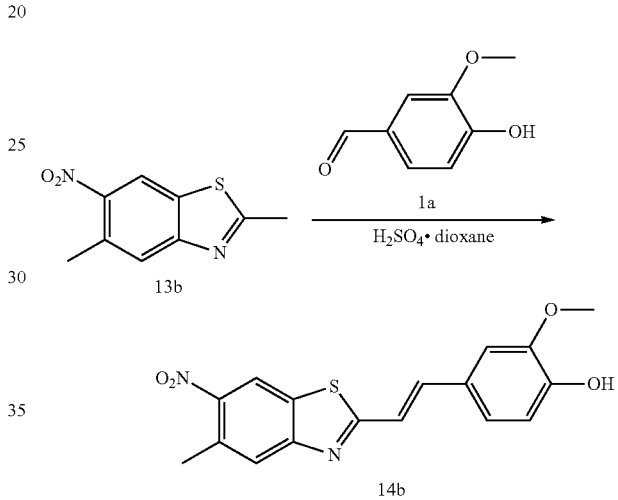

To a solution of 13b (2.7 g, 13 mmol) and 1a (2.2 g, 14 mmol) in dioxane (60 mL) was added concentrate H$_2$SO$_4$ (1.4 g, 14 mmol) at room temperature. The mixture was stirred at 100° C. overnight under nitrogen atmosphere. After the reaction was complete, the reaction mixture was cooling down to room temperature. The precipitate was collected by filtration and the filter cake was washed with saturated NaHCO$_3$ aqueous solution (3×10 mL) and water (2×10 mL). The solid was dried under high vacuum to afford 14b as a yellow solid (4.3 g, 97% yield). MS (ESI) m/z 342.9 [M+H]$^+$.

(E)-2-bromo-4-(2-(5-methyl-6-nitrobenzo[d]thiazol-2-yl)vinyl)phenol (14c)

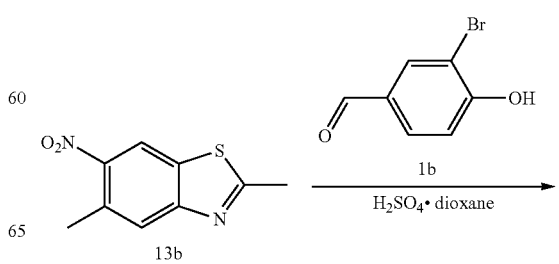

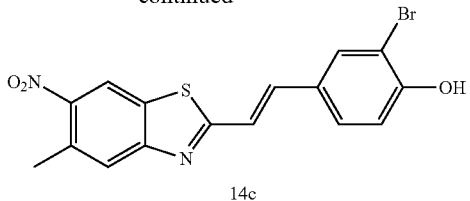

To a solution of 13b (2.1 g, 10 mmol) and 1b (2.23 g, 11 mmol) in dioxane (60 mL) was added concentrate H$_2$SO$_4$ (1.09 g, 11 mmol) at room temperature. The mixture was stirred at 100° C. overnight under nitrogen atmosphere. After the reaction was complete, the reaction mixture was cooling down to room temperature. The precipitate was collected by filtration and the filter cake was washed with saturated NaHCO$_3$ aqueous solution (3×10 mL) and water (2×10 mL). The solid was dried under high vacuum to afford 14c as a yellow solid (4.2 g, 95% yield). $^1$H NMR (400 MHz, DMSO-d$_6$): δ 10.86 (s, 1H), 8.88 (s, 1H), 8.01 (d, J=2.0 Hz, 1H), 8.00 (s, 1H), 7.70-7.65 (m, 2H), 7.53 (d, J=16.0 Hz, 3H), 7.01 (d, J=8.4 Hz, 1H), 2.64 (s, 3H); MS (ESI) m/z 390.8 and 392.8 [M+H]$^+$.

(E)-2-(3-bromo-4-(methoxymethoxy)styryl)-6-nitrobenzo[d]thiazole (15a)

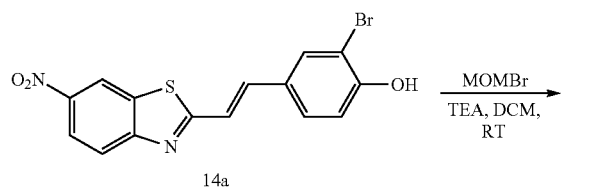

To a solution of 14a (2.6 g, 6.91 mmol) in CH$_2$Cl$_2$ (30 mL) was added triethylamine (1.4 g, 13.8 mmol) and methoxymethyl bromide (1.74 g, 13.8 mmol) at room temperature. The reaction mixture was stirred room temperature overnight under nitrogen atmosphere. After the reaction was complete, the reaction mixture was concentrated and the residue was suspended in DMF (30 mL) and water (30 mL). The solid was collected by filtration and the filter cake was washed with water (3×50 mL) and methanol (20 mL) to give 15a as a yellow solid (2.5 g, 86% yield). $^1$H NMR (400 MHz, DMSO-d$_6$): δ 9.15 (d, J=2.0 Hz, 1H), 8.33 (s, 1H), 8.14-8.11 (m, 2H), 7.84 (s, 1H), 7.79 (d, J=16.0 Hz, 1H), 7.68 (d, J=16.0 Hz, 1H), 7.28 (d, J=8.4 Hz, 1H), 5.37 (s, 2H), 3.43 (s, 3H); MS (ESI) m/z 420.8 and 422.8 [M+H]$^+$.

(E)-2-(3-methoxy-4-(methoxymethoxy)styryl)-5-methyl-6-nitrobenzo[d]thiazole (15b)

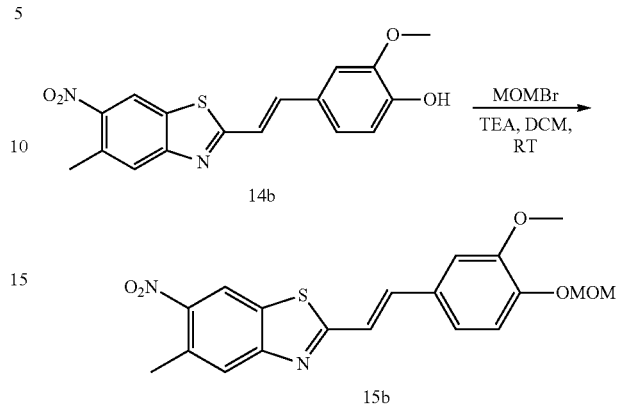

To a solution of 14b (5.7 g, 16.7 mmol) in CH$_2$Cl$_2$ (300 mL) was added triethylamine (3.37 g, 33.1 mmol) and methoxymethyl bromide (4.17 g, 33.1 mmol) at room temperature. The reaction mixture was stirred room temperature overnight under nitrogen atmosphere. After the reaction was complete, the reaction mixture was concentrated and the residue was suspended in water (100 mL). The solid was collected by filtration and the filter cake was washed with water (3×50 mL) and methanol (20 mL) to give 15b as a brown solid (5.2 g, 81% yield). MS (ESI) m/z 386.9 [M+H]$^+$.

(E)-2-(3-bromo-4-(methoxymethoxy)styryl)-5-methyl-6-nitrobenzo[d]thiazole (15c)

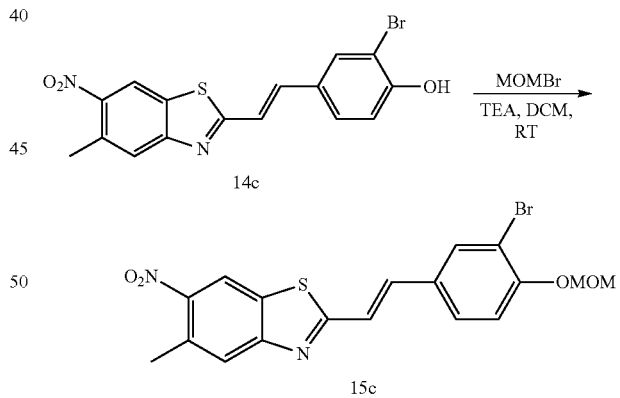

To a solution of 14c (4.26 g, 10.9 mmol) in CH$_2$Cl$_2$ (100 mL) was added triethylamine (3.33 g, 33.0 mmol) and methoxymethyl bromide (2.75 g, 22.0 mmol) at 0° C. The reaction mixture was stirred at room temperature overnight under nitrogen atmosphere. After the reaction was complete, the reaction mixture was concentrated, and the residue was suspended in water (100 mL). The solid was collected by filtration and the filter cake was washed with water (3×50 mL) to give 15c as a brown solid (3.3 g, 76% yield). $^1$H NMR (400 MHz, DMSO-d$_6$): δ 8.91 (s, 1H), 8.13 (d, J=2.0 Hz, 1H), 8.03 (s, 1H), 7.81 (dd, J=8.4, 2.0 Hz, 1H), 7.74 (d, J=16.4 Hz, 1H), 7.65 (d, J=16.4 Hz, 1H), 7.28 (d, J=8.8 Hz, 1H), 5.36 (s, 2H), 3.43 (s, 3H), 2.65 (s, 3H); MS (ESI) m/z 434.8 and 436.8 [M+H]+.

(E)-2-(3-bromo-4-(methoxymethoxy)styryl)benzo[d]thiazol-6-amine (16a)

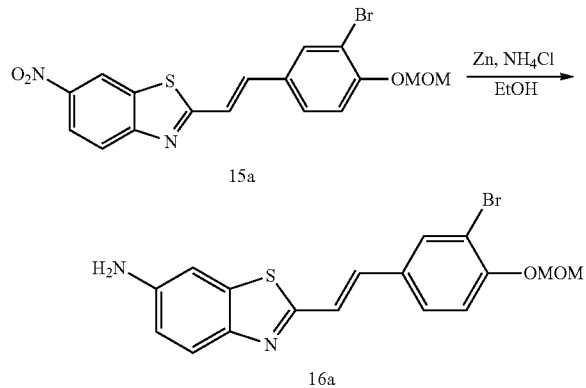

To a suspension of 15a (2.5 g, 5.95 mmol) in EtOH (100 mL) was added and ammonium chloride (1.59 g, 29.8 mmol) and zinc powder (1.93 g, 29.8 mmol). The mixture was stirred room temperature for 3 h. The suspension was filtered, and the filter cake was washed with $CH_2Cl_2$ (100 mL). The filtrate was concentrated, and the residue was treated with water (50 mL) then extracted with ethyl acetate (3×150 mL). The organic layers were combined and concentrated to afford 16a as a yellow solid (2.2 g, 98% yield). $^1$H NMR (400 MHz, DMSO-$d_6$): δ 7.99 (d, J=2.0 Hz, 1H), 7.69 (dd, J=8.4, 2.0 Hz, 1H), 7.60 (d, J=8.8 Hz, 1H), 7.43 (d, J=16.4 Hz, 1H), 7.32 (d, J=16.4 Hz, 1H), 7.23 (d, J=8.4 Hz, 1H), 7.04 (d, J=2.4 Hz, 1H), 6.76 (dd, J=8.4, 1.6 Hz, 1H), 5.48 (s, 2H), 5.33 (s, 2H), 3.42 (s, 3H); MS (ESI) m/z 390.8 and 392.8 [M+H]+.

(E)-2-(3-methoxy-4-(methoxymethoxy)styryl)-5-methylbenzo[d]thiazol-6-amine (16b)

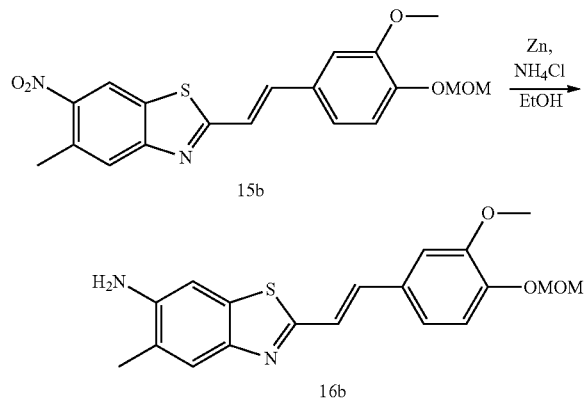

To a suspension of 15b (4.49 g, 11.6 mmol) in EtOH (50 mL) was added and ammonium chloride (3.11 g, 58.2 mmol) and zinc powder (3.11 g, 58.2 mmol). The mixture was stirred room temperature for 3 h. The suspension was filtered and the filter cake was washed with $CH_2Cl_2$ (100 mL). The filtrate was concentrated and the residue was washed with water (4×50 mL) and dried under high vacuum to afford 16b as a yellow solid (3.58 g, 87% yield). MS (ESI) m/z 357.0 [M+H]+.

(E)-2-(3-bromo-4-(methoxymethoxy)styryl)-5-methylbenzo[d]thiazol-6-amine (16c)

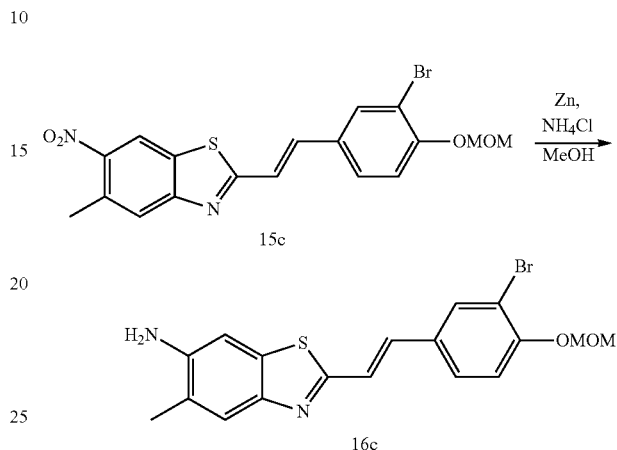

To a suspension of 15c (3.3 g, 7.59 mmol) in MeOH (50 mL) was added and ammonium chloride (1.59 g, 29.8 mmol) and zinc powder (1.93 g, 29.8 mmol). The mixture was stirred room temperature for 3 h. The suspension was filtered and the filter cake was washed with $CH_2Cl_2$ (2×100 mL) and MeOH (2×100 mL). The filtrate was concentrated and the residue was washed with water (3×100 mL). The wet material was dried under vacuum o afford 16c as a yellow solid (2.9 g, 94% yield). $^1$H NMR (400 MHz, DMSO-$d_6$): δ 7.99 (s, 1H), 7.69 (dd, J=8.4, 2.0 Hz, 1H), 7.54 (s, 1H), 7.43 (d, J=16.4 Hz, 1H), 7.31 (d, J=16.4 Hz, 1H), 7.23 (d, J=8.8 Hz, 1H), 7.10 (s, 1H), 5.33 (s, 2H), 5.27 (br s, 2H), 3.42 (s, 3H), 2.18 (s, 3H); MS (ESI) m/z 404.8 and 406.8 [M+H]+.

(E)-tert-butyl (2-(3-bromo-4-(methoxymethoxy)styryl)benzo[d]thiazol-6-yl)carbamate (17a)

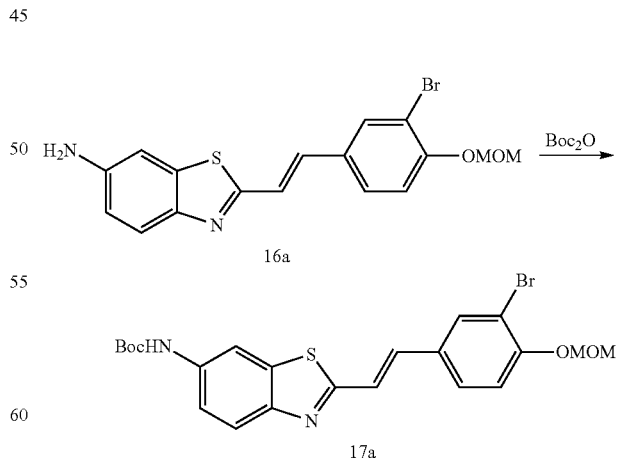

A mixture of 16a (3.94 g, 10.1 mmol) and $Boc_2O$ (50 mL) was heated at 80° C. for 2 h. The excess $Boc_2O$ was removed under high vacuum and the residue was purified by silica gel column chromatography using 100% petroleum ether and 3% MeOH in CH$_2$Cl$_2$ as eluent to afford 17a as a yellow solid (3.7 g, 76% yield). $^1$H NMR (400 MHz, DMSO-d$_6$): δ 9.66 (s, 1H), 8.26 (s, 1H), 8.06 (d, J=2.0 Hz, 1H), 7.83 (d, J=8.8 Hz, 1H), 7.74 (dd, J=8.8, 2.0 Hz, 1H), 7.51 (s, 2H), 7.46 (dd, J=8.8, 2.0 Hz, 1H), 7.25 (d, J=8.8 Hz, 1H), 5.34 (s, 2H), 3.42 (s, 3H), 1.50 (s, 9H); MS (ESI) m/z 490.8 and 492.8 [M+H]$^+$.

(E)-tert-butyl (2-(3-methoxy-4-(methoxymethoxy) styryl)-5-methylbenzo[d]thiazol-6-yl)carbamate (17b)

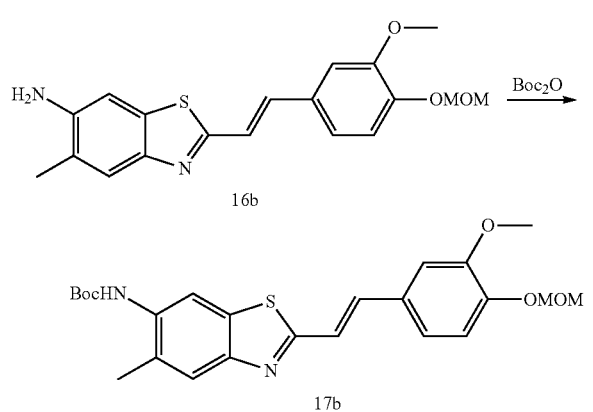

A mixture of 16b (3.58 g, 10.0 mmol) and Boc$_2$O (30 mL) was heated at 60° C. for 2 h. The excess Boc$_2$O was removed under high vacuum and the residue was purified by silica gel column chromatography using 100% petroleum ether and 3% MeOH in CH$_2$Cl$_2$ as eluent to afford 17b as a yellow solid (1.8 g, 36% yield). $^1$H NMR (400 MHz, DMSO-d$_6$): δ 8.69 (s, 1H), 8.02 (s, 1H), 7.75 (s, 1H), 7.52 (s, 2H), 7.45 (d, J=1.6 Hz, 1H), 7.26 (dd, J=8.4, 1.6 Hz, 1H), 7.10 (d, J=8.4 Hz, 1H), 5.21 (s, 2H), 3.86 (s, 3H), 3.40 (s, 3H), 2.33 (s, 3H), 1.48 (s, 9H). MS (ESI) m/z 457.0 [M+H]$^+$.

(E)-tert-butyl (2-(3-bromo-4-(methoxymethoxy) styryl)-5-methylbenzo[d]thiazol-6-yl)carbamate (17c)

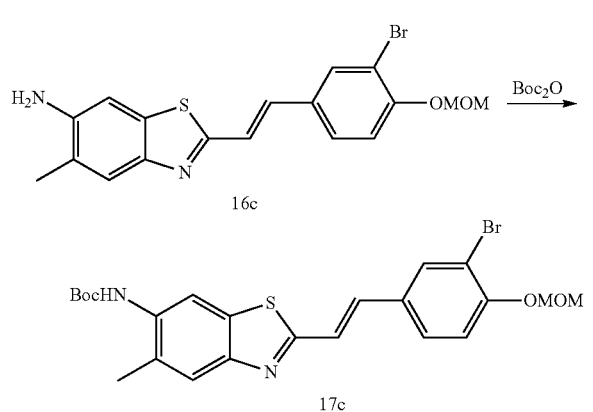

A mixture of 16c (2.1 g, 5.19 mmol) and Boc$_2$O (30 mL) was heated at 80° C. for 2 h. The excess Boc$_2$O was removed under high vacuum and the residue was purified by silica gel column chromatography using 100% petroleum ether and 3% MeOH in CH$_2$Cl$_2$ as eluent to afford 17c as a yellow solid (1.5 g, 57% yield). $^1$H NMR (400 MHz, DMSO-d$_6$): δ 8.70 (s, 1H), 8.06 (d, J=2.0 Hz, 1H), 8.03 (s, 1H), 7.77 (s, 1H), 7.75 (dd, J=8.8, 2.0 Hz, 1H), 7.53 (s, 2H), 7.25 (d, J=8.4 Hz, 1H), 5.35 (s, 2H), 3.43 (s, 3H), 2.34 (s, 3H), 1.49 (s, 9H); MS (ESI) m/z 504.8 and 506.8 [M+H]$^+$.

(E)-tert-butyl (2-(3-bromo-4-(methoxymethoxy) styryl)benzo[d]thiazol-6-yl)(methyl)carbamate (18a)

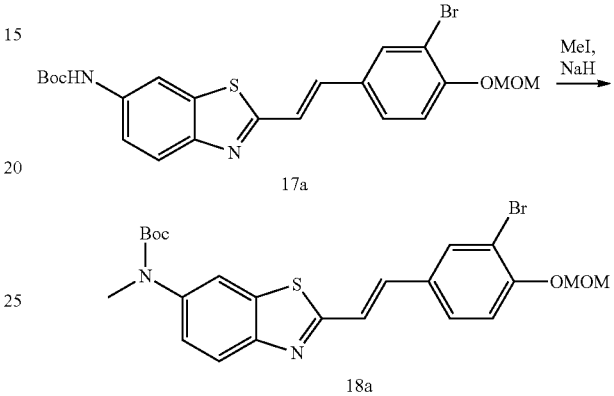

To a suspension of sodium hydride (200 mg, 5.0 mmol, 60% suspension in mineral oil) in anhydrous THF (10 mL) was added 17a (980 mg, 2.0 mmol) at 0° C. The mixture was stirred at 0° C. for 10 min before methyl iodide (710 mg, 5.0 mmol) was added under nitrogen. The reaction was stirred at room temperature for 1 h, quenched with saturated ammonium chloride aqueous solution (10 mL) and extracted with ethyl acetate (3×20 mL). The organic layers were combined, dried over anhydrous Na$_2$SO$_4$ and filtered. The filtrate was concentrated and the residue was purified by silica gel column chromatography using 60% ethyl acetate in petroleum ether as eluent to give 18a (1.0 g, 99% yield) as a yellow oil. MS (ESI) m/z 504.8 and 506.8 [M+H]$^+$.

(E)-2-(3-bromo-4-(methoxymethoxy)styryl)-N,N-dimethylbenzo[d]thiazol-6-amine (18b)

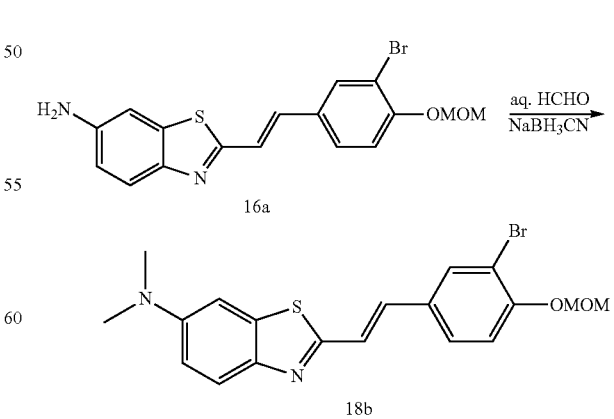

To a solution of 17a (750 mg, 1.92 mmol) in MeOH (20 mL) was added formaldehyde solution (720 mg, 9.60 mmol, 40 wt. % in water) and sodium cyanoborohydride (363 mg, 5.76 mmol) at 0° C. The mixture was stirred at room temperature overnight under nitrogen atmosphere.

The suspension was concentrated and the residue was purified by silica gel column chromatography using 25% ethyl acetate in petroleum ether as eluent to give 18b (677 mg, 84% yield) as a yellow solid. $^1$H NMR (400 MHz, DMSO-$d_6$): δ 7.81 (d, J=9.2 Hz, 1H), 7.45 (d, J=2.4 Hz, 1H), 7.44 (dd, J=8.8, 2.0 Hz, 1H), 7.24 (s, 2H), 7.16 (d, J=8.8, 1H), 7.06 (d, J=2.4 Hz, 1H), 6.93 (dd, J=8.8, 2.4 Hz, 1H), 5.28 (s, 2H), 3.53 (s, 3H), 3.03 (s, 6H); MS (ESI) m/z 418.8 and 420.8 [M+H]$^+$.

(E)-tert-butyl (2-(3-bromo-4-(methoxymethoxy) styryl)benzo[d]thiazol-6-yl)(ethyl)carbamate (18c)

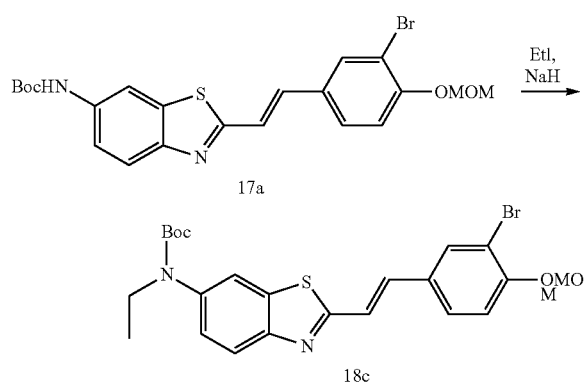

To a suspension of sodium hydride (90 mg, 2.24 mmol, 60% suspension in mineral oil) in anhydrous THF (10 mL) was added 17a (550 mg, 1.12 mmol) at 0° C. The mixture was stirred for 10 min before ethyl iodide (350 mg, 2.24 mmol) was added at 0° C. under nitrogen. The reaction was stirred at room temperature for 1 h, quenched with saturated ammonium chloride aqueous solution (5 mL) and extracted with ethyl acetate (3×20 mL). The organic layers were combined, dried over anhydrous Na$_2$SO$_4$ and filtered. The filtrate was concentrated and the residue was purified by silica gel column chromatography using 30% ethyl acetate in petroleum ether as eluent to give 18c (430 mg, 72% yield) as a yellow solid. $^1$H NMR (400 MHz, DMSO-$d_6$): δ 8.88 (d, J=1.6 Hz, 1H), 7.98 (d, J=2.0 Hz, 1H), 7.91 (d, J=8.8 Hz, 1H), 7.78 (dd, J=8.8, 2.0 Hz, 1H), 7.60 (d, J=16.4 Hz, 1H), 7.56 (d, J=16.4 Hz, 1H), 7.35 (dd, J=8.8, 2.0 Hz, 1H), 7.26 (d, J=8.8 Hz, 1H), 5.35 (s, 2H), 3.67 (q, J=6.8 Hz, 2H), 3.43 (s, 3H), 1.39 (s, 9H), 1.09 (t, J=6.8 Hz, 3H); MS (ESI) m/z 518.8 and 520.8 [M+H]$^+$.

(E)-tert-butyl (2-(3-methoxy-4-(methoxymethoxy) styryl)-5-methylbenzo[d]thiazol-6-yl)(methyl)carbamate (18d)

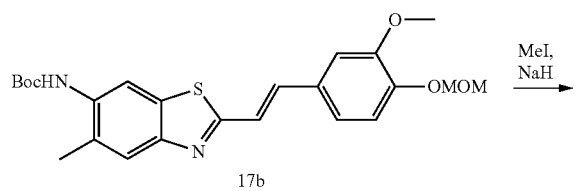

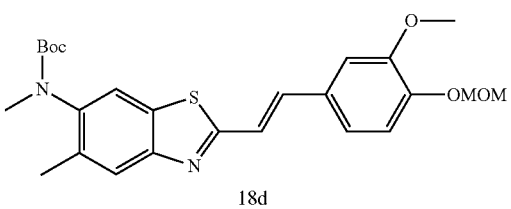

To a suspension of sodium hydride (221 mg, 5.53 mmol, 60% suspension in mineral oil) in anhydrous THF (10 mL) was added 17b (840 mg, 1.84 mmol) at 0° C. The mixture was stirred for 10 min before methyl iodide (785 mg, 5.53 mmol) was added at 0° C. under nitrogen. The reaction was stirred at room temperature for 1 h, quenched with saturated ammonium chloride aqueous solution (5 mL) and extracted with ethyl acetate (3×20 mL). The organic layers were combined, dried over anhydrous Na$_2$SO$_4$ and filtered. The filtrate was concentrated and the residue was purified by silica gel column chromatography using 30% ethyl acetate in petroleum ether as eluent to give 18d (575 mg 66% yield) as a yellow solid. MS (ESI) m/z 471.0 [M+H]$^+$.

(E)-2-(3-methoxy-4-(methoxymethoxy)styryl)-N,N,5-trimethylbenzo[d]thiazol-6-amine (18e)

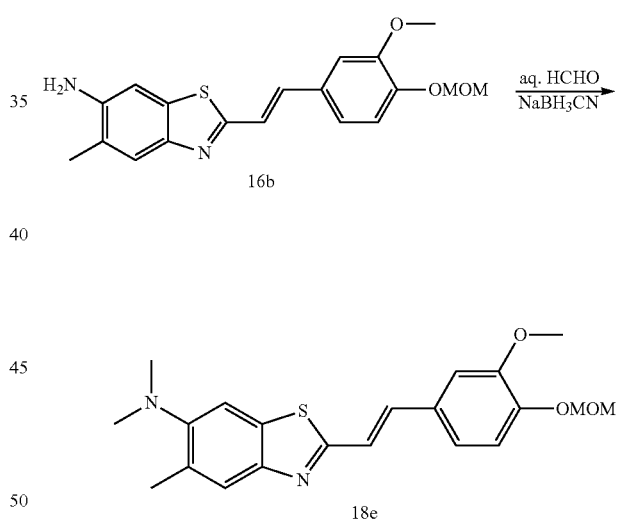

To a solution of 16b (580 mg, 1.64 mmol) in MeOH (20 mL) was added formaldehyde solution (738 mg, 9.84 mmol, 40 wt. % in water) and sodium cyanoborohydride (310 mg, 4.92 mmol) at 0° C. The mixture was stirred at room temperature overnight under nitrogen atmosphere. The suspension was concentrated and the residue was purified by silica gel column chromatography using 25% ethyl acetate in petroleum ether as eluent to give 18e (220 mg, 35% yield) as a yellow solid. $^1$H NMR (400 MHz, DMSO-$d_6$): δ 7.72 (s, 1H), 7.67 (s, 1H), 7.51 (d, J=16.4 Hz, 1H), 7.46 (d, J=16.4 Hz, 1H), 7.44 (d, J=1.6 Hz, 1H), 7.24 (dd, J=8.4, 1.6 Hz, 1H), 7.09 (d, J=8.4 Hz, 1H), 5.20 (s, 2H), 3.86 (s, 3H), 3.40 (s, 3H), 2.70 (s, 6H), 2.39 (s, 3H); MS (ESI) m/z 385.0 [M+H]$^+$.

(E)-tert-butyl ethyl(2-(3-methoxy-4-(methoxymethoxy)styryl)-5-methylbenzo[d]thiazol-6-yl)carbamate (18f)

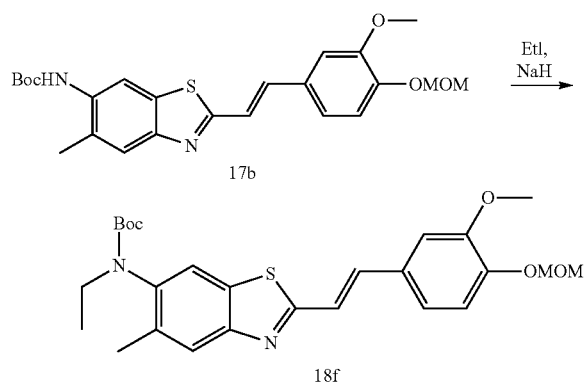

To a suspension of sodium hydride (252 mg, 6.30 mmol, 60% suspension in mineral oil) in anhydrous THF (20 mL) was added 17b (820 mg, 1.80 mmol) at 0° C. The mixture was stirred for 10 min before ethyl iodide (982 mg, 6.30 mmol) was added at 0° C. under nitrogen. The reaction was stirred at room temperature for 1 h, quenched with saturated ammonium chloride aqueous solution (5 mL) and extracted with ethyl acetate (3×20 mL). The organic layers were combined, dried over anhydrous Na$_2$SO$_4$ and filtered. The filtrate was concentrated and the residue was purified by silica gel column chromatography using 30% ethyl acetate in petroleum ether as eluent to give 18f (675 mg, 77% yield) as a yellow solid. MS (ESI) m/z 485.0 [M+H]$^+$.

(E)-tert-butyl (2-(3-bromo-4-(methoxymethoxy)styryl)-5-methylbenzo[d]thiazol-6-yl)(methyl)carbamate (18g)

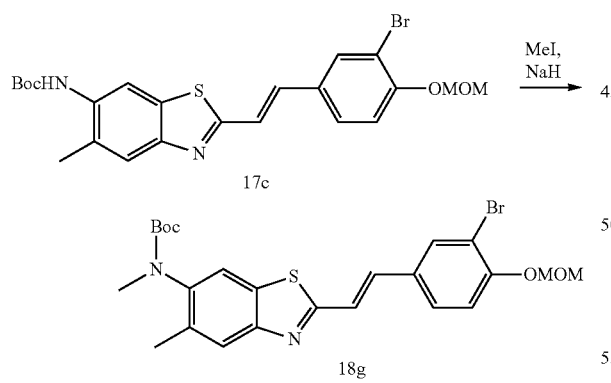

To a suspension of sodium hydride (98 mg, 2.43 mmol, 60% suspension in mineral oil) in anhydrous THF (20 mL) was added 17c (490 mg, 0.97 mmol) at 0° C. The mixture was stirred for 15 min before methyl iodide (345 mg, 2.45 mmol) was added at 0° C. under nitrogen. The reaction was stirred at room temperature overnight, quenched with saturated ammonium chloride aqueous solution (5 mL) and extracted with ethyl acetate (3×30 mL). The organic layers were combined, dried over anhydrous Na$_2$SO$_4$ and filtered. The filtrate was concentrated and the residue was purified by silica gel column chromatography using 30% ethyl acetate in petroleum ether as eluent to give 18 g (450 mg, 89% yield) as yellow oil. MS (ESI) m/z 518.9 and 520.9 [M+H]$^+$.

(E)-2-(3-bromo-4-(methoxymethoxy)styryl)-N,N,5-trimethylbenzo[d]thiazol-6-amine (18h)

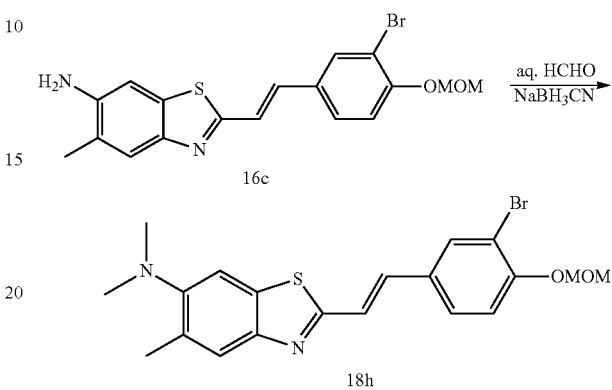

To a solution of 16c (800 mg, 1.98 mmol) in MeOH (30 mL) was added formaldehyde solution (893 mg, 11.9 mmol, 40 wt. % in water) and sodium cyanoborohydride (374 mg, 5.94 mmol) at 0° C. The mixture was stirred at room temperature overnight under nitrogen atmosphere.

The suspension was concentrated and the residue was purified by silica gel column chromatography using 25% ethyl acetate in petroleum ether as eluent to give 18h (190 mg, 22% yield) as a yellow solid. $^1$H NMR (400 MHz, DMSO-d$_6$): δ 8.04 (d, J=2.0 Hz, 1H), 7.75 (d, J=2.0 Hz, 1H), 7.73 (s, 1H), 7.68 (s, 1H), 7.52 (d, J=16.4 Hz, 1H), 7.47 (d, J=16.4 Hz, 1H), 7.25 (d, J=8.4 Hz, 1H), 5.34 (s, 2H), 3.43 (s, 3H), 2.70 (s, 6H), 2.39 (s, 3H); MS (ESI) m/z 432.8 and 434.8 [M+H]$^+$.

(E)-tert-butyl (2-(3-bromo-4-(methoxymethoxy)styryl)-5-methylbenzo[d]thiazol-6-yl)(ethyl)carbamate (18i)

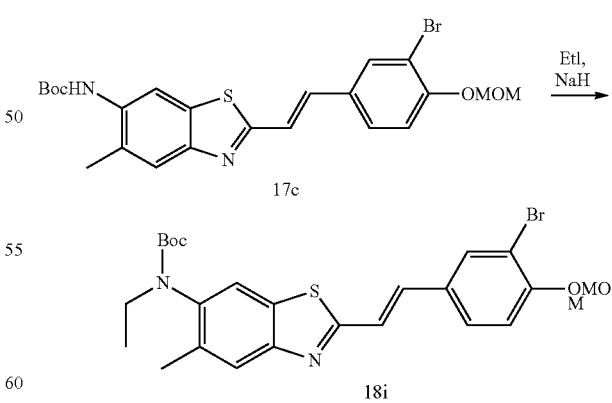

To a suspension of sodium hydride (180 mg, 4.50 mmol, 60% suspension in mineral oil) in anhydrous THF (30 mL) was added 17c (770 mg, 1.52 mmol) at 0° C. The mixture was stirred for 15 min before ethyl iodide (702 mg, 4.50 mmol) was added at 0° C. under nitrogen. The reaction was stirred at room temperature overnight, quenched with saturated ammonium chloride aqueous solution (5 mL) and extracted with ethyl acetate (3×30 mL). The organic layers were combined, dried over anhydrous $Na_2SO_4$ and filtered. The filtrate was concentrated and the residue was purified by silica gel column chromatography using 30% ethyl acetate in petroleum ether as eluent to give 18i (670 mg, 83% yield) as a yellow oil. $^1$H NMR (400 MHz, DMSO-$d_6$): δ 8.08 (d, J=2.0 Hz, 1H), 7.90 (br s, 1H), 7.86 (s, 1H), 7.78 (dd, J=8.8, 2.0 Hz, 1H), 7.57 (s, 2H), 7.26 (d, J=8.8 Hz, 1H), 5.31 (s, 2H), 3.72-3.60 (m, 1H), 3.54-3.42 (m, 1H), 3.42 (s, 3H), 2.28 (s, 3H), 1.48 (br s, 3H), 1.27 (br s, 6H), 1.14-1.00 (m, 3H); MS (ESI) m/z 532.8 and 534.8 [M+H]$^+$.

(E)-2-bromo-4-(2-(6-(methylamino)benzo[d]thiazol-2-yl)vinyl)phenol (EU-004-01B)

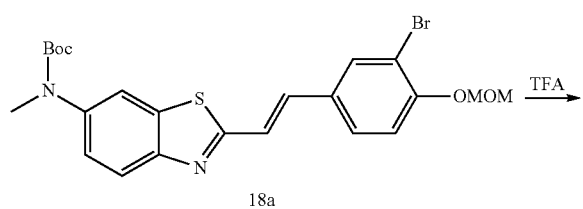

18a

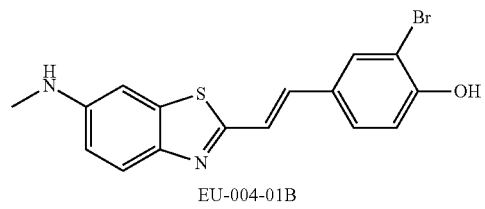

EU-004-01B

To a solution of 18a (1.0 g, 1.98 mmol) in $CH_2Cl_2$ (4 mL) was added trifluoroacetic acid (4 mL) at 0° C. The mixture was stirred at 0° C. for 2 h under nitrogen atmosphere. The reaction was concentrated under low temperature and the residue was neutralized to pH=7 with saturated $NaHCO_3$ aqueous solution, then extracted with ethyl acetate (2×30 mL). The organic layers were combined and concentrated to give a residue, which was purified by preparative HPLC to afford EU-004-01B as a yellow solid (105 mg, 15% yield). $^1$H NMR (400 MHz, DMSO-$d_6$): δ 10.62 (br s, 1H), 7.88 (s, 1H), 7.62 (d, J=8.4 Hz, 1H), 7.56 (d, J=8.4 Hz, 1H), 7.33 (d, J=16.0 Hz, 1H), 7.27 (d, J=16.0 Hz, 1H), 6.99-6.96 (m, 2H), 6.77 (d, J=8.4 Hz, 1H), 6.09 (q, J=4.0 Hz, 1H), 2.74 (d, J=4.0 Hz, 3H); MS (ESI) m/z 360.8 and 362.8 [M+H]$^+$.

(E)-2-bromo-4-(2-(6-(dimethylamino)benzo[d]thiazol-2-yl)vinyl)phenol (EU-004-02B)

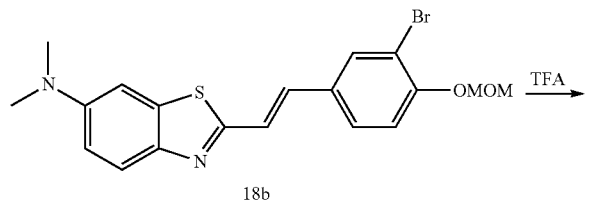

18b

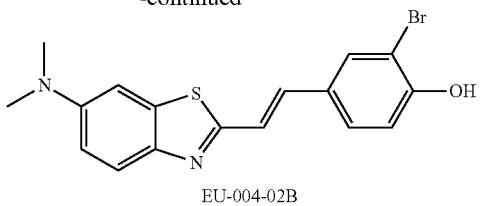

EU-004-02B

To a solution of 18b (667 mg, 1.62 mmol) in $CH_2Cl_2$ (10 mL) was added trifluoroacetic acid (5 mL) at 0° C. The mixture was stirred at 0° C. for 3 h under nitrogen atmosphere. The reaction mixture was neutralized to pH=7 with saturated $NaHCO_3$ aqueous solution, then extracted with ethyl acetate (3×30 mL). The organic layers were combined and concentrated to give a residue, which was purified by preparative HPLC then crystallized in $CH_2Cl_2$ (2 mL) to afford EU-004-02B as a yellow solid (200 mg, 33% yield). $^1$H NMR (400 MHz, DMSO-$d_6$): δ 10.63 (s, 1H), 7.89 (d, J=2.0 Hz, 1H), 7.72 (d, J=8.8 Hz, 1H), 7.58 (dd, J=8.4, 2.4 Hz, 1H), 7.36 (d, J=16.0 Hz, 1H), 7.31 (d, J=16.0 Hz, 1H), 7.26 (d, J=2.8 Hz, 1H), 6.98 (d, J=8.4 Hz, 1H), 6.96 (dd, J=8.4, 2.8 Hz, 1H), 2.99 (s, 6H); MS (ESI) m/z 374.8 and 376.8 [M+H]$^+$.

(E)-2-bromo-4-(2-(6-(ethylamino)benzo[d]thiazol-2-yl)vinyl)phenol (EU-004-03B)

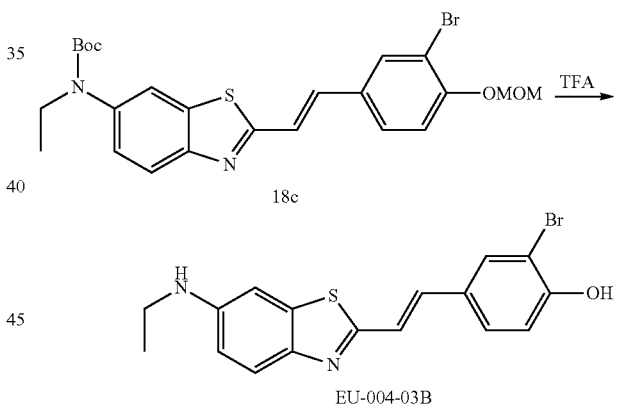

To a solution of 18c (430 mg, 0.829 mmol) in $CH_2Cl_2$ (3 mL) was added trifluoroacetic acid (2 mL) at 0° C. The mixture was stirred at 0° C. for 3 h under nitrogen atmosphere. The reaction mixture was neutralized to pH=7 with saturated $NaHCO_3$ aqueous solution, then extracted with ethyl acetate (3×30 mL). The organic layers were combined and concentrated to give a residue, which was purified by preparative HPLC then crystallized in $CH_2Cl_2$ (2 mL) to afford EU-004-03B as a yellow solid (120 mg, 39% yield). $^1$H NMR (400 MHz, DMSO-$d_6$): δ 10.62 (br s, 1H), 7.88 (s, 1H), 7.61 (d, J=8.8 Hz, 1H), 7.56 (d, J=7.6 Hz, 1H), 7.33 (d, J=16.0 Hz, 1H), 7.27 (d, J=16.0 Hz, 1H), 7.01 (s, 1H), 6.97 (d, J=8.4 Hz, 1H), 6.78 (dd, J=8.8, 2.0 Hz, 1H), 5.98 (t, J=4.8 Hz, 1H), 3.13-3.05 (m, 2H), 1.19 (t, J=6.8 Hz, 3H); MS (ESI) m/z 374.8 and 376.8 [M+H]$^+$.

(E)-2-bromo-4-(2-(6-(ethylamino)benzo[d]thiazol-2-yl)vinyl)phenol (EU-005-01A)

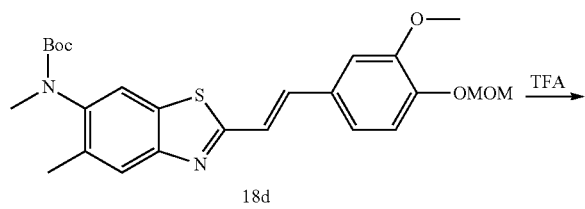

To a solution of 18d (575 mg, 1.22 mmol) in CH$_2$Cl$_2$ (2 mL) was added trifluoroacetic acid (2 mL) at 0° C. The mixture was stirred at 0° C. for 3 h under nitrogen atmosphere. The reaction mixture was neutralized to pH=7 with saturated NaHCH$_3$ aqueous solution, then extracted with ethyl acetate (3×30 mL). The organic layers were combined and concentrated to give a residue, which was purified by silica gel column chromatography using 30% ethyl acetate in petroleum ether as eluent then crystallized in CH$_2$Cl$_2$ (2 mL) to afford EU-005-01A as a yellow solid (110 mg, 28% yield). $^1$H NMR (400 MHz, DMSO-d$_6$): δ 9.37 (s, 1H), 7.54 (s, 1H), 7.35-7.31 (m, 2H), 7.27 (d, J=16.0 Hz, 1H), 7.10 (dd, J=8.0, 1.6 Hz, 1H), 6.97 (s, 1H), 6.79 (d, J=8.0 Hz, 1H), 5.42 (q, J=4.8 Hz, 1H), 3.84 (s, 3H), 2.80 (d, J=4.8 Hz, 3H), 2.20 (s, 3H); MS (ESI) m/z 326.9 [M+H]$^+$.

(E)-4-(2-(6-(dimethylamino)-5-methylbenzo[d]thiazol-2-yl)vinyl)-2-methoxyphenol (EU-005-02A)

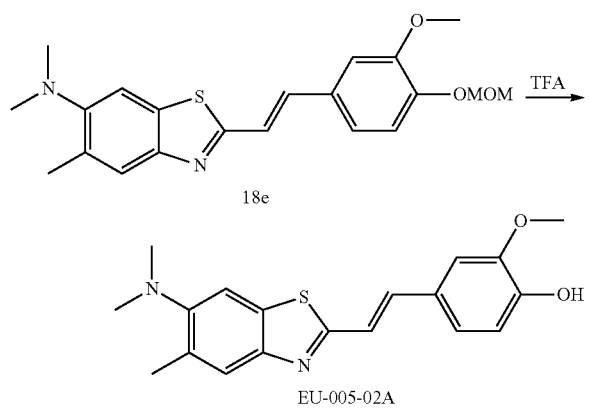

To a solution of 18e (220 mg, 0.573 mmol) in CH$_2$Cl$_2$ (2 mL) was added trifluoroacetic acid (2 mL) at 0° C. The mixture was stirred at 0° C. for 3 h under nitrogen atmosphere. The reaction mixture was neutralized to pH=7 with saturated NaHCH$_3$ aqueous solution, then extracted with ethyl acetate (3×30 mL). The organic layers were combined and concentrated to give a residue, which was purified by preparative HPLC then crystallized in CH$_2$Cl$_2$ (2 mL) to afford EU-005-02A as a yellow solid (110 mg, 56% yield). $^1$H NMR (400 MHz, DMSO-d$_6$): δ 9.45 (s, 1H), 7.70 (s, 1H), 7.66 (s, 1H), 7.43 (d, J=16.4 Hz, 1H), 7.38 (d, J=16.4 Hz, 1H), 7.37 (d, J=2.0 Hz, 1H), 7.14 (dd, J=8.0, 2.0 Hz, 1H), 6.81 (d, J=8.4 Hz, 1H), 3.85 (s, 3H), 2.70 (s, 6H), 2.39 (s, 3H); MS (ESI) m/z 341.0 [M+H]$^+$.

(E)-4-(2-(6-(ethylamino)-5-methylbenzo[d]thiazol-2-yl)vinyl)-2-methoxyphenol (EU-005-03A)

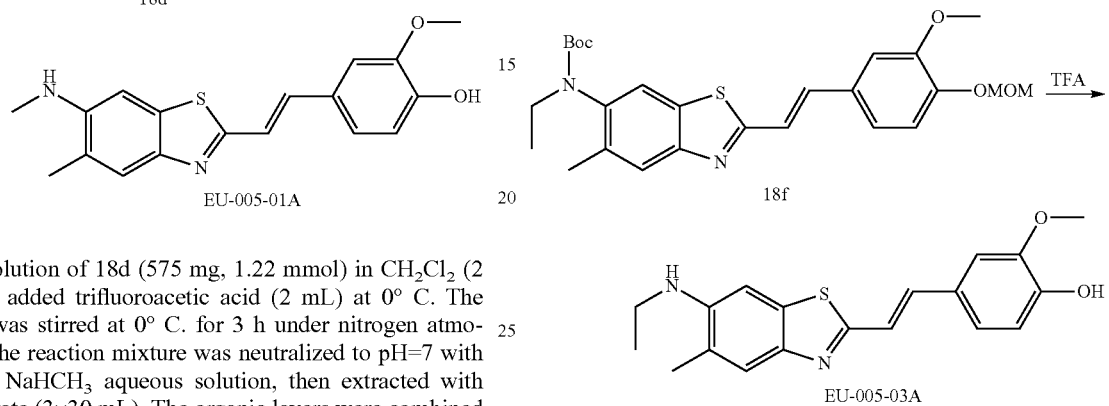

To a solution of 18f (675 mg, 1.39 mmol) in CH$_2$Cl$_2$ (2 mL) was added trifluoroacetic acid (2 mL) at 0° C. The mixture was stirred at this temperature for 3 h under nitrogen atmosphere. The reaction mixture was neutralized to pH=7 with saturated NaHCH$_3$ aqueous solution, then extracted with ethyl acetate (3×30 mL). The organic layers were combined and concentrated to give a residue, which was purified by preparative HPLC then crystallized in CH$_2$Cl$_2$ (2 mL) to afford EU-005-03A as a yellow solid (124 mg, 26% yield). $^1$H NMR (400 MHz, DMSO-d$_6$): δ 9.73 (br s, 1H), 7.54 (s, 1H), 7.33 (d, J=16.4 Hz, 1H), 7.32 (d, J=2.0 Hz, 1H), 7.27 (d, J=16.0 Hz, 1H), 7.10 (dd, J=8.0, 2.0 Hz, 1H), 7.04 (s, 1H), 6.79 (d, J=8.4 Hz, 1H), 5.10 (br s, 1H), 3.84 (s, 3H), 3.18 (q, J=7.2 Hz, 2H), 2.21 (s, 3H), 1.24 (t, J=7.2 Hz, 3H); MS (ESI) m/z 341.0 [M+H]$^+$.

(E)-2-bromo-4-(2-(5-methyl-6-(methylamino)benzo[d]thiazol-2-yl)vinyl)phenol (EU-005-01B)

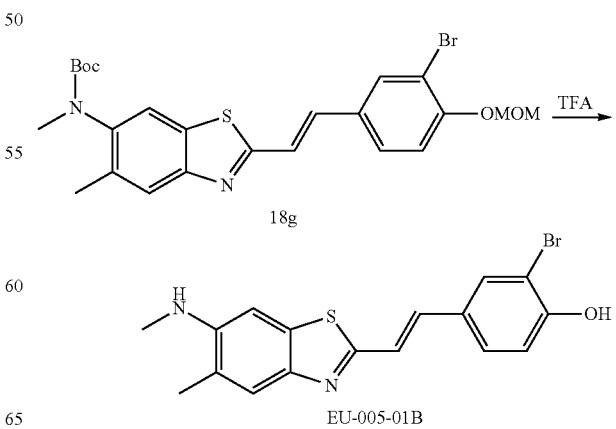

To a solution of 18 g (450 mg, 0.867 mmol) in CH$_2$Cl (2 mL) was added trifluoroacetic acid (2 mL) at 0° C. The mixture was stirred at this temperature for 3 h under nitrogen atmosphere. The reaction mixture was neutralized to pH=7 with saturated NaHCO$_3$ aqueous solution, then extracted with ethyl acetate (3×100 mL). The organic layers were combined and concentrated to give a residue, which was washed with ethyl acetate (3×5 mL) then crystallized in MeOH and CH$_2$Cl$_2$ (1/1, 3 mL) for 2 times to afford EU-005-01B as a yellow solid (120 mg, 37% yield). $^1$H NMR (400 MHz, DMSO-d$_6$): δ 10.60 (s, 1H), 7.87 (d, J=1.6 Hz, 1H), 7.57-7.55 (m, 2H), 7.33 (d, J=16.4 Hz, 1H), 7.27 (d, J=16.4 Hz, 1H), 6.98-6.96 (m, 2H), 5.45 (q, J=4.8 Hz, 1H), 2.80 (d, J=4.8 Hz, 3H), 2.19 (s, 3H); MS (ESI) m/z 374.9 and 376.9 [M+H]$^+$.

(E)-2-bromo-4-(2-(6-(dimethylamino)-5-methyl-benzo[d]thiazol-2-yl)vinyl)phenol (EU-005-02B)

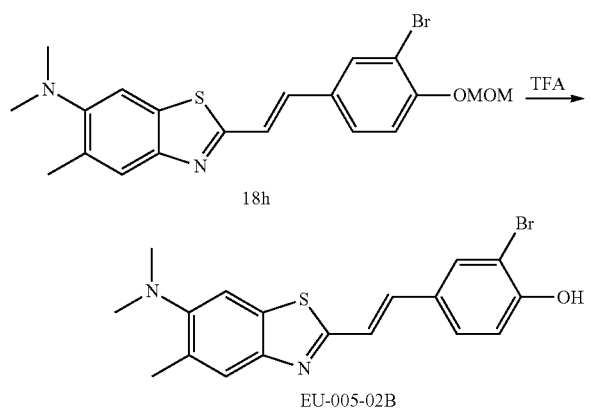

To a solution of 18h (190 mg, 0.439 mmol) in CH$_2$Cl$_2$ (2 mL) was added trifluoroacetic acid (2 mL) at 0° C. The mixture was stirred at 0° C. for 3 h under nitrogen atmosphere. The reaction mixture was neutralized to pH=7 with saturated NaHCO$_3$ aqueous solution, then extracted with ethyl acetate (3×30 mL). The organic layers were combined and concentrated to give a residue, which was purified by preparative HPLC then crystallized in CH$_2$Cl$_2$ (2 mL) to afford EU-005-02B as a yellow solid (119 mg, 69% yield). $^1$H NMR (400 MHz, DMSO-d$_6$): δ 10.68 (s, 1H), 7.92 (d, J=2.0 Hz, 1H), 7.71 (s, 1H), 7.66 (s, 1H), 7.60 (dd, J=8.4, 2.0 Hz, 1H), 7.43 (d, J=16.0 Hz, 1H), 7.38 (d, J=16.0 Hz, 1H), 6.98 (d, J=8.4 Hz, 1H), 2.69 (s, 6H), 2.38 (s, 3H); MS (ESI) m/z 388.9, 390.9 [M+H]$^+$.

(E)-2-bromo-4-(2-(6-(ethylamino)-5-methylbenzo[d]thiazol-2-yl)vinyl)phenol (EU-005-03B)

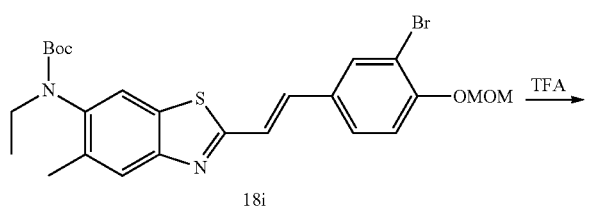

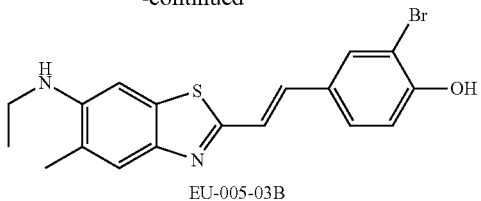

To a solution of 18i (670 mg, 1.26 mmol) in CH$_2$Cl$_2$ (2 mL) was added trifluoroacetic acid (2 mL) at 0° C. The mixture was stirred at 0° C. for 3 h under nitrogen atmosphere. The reaction mixture was neutralized to pH=7 with saturated NaHCO$_3$ aqueous solution, then extracted with ethyl acetate (4×100 mL). The organic layers were combined and concentrated to give a residue, which was washed with ethyl acetate (3×5 mL) then crystallized from MeOH and CH$_2$Cl$_2$ (1/1, 3 mL) for 2 times to afford EU-005-03B as a yellow solid (160 mg, 33% yield). $^1$H NMR (400 MHz, DMSO-d$_6$): δ 10.61 (s, 1H), 7.87 (d, J=1.6 Hz, 1H), 7.57-7.55 (m, 2H), 7.33 (d, J=16.4 Hz, 1H), 7.27 (d, J=16.4 Hz, 1H), 7.04 (s, 1H), 6.97 (d, J=8.4 Hz, 1H), 5.13 (t, J=4.8 Hz, 1H), 3.21-3.14 (m, 2H), 2.21 (s, 3H), 1.24 (t, J=7.2 Hz, 3H); MS (ESI) m/z 388.9 and 390.9 [M+H]$^+$.

2,5-dimethyl-6-nitrobenzo[d]thiazole (2)

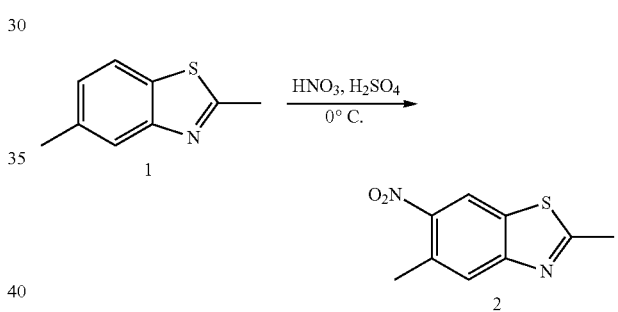

To a solution of 1 (37.9 g, 232.5 mmol) in concentrated H$_2$SO$_4$ (226 mL) was added fuming HNO$_3$ (21 mL) slowly at 0° C. The mixture was stirred at 0° C. for 2 h under nitrogen atmosphere. After the reaction was completed, the reaction mixture was poured into ice-water (2.0 L). The precipitate was collected by filtration and the filter cake was washed with saturated aqueous sodium bicarbonate (3×1.5 L) and water (2×1.5 L) to give the crude product, which was purified by silica gel column chromatography using 5% ethyl acetate in petroleum ether as eluent to afford 2 as a yellow solid (18.4 g, 38% yield). $^1$H NMR (400 MHz, CDCl$_3$): δ 8.52 (s, 1H), 7.85 (s, 1H), 2.88 (s, 3H), 2.50 (s, 3H). MS (ESI) m/z 208.8 [M+H]$^+$.

2-bromo-4-(2-(5-methyl-6-nitrobenzo[d]thiazol-2-yl)vinyl)phenol (3)

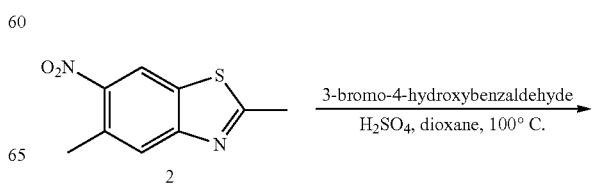

63
-continued

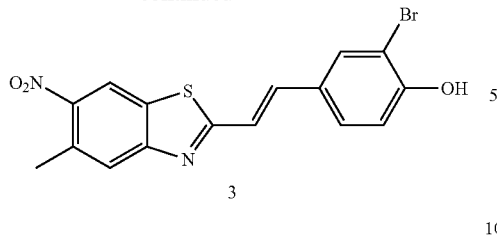

To a solution of 2 (18.0 g, 86.5 mmol) and 3-bromo-4-hydroxybenzaldehyde (19.1 g, 95.2 mmol) in dioxane (500 mL) was added concentrated $H_2SO_4$ (9.3 g, 95.2 mmol) at room temperature. The mixture was stirred at 100° C. overnight under nitrogen atmosphere. After the reaction was completed, the reaction mixture was cooling down to room temperature. The precipitate was collected by filtration and the filter cake was washed with saturated $NaHCO_3$ aqueous solution (3×400 mL) and water (2×400 mL). The solid was dried under high vacuum to afford 3 as a yellow solid (29.9 g, 88.5% yield). $^1$H NMR (400 MHz, DMSO-$d_6$): δ 10.86 (s, 1H), 8.88 (s, 1H), 8.01-7.98 (m, 1H), 7.70-7.50 (m, 3H), 7.01 (d, J=8.4 Hz, 1H), 2.64 (s, 3H). MS (ESI) m/z 390.8, 392.8 [M+H]$^+$.

2-(3-bromo-4-(methoxymethoxy)styryl)-5-methyl-6-nitrobenzo[d]thiazole (4)

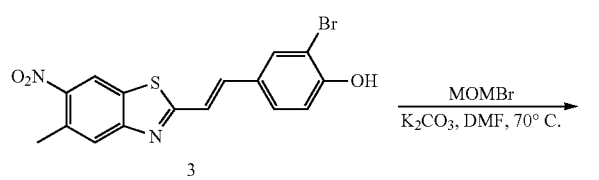

To a solution of 3 (29.8 g, 76.2 mmol) in DMF (1.0 L) was added $K_2CO_3$ (31.5 g, 228.6 mmol) and methoxymethyl bromide (19.1 g, 152.4 mmol) at 0° C. The reaction mixture was stirred at room temperature overnight under nitrogen atmosphere. The reaction mixture was concentrated, and the residue was suspended in water (400 mL). The solid was collected by filtration and the filter cake was washed with water (3×1.0 L) to give 4 as a brown solid (30.9 g, 93.2% yield). $^1$H NMR (400 MHz, DMSO-$d_6$): δ 8.91 (s, 1H), 8.13 (d, J=2.0 Hz, 1H), 8.03 (s, 1H), 7.81 (dd, J=8.4, 2.0 Hz, 1H), 7.74-7.54 (m, 2H), 7.28 (d, J=8.8 Hz, 1H), 5.36 (s, 2H), 3.43 (s, 3H), 2.65 (s, 3H). MS (ESI) m/z 434.8, 436.8 [M+H]$^+$.

64

2-(3-bromo-4-(methoxymethoxy)styryl-5-methyl-benzo[d]thiazol-6-amine (5)

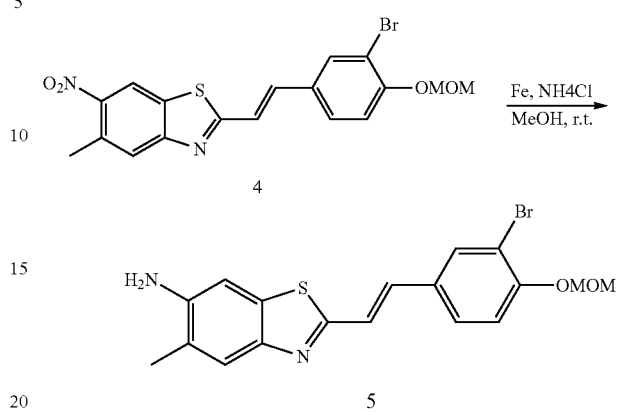

To a suspension of 4 (29.6 g, 68.2 mmol) in MeOH (880 mL) was added and ammonium chloride (18.2 g, 341.0 mmol) and iron powder (19.1 g, 341.0 mmol). The mixture was stirred room temperature for 16 h. The suspension was filtered and the filter cake was washed with $CH_2Cl_2$ (2×700 mL) and MeOH (2×700 mL). The filtrate was concentrated, and the residue was washed with water (3×700 mL). The wet material was dried under vacuum to afford 5 as a yellow solid (20.6 g, 74.7% yield). MS (ESI) m/z 404.8, 406.8 [M+H]$^+$.

2-(3-bromo-4-(methoxymethoxy)styryl)-N,5-dimethylbenzo[d]thiazol-6-amine (Compound A)

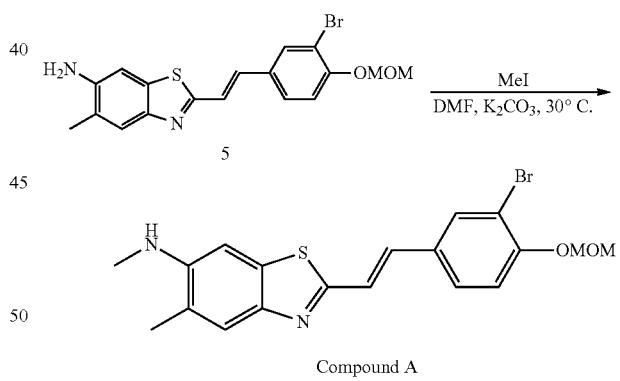

To a mixture of 5 (6.6 g, 16.2 mmol) and $K_2CO_3$ (2.1 g, 32.5 mmol) in DMF (65 mL) was added methyl iodide (1.5 g, 10.7 mmol) at room temperature under nitrogen. The result mixture was heated at 30° C. for 16 h. The reaction mixture was concentrated, and the residue was diluted with water (500 mL). The solid was collected by filtration and the filter cake was washed with water (2×500 mL) to give a crude. The crude was purified by prep-HPLC (30-100% MeCN in water) to give 2-(3-bromo-4-(methoxymethoxy)styryl)-N,5-dimethylbenzo[d]thiazol-6-amine as a yellow solid (2.1 g, 31% yield). $^1$H NMR (400 MHz, DMSO-$d_6$): δ 8.00 (s, 1H), 7.70 (d, J=8.4 Hz, 1H), 7.57 (s, 1H), 7.45 (d, J=16.0 Hz, 1H), 7.32 (d, J=16.0 Hz, 1H), 7.23 (d, J=16.4 Hz, 1H), 6.89 (s, 1H), 5.50 (s, 1H), 5.34 (s, 2H), 3.41 (s, 3H), 2.80 (s, 3H), 2.20 (s, 3H). MS (ESI) m/z 434.8, 436.8 [M+H]+.

To a mixture of 2-(3-bromo-4-(methoxymethoxy)styryl)-N,5-dimethylbenzo[d]thiazol-6-amine (2.1 g, 7.2 mmol) in 2-iodoethanol (8.5 mL) was added triethylamine (3.9 mL). The result mixture was stirred for 8.5 h at 60° C. under nitrogen. The reaction mixture was concentrated, and the residue was diluted with water and extracted with DCM. The organic phase was washed with brine, dried over anhydrous Na$_2$SO$_4$ and concentrated. The residue was purified by prep-HPLC (20-80% MeCN in water) to give 2-((2-(3-bromo-4-(methoxymethoxy)styryl)-5-methylbenzo[d]thiazol-6-yl)(methyl)amino)ethanol (1.05 g, 45% yield) as a yellow solid. MS (ESI) m/z 462.9, 464.9 [M+H]+.

2-((2-(3-bromo-4-(methoxymethoxy)styryl)-5-methylbenzo[d]thiazol-6-yl)(methyl)amino)ethanol (7)

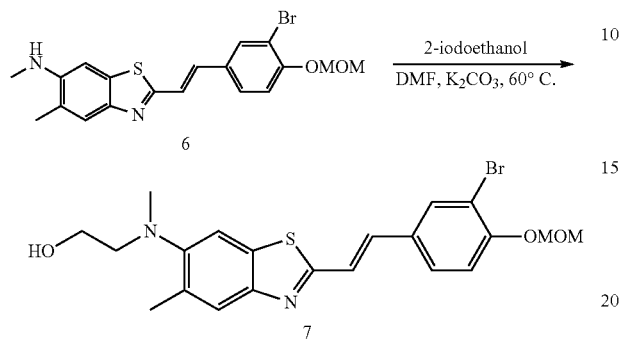

2-(3-bromo-4-(methoxymethoxy)styryl)-N-(2-(2-fluoroethoxy)ethyl)-N,5-dimethylbenzo[d]thiazol-6-amine (Compound D)

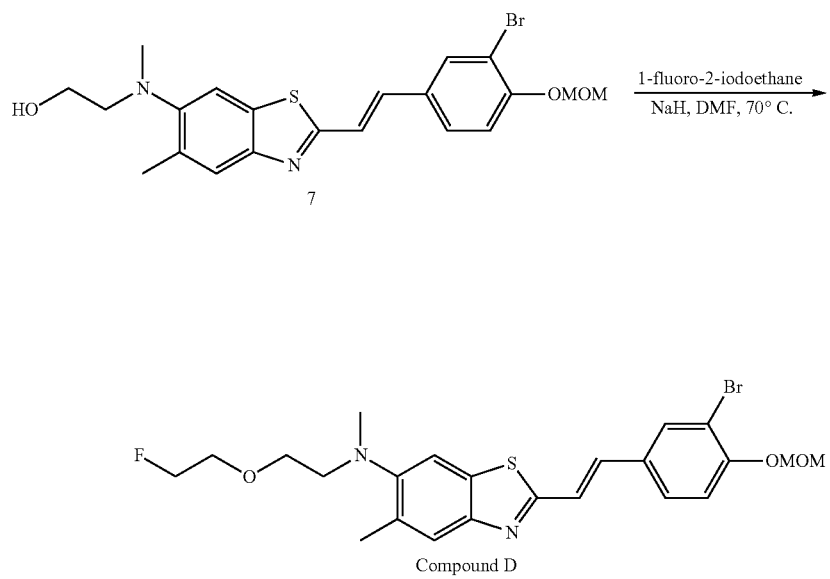

To a solution of 7 (1.0 g, 2.05 mmol) in DMF (16 mL) was added NaH (60% in mineral oil, 194 mg, 4.92 mmol) at 0° C. nitrogen atmosphere. The mixture was stirred at 40° C. for 1.5 h. Then 1-fluoro-2-iodoethane (1.07 g, 6.15 mmol) was added. The result mixture was stirred at 70° C. for 16 h. The reaction mixture was quenched with water and extracted with DCM. The organic layers were combined was washed with brine, dried over anhydrous Na$_2$SO$_4$ and concentrated. The residue was purified by prep-HPLC (20-60% MeCN in water) to give 2-(3-bromo-4-(methoxymethoxy)styryl)-N-(2-(2-fluoroethoxy)ethyl)-N,5-dimethylbenzo[d]thiazol-6-amine (102.5 mg pure+240 mg of 90% purity, 16.0% yield) as a yellow solid. $^1$H NMR (400 MHz, DMSO-d$_6$): δ 8.05 (s, 1H), 7.77-7.74 (m, 3H), 7.55-7.50 (m, 2H), 7.25 (d, J=8.0 Hz, 1H), 5.34 (s, 2H), 4.55 (dd, J=8.0, 4.0 Hz, 1H), 4.43 (dd, J=8.0, 4.0 Hz, 1H), 3.66 (dd, J=8.0, 4.0 Hz, 1H), 3.63-3.57 (m, 3H), 3.43 (s, 4H), 3.11 (s, 2H), 2.76 (s, 3H), 2.37 (s, 3H). MS (ESI) m/z 508.9 and 510.9 [M+H]+.

2-bromo-4-(2-(6-((2-(2-fluoroethoxy)ethyl)(methyl)amino)-5-methylbenzo[d]thiazol-2-yl)vinyl)phenol (Compound B)

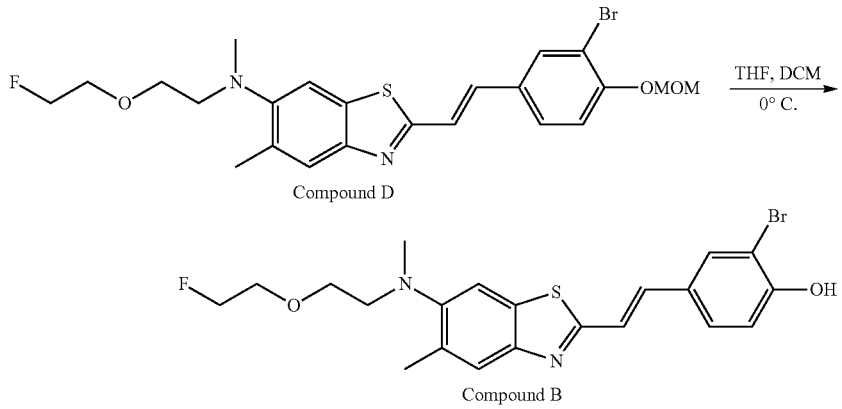

To a solution of (E)-2-(3-bromo-4-(methoxymethoxy)styryl)-N-(2-(2-fluoroethoxy)ethyl)-N,5-dimethylbenzo[d]thiazol-6-amine (240 mg, 90% purity, 0.42 mmol) in DCM (26.0 mL) was added TFA (5.3 mL) at 0° C. nitrogen atmosphere. The mixture was stirred at 0° C. for 5 h. The reaction mixture was neutralized to pH 7 with saturated aqueous NaHCO$_3$ solution and extracted with DCM. The organic layers were combined was washed with brine, dried over anhydrous Na$_2$SO$_4$ and concentrated. The residue was purified by prep-HPLC to give 2-bromo-4-(2-(6-((2-(2-fluoroethoxy)ethyl)(methyl)amino)-5-methylbenzo[d]thiazol-2-yl)vinyl)phenol (130 mg, 66.6% yield) as a yellow solid. $^1$H NMR (400 MHz, DMSO-d$_6$): δ 10.71 (s, 1H), 7.93 (d, J=2.0 Hz, 1H), 7.73 (d, J=8.4 Hz, 2H), 7.61 (d, J=8.8, 2.4 Hz, 1H), 7.42 (d, J=7.6 Hz, 2H), 6.98 (d, J=8.4 Hz, 1H), 4.55 (dd, J=8.0, 4.0 Hz, 1H), 4.43 (dd, J=8.0, 4.0 Hz, 1H), 3.68-3.57 (m, 4H), 3.11-3.08 (m, 2H), 2.75 (s, 3H), 2.36 (s, 3H). MS (ESI) m/z 466.9, 464.9 [M+H]$^+$.

2-bromo-4-(2-(6-((2-(2-fluoroethoxy)ethyl)(methyl)amino)-5-methylbenzo[d]thiazol-2-yl)vinyl)phenol

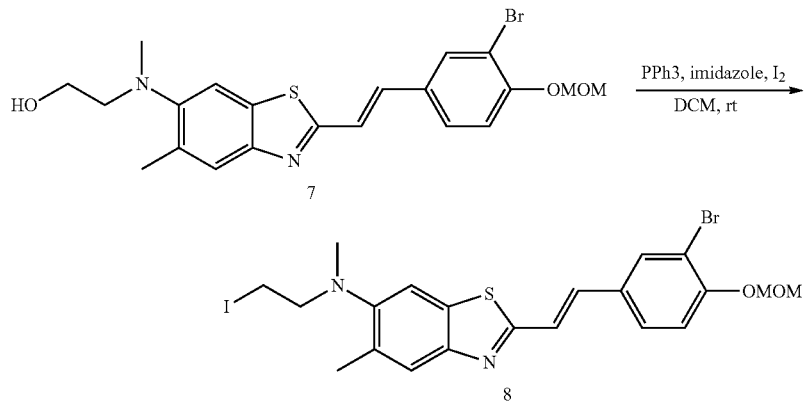

To a solution of PPh$_3$ (1.44 g, 5.51 mmol) and imidazole (374 mg, 5.51 mmol) in DCM (84 mL) was added I2 (1.40 g, 5.51 mmol) at room temperature under nitrogen atmosphere. The result mixture was stirred at room temperature for 35 minutes, then 7 (850 mg, 1.84 mmol) was added. The mixture was stirred at 25° C. for 30 min. The reaction mixture was treated with water and extracted with DCM. The organic layers were combined was washed with brine, dried over anhydrous Na$_2$SO$_4$ and concentrated. The residue was purified by column chromatography on silica gel (petroleum/ethyl acetate=10/1) to give 2-(3-bromo-4-(methoxymethoxy)styryl)-N-(2-iodoethyl)-N,5-dimethylbenzo[d]thiazol-6-amine (743 mg, 71% yield) as a yellow solid. MS (ESI) m z 574.9, 572.9 [M+H]$^+$.

2-(2-((2-(3-bromo-4-(methoxymethoxy)styryl)-5-methylbenzo[d]thiazol-6-yl)(methyl)amino)ethoxy)ethanol (9)

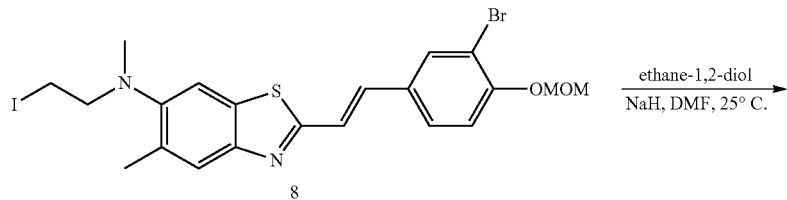

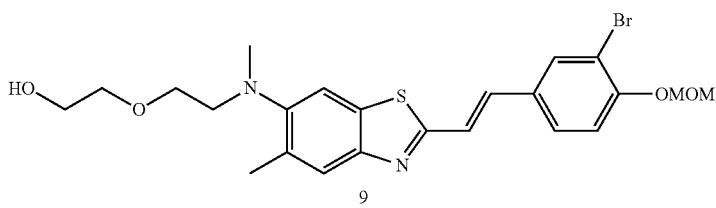

To a mixture of ethane-1,2-diol (241 mg, 3.89 mmol) in dry DMF (32 mL) was added NaH (60% in mineral oil, 78.0 mg, 1.95 mmol) at 0° C. under nitrogen atmosphere. The mixture was stirred at 25° C. for 2 h, then 8 (743 mg, 1.30 mmol) was added. The result mixture was stirred at 25° C. for 16 h. The reaction mixture was quenched with water and extracted with DCM. The organic layers were combined was washed with brine, dried over anhydrous $Na_2SO_4$ and concentrated. The residue was purified by column chromatography on silica gel (petroleum/ethyl acetate=10/1) to give 2-(2-((2-(3-bromo-4-(methoxymethoxy)styryl)-5-methylbenzo[d]thiazol-6-yl)(methyl)amino)ethoxy)ethanol (260 mg, 40.0% yield) as a yellow solid. MS (ESI) m/z 508.9, 506.9 [M+H]$^+$.

2-(2-((2-(3-bromo-4-(methoxymethoxy)styryl)-5-methylbenzo[d]thiazol-6-yl)(methyl)amino)ethoxy) ethyl 4-methylbenzenesulfonate (Compound C)

A mixture of 9 (260 mg, 0.51 mmol) and $Et_3N$ (103 mg, 1.09 mmol) in DCM (5.0 mL) was added TsCl (146 mg, 0.77 mmol) at 0° C. under nitrogen atmosphere. The result mixture was stirred at 25° C. for 16 h. The organic layers were combined was washed with brine, dried over anhydrous $Na_2SO_4$ and concentrated. The residue was purified by column chromatography on silica gel (petroleum/ethyl acetate=5/1) to give 2-(2-((2-(3-bromo-4-(methoxymethoxy)styryl)-5-methylbenzo[d]thiazol-6-yl)(methyl)amino)ethoxy)ethyl 4-methylbenzenesulfonate (167.8 mg, 49.3% yield) as a yellow solid. $^1$H NMR (400 MHz, DMSO-$d_6$): δ 8.06 (s, 1H), 7.79-7.71 (m, 4H), 7.51-7.44 (m, 3H), 7.25 (d, J=8.8 Hz, 1H), 5.34 (s, 2H), 4.10 (dd, J=8.4, 4.4 Hz, 2H), 3.55 (dd, J=8.0, 4.0 Hz, 2H), 3.49 (dd, J=8.0, 4.0 Hz, 2H), 3.42 (s, 3H), 3.10 (s, 2H), 2.70 (s, 3H), 2.38 (s, 3H), 2.22 (s, 3H). MS (ESI) m/z 662.9, 660.9 [M+H]$^+$.

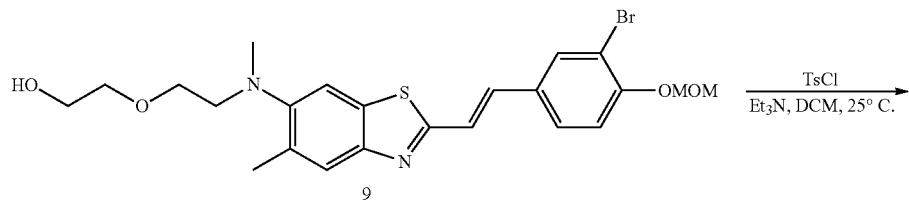

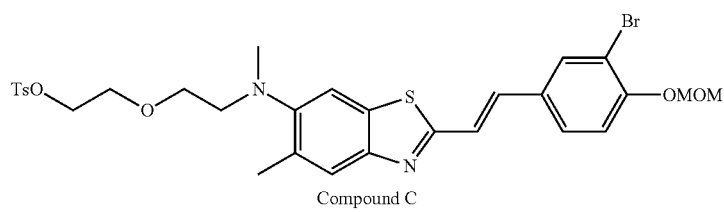

Compound C

(E)-2-(3-bromo-4-methoxystyryl)-5-methyl-6-nitrobenzo[d]thiazole (3)

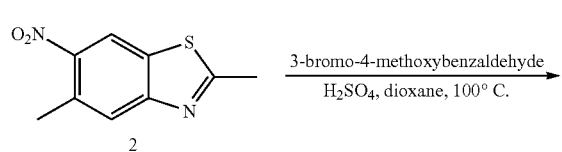
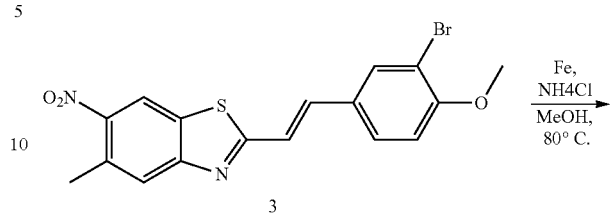

(E)-2-(3-bromo-4-methoxystyryl)-5-methylbenzo[d]thiazol-6-amine (4)

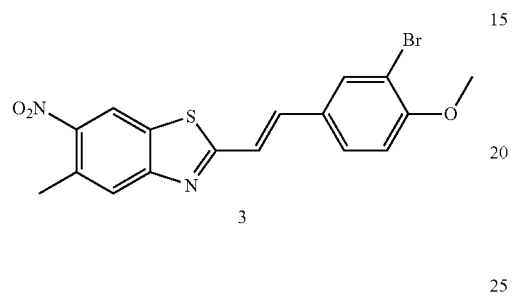
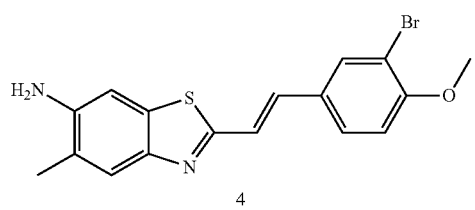

To a solution of 2 (23.9 g, 114.9 mmol) and 3-bromo-4-methoxybenzaldehyde (19.1 g, 184 mmol) in dioxane (720 mL) was added concentrated $H_2SO_4$ (18.0 g, 12.9 mmol) at room temperature. The result mixture was stirred at 100° C. for 3 days under nitrogen atmosphere. After the reaction was completed, the reaction mixture was cooling down to room temperature. The precipitate was collected by filtration and the filter cake was washed with saturated $NaHCO_3$ aqueous solution (3×300 mL) and water (2×300 mL). The solid was dried under high vacuum to afford 3 as a yellow solid (40.0 g, 86% yield). MS (ESI) m/z 404.8, 406.8 [M+H]$^+$.

To a suspension of 3 (40.0 g, 98.8 mmol) in MeOH (1200 mL) was added and ammonium chloride (26.4 g, 493.5 mmol) and iron powder (27.6 g, 492.8 mmol). The result mixture was stirred at 80° C. for 22 h. The suspension was filtered and the filter cake was washed with $CH_2Cl_2$ (3×500 mL) and MeOH (3×500 mL). The filtrate was concentrated, and the residue was washed with water (3×200 mL). The wet material was dried under vacuum to afford 4 as a yellow solid (30.0 g, 81% yield). MS (ESI) m/z 374.8, 376.8 [M+H]$^+$.

(E)-2-(2-((2-(3-bromo-4-methoxystyryl)-5-methylbenzo[d]thiazol-6-yl)amino)ethoxy)ethanol (5)

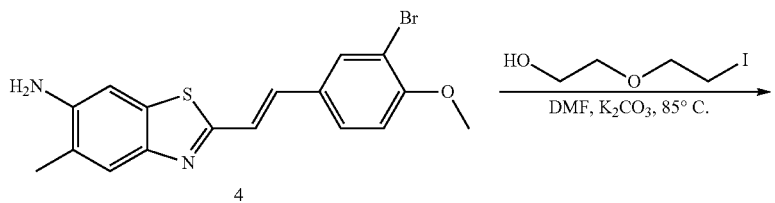

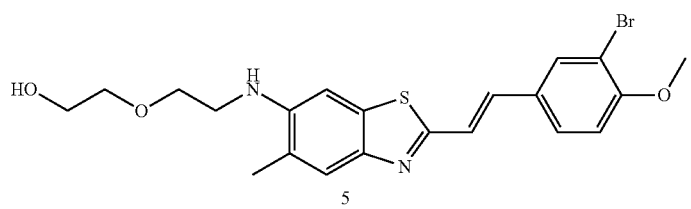

A mixture of 4 (19.1 g, 50.9 mmol), 2-(2-iodoethoxy) ethanol (99.0 g, 458.3 mmol) and K$_2$CO$_3$ (14.1 g, 102.2 mmol) in DMF (380 mL) was heated at 85° C. under nitrogen for 16 h. The reaction mixture was treated with water (900 mL) and extracted with EtOAc (500 mL). The separated organic layer was washed with brine, dried over anhydrous Na$_2$SO$_4$ and concentrated under reduced pressure to give a crude product. The result crude was purified by silica gel column chromatography (PE: EA=20:1 to 1:1) to give 5 as a yellow solid (8.35 g, 36% yield). MS (ESI) m z 462.8, 467.8 [M+H]$^+$.

(E)-2-(2-((2-(3-bromo-4-methoxystyryl)-5-methyl-benzo[d]thiazol-6-yl)(methyl)amino)ethoxy)ethanol (6)

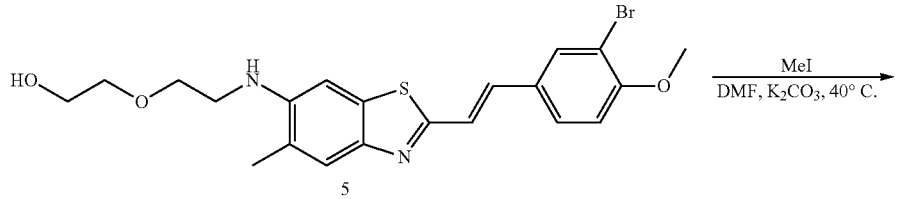

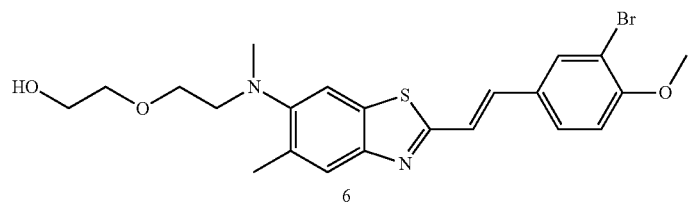

To a mixture of 5 (8.30 g, 17.9 mmol) and K$_2$CO$_3$ (4.94 g, 35.8 mmol) in DMF (83 mL) was added MeI (5.09 g, 35.8 mmol) at 0° C. The reaction mixture was stirred at 30° C. for 16 h. The reaction mixture was diluted with EtOAc (1500 mL), washed with brine (3×1 L), dried over anhydrous Na$_2$SO$_4$ and concentrated to give a crude, which was purified by silica gel column chromatography (PE: EA=20:1 to 2:1) to give 6 as a yellow solid (2.70 g, 31% yield). MS (ESI) m z 476.8, 478.8 [M+H]$^+$.

(E)-2-(2-((2-(3-bromo-4-methoxystyryl)-5-methyl-benzo[d]thiazol-6-yl)(methyl)amino)ethoxy)ethyl 4-methylbenzenesulfonate (7)

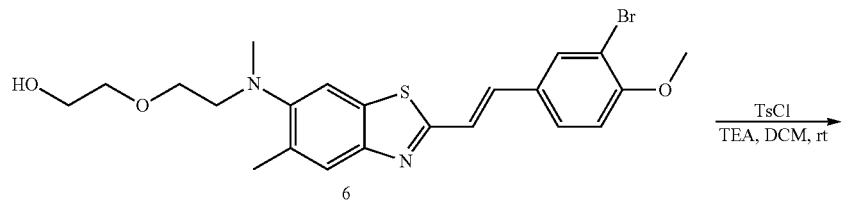

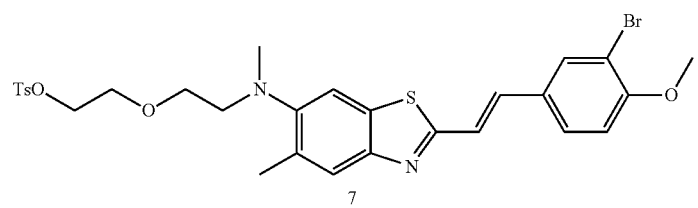

To a mixture of 6 (525 mg, 1.10 mmol) and TEA (555 mg, 5.50 mmol) in dry-DCM (9.9 mL) was added TsCl (627 mg, 3.30 mmol) at 0° C. The reaction mixture was stirred at rt for 6 h. The reaction mixture was diluted with DCM (150 mL), washed with brine (200 mL), dried over anhydrous Na$_2$SO$_4$ and concentrated to give a crude, which was purified by silica gel column chromatography (PE: EA=30:1 to 3:1) to give 7 as a yellow solid (620 mg, 89% yield). $^1$H NMR (400 MHz, DMSO-d$_6$): δ 8.04 (d, J=2.0 Hz, 1H), 7.78-7.70 (m, 5H), 7.52-7.42 (m, 4H), 7.17 (d, J=8.8 Hz, 1H), 4.10 (t, J=4.0 Hz, 2H), 3.91 (s, 3H), 3.55 (t, J=4.4 Hz, 2H), 3.49 (t, J=6.0 Hz, 2H), 3.01 (t, J=6.0 Hz, 2H), 2.70 (s, 3H), 2.39 (s, 3H), 2.33 (s, 3H). MS (ESI) m/z 630.8, 632.8 [M+H]$^+$.

(E)-2-(3-bromo-4-methoxystyryl)-N-(2-(2-fluoroethoxy)ethyl)-N,5-dimethylbenzo[d]thiazol-6-amine (8)

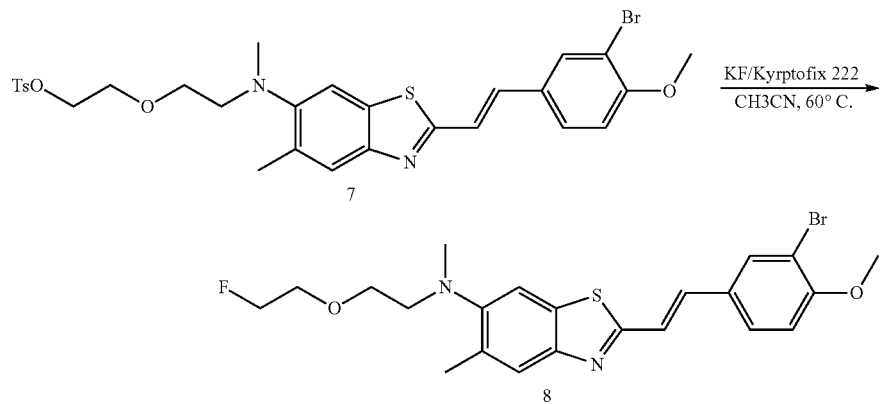

A mixture of 7 (289 mg, 0.458 mmol), KF (66 mg, 1.145 mmol) and Kryptofix© 222 (548 mg, 1.455 mmol) in dry-CH$_3$CN (43 mL) was heated at 60° C. under N$_2$ in a sealed tube for 1 h. The reaction mixture was diluted with EtOAc (100 mL), washed with brine (2×100 mL), dried over anhydrous Na$_2$SO$_4$ and concentrated to give a crude 8 (259 mg crude), which was used directly for next step without further purification. $^1$H NMR (400 MHz, DMSO-d$_6$). δ 8.04 (d, J=2.4 Hz, 1H), 7.79-7.73 (m, 3H), 7.50 (s, 2H), 7.17 (d, J=8.8 Hz, 1H), 4.57-4.22 (m, 2H), 3.90 (s, 3H), 3.11 (t, J=6.0 Hz, 2H), 2.76 (s, 3H), 2.37 (s, 3H). MS (ESI) m/z 479.0, 481.0 [M+H]$^+$.

(E)-2-bromo-4-(2-(6-((2-(2-fluoroethoxy)ethyl)(methyl)amino)-5-methylbenzo[d]thiazol-2-yl)vinyl)phenol (9)

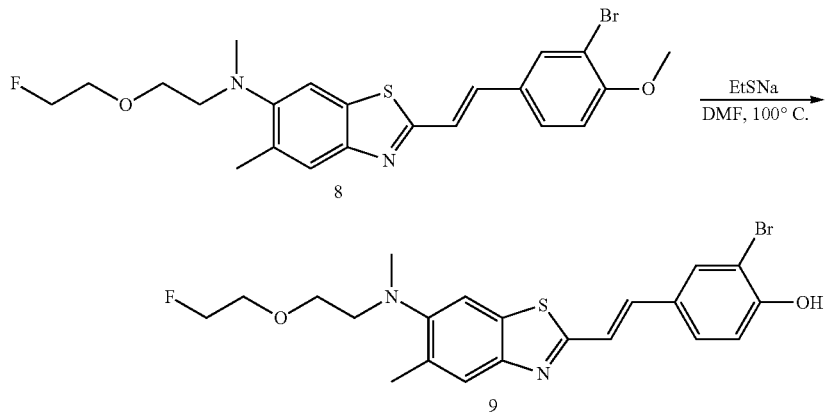

A mixture of crude 8 (259 mg crude) and EtSNa (115 mg, 1.37 mmol) in dry-DMF (7 mL) was heated at 100° C. under N₂ for 0.5 h. The reaction mixture was purified by Prep-HPLC (10-80% CH₃CN in H₂P) to give 9 as a yellow solid (140 mg, 66% for 2 steps). ¹H NMR (400 MHz, DMSO-d₆). δ 7.93 (d, J=2.0 Hz, 1H), 7.73 (d, J=8.4 Hz, 2H), 7.61 (d, J=8.8, 2.4 Hz, 1H), 7.42 (d, J=7.6 Hz, 2H), 6.98 (d, J=8.4 Hz, 1H), 4.55 (dd, J=8.0, 4.0 Hz, 1H), 4.43 (dd, J=8.0, 4.0 Hz, 1H), 3.68-3.57 (m, 4H), 3.11-3.08 (m, 2H), 2.75 (s, 3H), 2.36 (s, 3H). MS (ESI) m/z 465.0, 467.0 [M+H]+

(E)-2-bromo-4-(2-(6-((2-(2-hydroyethoxy)ethyl)(methyl)amino)-5-methylbenzo[d]thiazol-2-yl)vinyl)phenol (10)

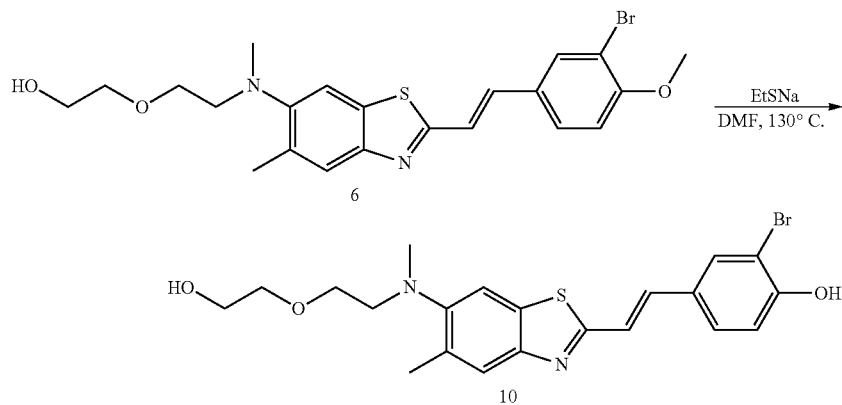

A mixture of 6 (1.2 g, 2.51 mmol) and EtSNa (1.06 g, 12.6 mmol) in dry-DMF (26.5 mL) was heated at 130° C. under N₂ for 5 h. The reaction mixture was purified by Prep-HPLC (10-80% CH₃CN in H₂O) to give 10 as a yellow solid (700 mg, 63% yield). MS (ESI) m/z 462.9, 464.9 [M+H]+.

(E)-2-bromo-4-(2-(6-((2-(2-hydroxyethoxy)ethyl)(methyl)amino)-5-methylbenzo[d]thiazol-2-yl)vinyl)phenyl dimethylcarbamate (11)

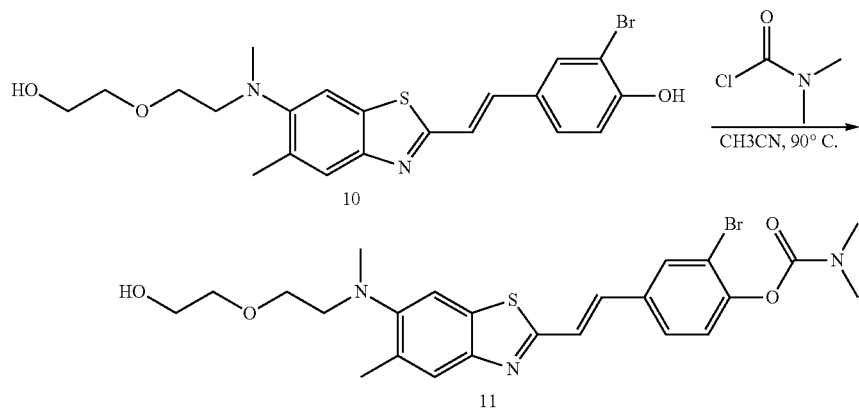

A mixture of 7 (700 mg, 1.51 mmol), dimethylcarbamoyl chloride (170 mg, 1.59 mmol) and K2CO3 (250 mg, 1.81 mmol) in CH3CN (21 mL) was stirred at 90° C. for 3 h. The reaction mixture was diluted with EtOAc (40 mL), washed with brine (20 mL), dried over anhydrous Na2SO4 and concentrated to give a crude, which was purified by Prep-HPLC (10-80% CH3CN in H2O) to give 11 as a yellow solid (720 mg, 89% yield). MS (ESI) m/z 534.1 and 536.1 [M+H]⁺.

(E)-2-(2-((2-(3-bromo-4-((dimethylcarbamoyl)oxy)
styryl)-5-methylbenzo[d]thiazol-6-yl)(methyl)
amino)ethoxy)ethyl 4-methylbenzenesulfonate (12)

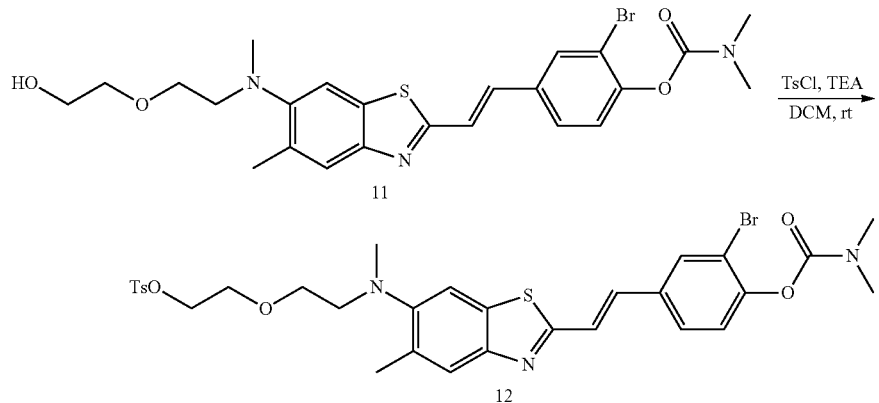

To a mixture of 11 (708 mg, 1.33 mmol) and TEA (671 mg, 6.64 mmol) in dry-DCM (14 mL) was added TsCl (757 mg, 3.98 mmol) at 0° C. The reaction mixture was stirred at rt for 6.5 h. The reaction mixture was diluted with DCM (50 mL), washed with brine (80 mL), dried over anhydrous Na2SO4 and concentrated to give a crude, which was purified by silica gel column chromatography (PE: EA=20:1 to 2:1) to give 12 as a yellow solid (520 mg, 57% yield). MS (ESI) m/z 688.1 and 690.0 [M+H]$^+$.

(E)-2-bromo-4-(2-(6-((2-(2-fluoroethoxy)ethyl)
(methyl)amino)-5-methylbenzo[d]thiazol-2-yl)vinyl)
phenyl dimethylcarbamate (13)

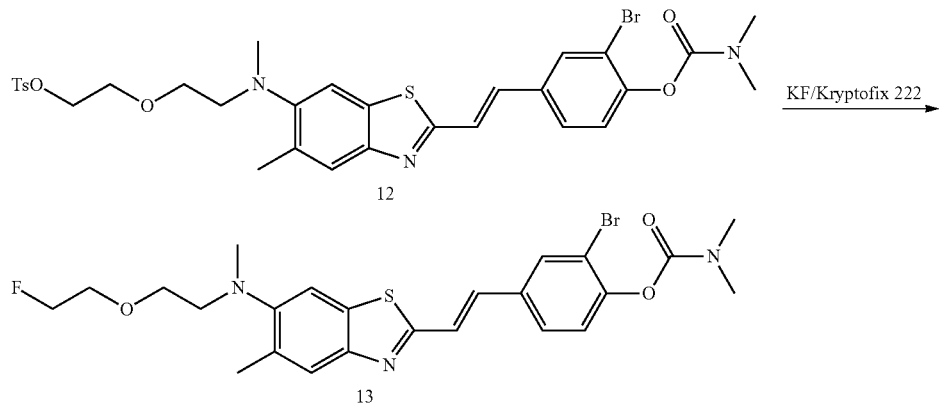

A mixture of 12 (94.0 mg, 0.137 mmol), KF (19.9 mg, 0.343 mmol) and Kryptofix® 222 (154.9 mg, 0.412 mmol) in dry-CH$_3$CN (14 mL) was heated at 60° C. under N$_2$ in a sealed tube for 2 h. The reaction mixture was diluted with EtOAc (40 mL), washed with brine (2×40 mL), dried over anhydrous Na$_2$SO$_4$ and concentrated to give a crude product, which was purified by Prep-TLC (DCM: MeOH=20:1) to give 13 as a yellow solid (15 mg, 20% yield). $^1$H NMR (400 MHz, DMSO-d$_6$): δ 8.12 (d, J=2.4 Hz, 1H), 7.85-7.76 (m, 3H), 7.64-7.52 (m, 2H), 7.32 (d, J=8.0 Hz, 1H), 4.57-4.42 (m, 2H), 3.68-3.58 (m, 4H), 3.20-3.08 (m, 5H), 2.94 (s, 3H), 2.77 (s, 3H), 2.38 (s, 3H). MS (ESI) m/z 536.1 and 538.1 [M+H]$^+$.

Screening Using In Vitro Binding Assay with Pre-Formed Fibrils (PFFs) of Alpha-Synuclein and Counter-Screening with Tau and Aβ PFFs.

Figure 2B:
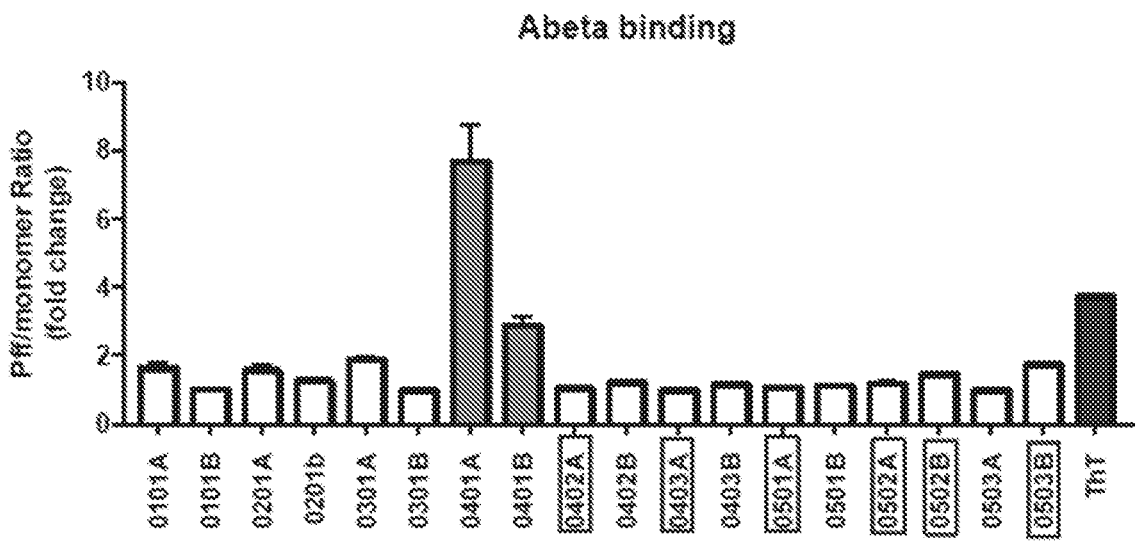
FIG. 2B shows binding data or compounds disclosed herein for AD.
Figure 2C:
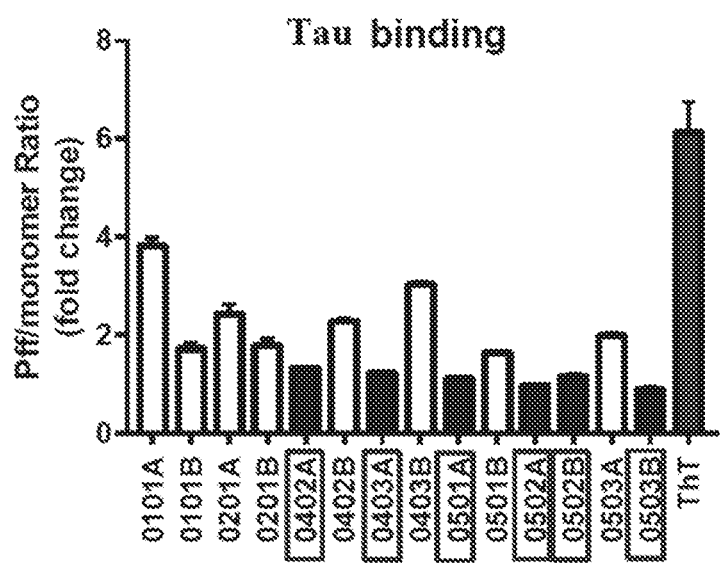
FIG. 2C shows binding data or compounds disclosed herein for Tau.
Figure 3:
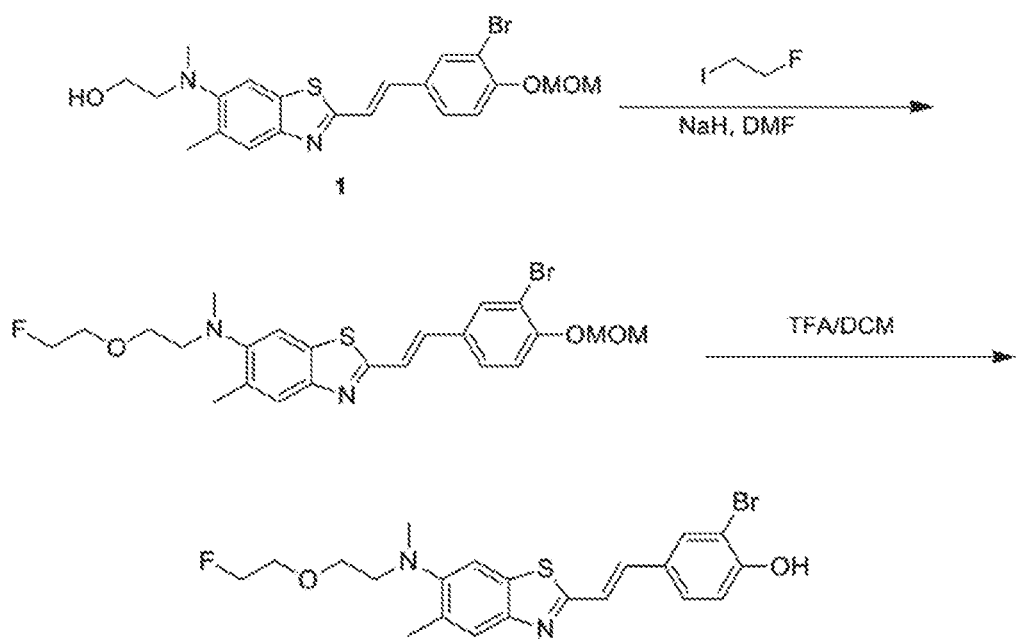
FIG. 3 illustrates the synthesis of compounds disclosed herein.

To perform in vitro binding assay, compounds were screened. The senile plaque PET tracer, PiB and ThT are listed with positive compounds (z644, z257) with relative higher selectivity and affinity to alpha-Syn fibrils and one negative compound (z819) are listed (FIG. 1A). The summary of the binding selectivity between z644, z257, positive control ThT with various PFFs are depicted in FIG. 1B. It appears that both z644 and z257 displayed stronger binding affinity toward alpha-Syn PFF than Aβ or Tau PFFs, whereas ThT non-selectively interacted with both α-Syn and Tau PFFs (FIG. 1). Compound z644 and z257 possess significantly higher binding activities toward α-Syn than ThT, whereas z-819 barely interacted with α-Syn PFFs. On the other hand, both z644 and z257 revealed substantially weaker binding affinity toward Aβ or Tau PFFs (FIG. 1C & D). An amino group and a methyl group in the benzothazole were added to increase its brain permeability and fluorescent signals. (FIG. 1E and FIG. 1F). The synthesized derivatives were subsequently subjected to the α-Syn PFFs binding and counter-screen of Tau and Aβ PFFs as described above. Only the compounds that displayed prominent α-Syn PFFs binding affinity but modestly associated with Aβ or Tau PFFs are highlighted in the boxes (FIGS. 2A, 2B, and 2C).

Candidate Compounds on the Cellular α-Syn, Tau and Aβ Aggregation Model for the Binding Selectivity.

Primary cultured neurons were infected with AAV-α-Syn, AAV-Tau FL or AAV-APP fragment virus for 7 days, and then treated with α-Syn, Tau or Aβ PFFs by following the described protocols (Volpicelli-Daley et al., 2014). In a few days, the positive compounds were added in the primary neurons with indicated aggregation. Desirable compounds selectively yielded the positive signals in α-Syn aggregated neurons but negative effects in neurons with Aβ or Tau aggregations. Of these tested compounds, EU-004-03A, EU-005-02A and EU-005-02B were identified with positive for selective binding.

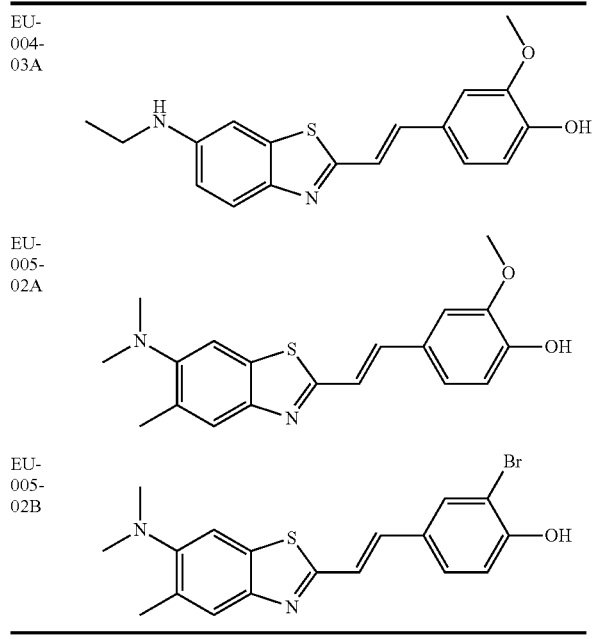

Compounds with the Brain Slides with Lewy Bodies

To further explore whether the positive compounds selectively bind to the Lewy bodies, a α-Syn A53T patient-derived mutant virus was injected into WT mice brain slices. These mice display extensive Lewy bodies in the Substantial nigra (SN). Moreover, P301S mice expressed neurofibrillary tangles (NFT). The Lewy bodies were labeled with p-α-Syn S129 antibody and the positive aggregates were also labeled with the fluorescent signals from the small molecules. As positive control, ThT co-localized with p-S129 aggregates in the brain sections, but compounds EU-004-02A and EU-005-02A signals were very weak. Remarkably, other compounds revealed strong binding activities. However, it was worth noting that almost none of the tested compounds were reactive with NFT.

The ex vivo screening was extended into human DLB, MSA and AD patient samples. Neurodegenerative disease of DLB (dementia with Lewy Bodies) and MSA belongs to synucleinopathies with well-defined Lewy bodies. Again, the positive compounds showed robust signals with LBs and LNs, and noticeably, EU-004-03A, EU-005-02A and EU-005-02B. On AD patients slides, these compounds barely co-stained with anti-AD or AT8 positive aggregate signals, whereas they co-stained with p-S129 Lewy bodies in AD brain sections. Hence, these compounds selectively interact with α-Syn aggregates versus Aβ or Tau inclusions.

Alpha-Syn PFFs and Compounds the Direct Interaction Using Fluorescence Spectroscopy to Test Compounds Emission Intensity Binding with Different Concentrations of α-Syn, Aβ and Tau PFFs To further investigate the selected compounds binding activities with α-Syn PFFs, fluorescence spectroscopy titrations were conducted to quantitatively measure compounds emission intensity when interacting with different concentrations of α-Syn PFFs. The UV spectrum of each compound was determined and selected for the optimal wavelength to conduct the fluorescence spectroscopic studies. EU-004-02B displayed the modest and weak binding activities toward these 3 PFFs. Interestingly, EU-005-02A strongly bound to both α-Syn and Tau PFFs. Remarkably, EU-005-02B revealed stronger binding affinity toward α-Syn PFFs versus Tau and Aβ PFFs. EU-005-02B showed the dose-dependent escalation of the emission intensities. The calculated binding constants Kd for α-Syn, Aβ and Tau PFFs were: 0.17, 0.85 and 3.7 μM, respectively. The fluorescent spectrophotometry analysis indicates that EU-005-02B is more prone to associate with α-Syn aggregates versus Aβ or Tau PFFs as compared to ThT.

In Vivo Brain/Plasma Ratio and its Brain Penetration.

To test whether these compounds are brain permeable in vivo, in vivo PK profiling was conducted to determine brain exposure. EU-005-02B displayed a long in vivo half-life with time-dependent escalation of B/P ratios, indicating that its brain permeability is much higher as compared to EU-005-02A that decayed 2 h after i.v. administration (5 mg/kg) (Table 2).

TABLE 2

| In vivo PK and brain permeability analysis of EU05-02A and EU05-02B BP Ratio of EU-005-02A in Male ICR Mouse After 5 mg/kgIV Dosed | | | | |
|---|---|---|---|---|
| Time point (Hours) | Animal Study No. | B/P | Mean | SD |
| 0.50 | 204 | 0.65 | 0.99 | 0.55 |
|  | 205 | 1.62 |  |  |
|  | 206 | 0.69 |  |  |
| 1.00 | 207 | 0.52 | 0.41 | 0.14 |
|  | 208 | 0.46 |  |  |
|  | 209 | 0.26 |  |  |
| 2.00 | 210 | 0.42 | 0.41 | 0.07 |
|  | 211 | 0.49 |  |  |
|  | 212 | 0.34 |  |  |
| 4.00 | 213 | NA | NA | NA |
|  | 214 | NA |  |  |
|  | 215 | NA |  |  |
| 8.00 | 216 | NA | NA | NA |
|  | 217 | NA |  |  |
|  | 218 | NA |  |  |

| BP Ratio of EU-005-02B in Male ICH Mouse After 5 mg/kgIV Dosed | | | | |
|---|---|---|---|---|
| Time point (Hours) | Animal Study No. | B/P | Mean | SD |
| 0.50 | 304 | 2.00 | 1.88 | 0.66 |
|  | 305 | 2.47 |  |  |
|  | 306 | 1.16 |  |  |
| 1.00 | 307 | 2.72 | 4.44 | 1.70 |
|  | 308 | 6.12 |  |  |
|  | 309 | 4.48 |  |  |

-continued

| BP Ratio of EU-005-02B in Male ICH Mouse After 5 mg/kgIV Dosed | | | | |
|---|---|---|---|---|
| Time point (Hours) | Animal Study No. | B/P | Mean | SD |
| 2.00 | 310 | 5.13 | 14.69 | 9.99 |
| | 311 | 13.88 | | |
| | 312 | 25.06 | | |
| 4.00 | 313 | 29.74 | 18.81 | 12.21 |
| | 314 | 5.63 | | |
| | 315 | 21.06 | | |
| 8.00 | 316 | 57.33 | 57.11 | 21.00 |
| | 317 | 78.00 | | |
| | 318 | 36.00 | | |

The invention claimed is:

1. A compound (E)-2-bromo-4-(2-(6-((2-(2-fluoroethoxy)ethyl)(methyl)amino)-5-methylbenzo[d]thiazol-2-yl)vinyl)phenol, or a salt or solvate thereof, wherein fluoro is $^{18}$F.

2. A compound (E)-2-bromo-4-(2-(6-((2-(2-fluoroethoxy)ethyl)(methyl)amino)-5-methylbenzo[d]thiazol-2-yl)vinyl)phenyl dimethylcarbamate, or a salt or solvate thereof, wherein fluoro is $^{18}$F.

3. A method of detecting pre-formed fibrils (PFFs) of alpha-Synuclein in the brain comprising:
  a) administering a compound to a subject, wherein the compound is a compound of Formula I

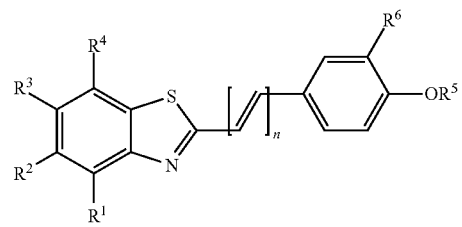

Formula I or a salt or solvate thereof, wherein:
n is 1:
R$^1$, R$^2$, R$^4$, and R$^{12-14}$ are each independently hydrogen, or an R group selected from the group consisting of C$_{1-6}$ alkyl, C$_{2-6}$ alkenyl, C$_{2-6}$ alkynyl, C$_{1-6}$ alkoxy, C$_{4-6}$cycloalkyl, hydroxyl, C$_{1-6}$ hydroxyalkyl, C$_{2-6}$ hydroxyalkenyl, C$_{2-6}$ hydroxyalkynyl, thiol, C$_{1-6}$ thioalkyl, C$_{2-6}$ thioalkenyl, C$_{2-6}$ thioalkynyl, C$_{1-6}$ thioalkoxy, carboxyl, C$_{1-6}$ carboxyalkyl, halo, C$_{1-6}$ haloalkyl, C$_{2-6}$ haloalkenyl, C$_{2-6}$ haloalkynyl, C$_{1-6}$ haloalkoxy, amino, C$_{1-6}$ aminoalkyl, C$_{2-6}$ aminoalkenyl, C$_{2-6}$ aminoalkynyl C$_{1-6}$ aminoalkoxy, cyano, C$_{1-6}$ cyanoalkyl, C$_{2-6}$ cyanoalkenyl, C$_{2-6}$ cyanoalkynyl, C$_{1-6}$ cyanoalkoxy, nitro, C$_{1-6}$ nitroalkyl, C$_{2-6}$ nitroalkenyl, C$_{2-6}$ nitroalkynyl, C$_{1-6}$ nitroalkoxy, and —OCH$_2$OR', wherein R' is H or C$_{1-6}$ alkyl;
R is an amino group —NR$^9$R$^{10}$, wherein R$^9$ and R$^{10}$ are independently hydrogen or an R group selected from the group consisting of C$_{1-6}$ alkyl, C$_{2-6}$ alkenyl, C$_{2-6}$ alkynyl, C$_{1-6}$ alkoxy, C$_{4-6}$ cycloalkyl, hydroxyl, C$_{1-6}$, hydroxyalkyl, C$_{2-6}$ hydroxyalkenyl, C$_{2-6}$ hydroxyalkynyl, thiol, C$_{1-6}$ thioalkyl, C$_{2-6}$ thioalkenyl, C$_{2-6}$ thioalkynyl, C$_{1-6}$ thioalkoxy, carboxyl, C$_{1-6}$ carboxyalkyl, halo, C$_{1-6}$ haloalkyl, C$_{2-6}$ haloalkenyl, C$_{2-6}$ haloalkynyl, C$_{1-6}$ haloalkoxy, amino, C$_{1-6}$ aminoalkyl, C$_{2-6}$ aminoalkenyl, C$_{2-6}$ aminoalkynyl, C$_{1-6}$ aminoalkoxy, cyano, C$_{1-6}$ cyanoalkyl, C$_{2-6}$ cyanoalkenyl, C$_{2-6}$ cyanoalkynyl, C$_{1-6}$ cyanoalkoxy, nitro, C$_{1-6}$ nitroalkyl C$_{2-6}$ nitroalkenyl, C$_{2-6}$ nitroalkynyl, C$_{1-6}$ nitroalkoxy, and —OCH$_2$OR', wherein R' is H or C$_{1-6}$alkyl;
R$^5$ is hydrogen; and
R$^6$ is halogen,
wherein at least one of R$^{1-6}$ comprises an in vivo imaging moiety; and
wherein when R$^3$ comprises the in vivo imaging moiety, the in vivo imaging moiety is at R$^9$;
  b) scanning the brain of the subject for the in vivo imaging moiety;
  c) locating the in vivo imaging moiety in the brain of the subject; and
  d) creating an image of the subject indicating the location of the in vivo imaging moiety indicating the presence of pre-formed fibrils (PFFs) of alpha-Synuclein.

4. A method of diagnosing a subject with or at risk of developing Parkinson's disease comprising:
  a) administering a compound to a subject, wherein the compound is a compound of Formula I

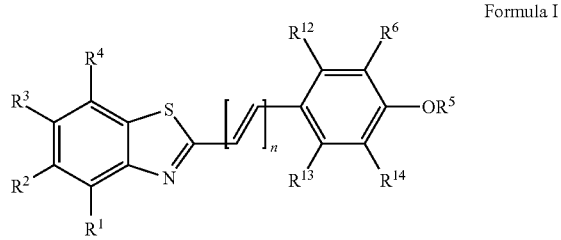

Formula I or a salt or solvate thereof, wherein:
n is 1:
R$^1$, R$^2$, R$^4$, and R$^{12-14}$ are each independently hydrogen, or an R group selected from the group consisting of C$_{1-6}$ alkyl, C$_{2-6}$ alkenyl, C$_{2-6}$ alkynyl, C$_{1-6}$ alkoxy, C$_{4-6}$ cycloalkyl, hydroxyl, C$_{1-6}$ hydroxyalkyl, C$_{2-6}$ hydroxyalkenyl, C$_{2-6}$ hydroxyalkynyl, thiol, C$_{1-6}$ thioalkyl, C$_{2-6}$ thioalkenyl C$_{2-6}$ thioalkynyl, C$_{1-6}$ thioalkoxy, carboxyl, C$_{1-6}$ carboxyalkyl, halo, C$_{1-6}$ haloalkyl, C$_{2-6}$ haloalkenyl, C$_{2-6}$ haloalkynyl, C$_{1-6}$ haloalkoxy, amino, C$_{1-6}$ aminoalkyl, C$_{2-6}$ aminoalkenyl, C$_{2-6}$ aminoalkynyl, C$_{1-6}$ aminoalkoxy, cyano, C$_{1-6}$ cyanoalkyl, C$_{2-6}$ cyanoalkenyl, C$_{2-6}$ cyanoalkynyl, C$_{1-6}$ cyanoalkoxy, nitro, C$_{1-6}$ nitroalkyl, C$_{2-6}$ nitroalkenyl, C$_{2-6}$ nitroalkynyl, C$_{1-6}$ nitroalkoxy, and —OCH$_2$OR', wherein R' is H or C$_{1-6}$ alkyl;
R$^3$ is an amino group —NR$^9$R$^{10}$, wherein R$^9$ and R$^{10}$ are independently hydrogen or an R group selected from the group consisting of C$_{1-6}$ alkyl, C$_{2-6}$ alkenyl, C$_{2-6}$ alkynyl, C$_{1-6}$ alkoxy, C$_{4-6}$ cycloalkyl, hydroxyl, C$_{1-6}$ hydroxyalkyl, C$_{2-6}$ hydroxyalkenyl, C$_{2-6}$ hydroxyalkynyl, thiol, C$_{1-6}$ thioalkyl, C$_{2-6}$ thioalkenyl, C$_{2-6}$ thioalkynyl, C$_{1-6}$ thioalkoxy, carboxyl, C$_{1-6}$ carboxyalkyl, halo, C$_{1-6}$ haloalkyl, C$_{2-6}$ haloalkenyl, C$_{2-6}$ haloalkynyl, C$_{1-6}$ haloalkoxy, amino, C$_{1-6}$ aminoalkyl, C$_{2-6}$ aminoalkenyl, C$_{2-6}$ aminoalkynyl, C$_{1-6}$ aminoalkoxy, cyano, C$_{1-6}$ cyanoalkyl, C$_{2-6}$ cyanoalkenyl, C$_{2-6}$ cyanoalkynyl, C$_{1-6}$ cyanoalkoxy, nitro, C$_{1-6}$ nitroalkyl, C$_{2-6}$ nitroalkenyl, C$_{2-6}$ nitroalkynyl, C$_{1-6}$ nitroalkoxy, and —OCH$_2$OR', wherein R' is H or C$_{1-6}$ alkyl;
R$^5$ is hydrogen; and
R$^6$ is halogen, wherein at least one of $R^{1-6}$ comprises an in vivo imaging moiety; and wherein when $R^3$ comprises the in vivo imaging moiety, the in vivo imaging moiety is at $R^9$;

b) scanning the brain of the subject for the in vivo imaging moiety;

c) locating the in vivo imaging moiety in the brain of the subject;

d) creating an image of the subject indicating the location of the in vivo imaging moiety indicating the presence of pre-formed fibrils (PFFs) of alpha-Synuclein; and e) diagnosing the subject with or at risk of developing Parkinson's disease.

5. A method of detecting pre-formed fibrils (PFFs) of alpha-Synuclein in the brain comprising:

a) administering a compound to a subject, wherein the compound is a compound of Formula III:

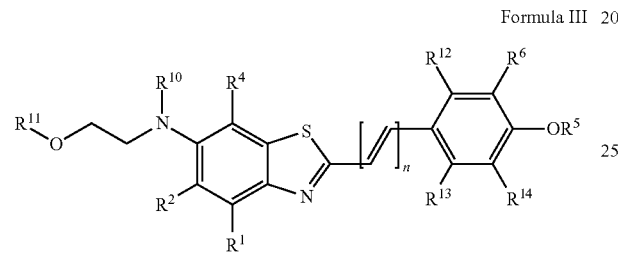

Formula III or a salt or solvate thereof, wherein:

n is 1;

$R^1$, $R^4$ and $R^{12-14}$ are each independently hydrogen, or an R group selected from the group consisting of $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, $C_{1-6}$ cyanoalkoxy, nitro, $C_{1-6}$ nitroalkyl, $C_{2-6}$ nitroalkenyl, $C_{2-6}$ nitroalkynyl, $C_{1-6}$ nitroalkoxy, and —$OCH_2OR'$, wherein R' is H or $C_{1-6}$ alkyl;

$R^2$ is hydrogen or $C_{1-6}$ alkyl;

$R^5$ is hydrogen or hydroxyl protecting group wherein the hydroxyl protecting group is selected from the group consisting of allyl, benzyl, methoxymethyl, ethoxyethyl, methyl thiomethyl, benzyloxymethyl, t-butyl, trityl, methoxytrityl, tetrahydropyranyl, 2-napthylmethyl, p-methoxybenzyl, o-nitrobenzyl, 9-Phenylxanthylphenyixanthyl, trimethylsilyl, triethylsilyl, triisopropylsilyl, t-butyldimethylsilyl, t-butyldiphenylsilyl, phenyldimethylsilyl, formyl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl, 4-bromobenzoyl, 4-nitrobenzoyl, benzenesulfonyl, and p-toluenesulfonyl;

$R^6$ is halogen;

$R^{10}$ is hydrogen or $C_{1-6}$ alkyl, and $R^{11}$ is $C_{1-6}$ alkyl, $C_{1-6}$ haloalkyl, or $C_{1-6}$ aminoalkyl, wherein $R^{11}$ comprises an in vivo imaging moiety;

b) scanning the brain of the subject for the vivo imaging moiety;

c) locating the in vivo imaging moiety in the brain of the subject; and d) creating an image of the subject indicating the location of the in vivo imaging moiety indicating the presence of pre-formed fibrils (PFFs) of alpha-Synuclein.

6. A method of diagnosing a subject with or at risk of developing Parkinson's disease comprising:

a) administering a compound to a subject, wherein the compound is a compound of Formula III:

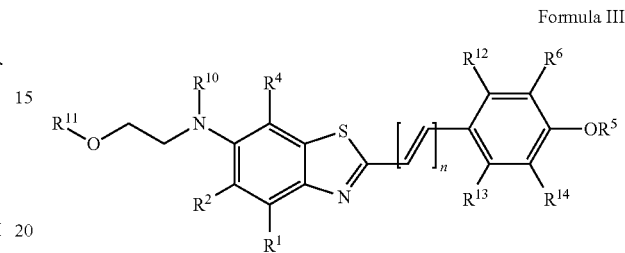

Formula III or a salt or solvate thereof, wherein:

n is 1;

$R^1$, $R^4$ and $R^{12-14}$ are each independently hydrogen, or an R group selected from the group consisting of $C_{1-6}$ alkyl, $C_{2-6}$ alkenyl $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ amidoalkynyl, $C_{1-6}$ aminoalkoxy, cyano, $C_{1-6}$ cyanoalkyl, $C_{2-6}$ cyanoalkenyl, $C_{2-6}$ cyanoalkynyl, $C_{1-6}$ cyanoalkoxy, nitro, $C_{1-6}$ nitroalkyl, $C_{2-6}$ nitroalkenyl, $C_{2-6}$ nitroalkynyl, $C_{1-6}$ nitroalkoxy, and $OCH_2OR'$, wherein R' is H or $C_{1-6}$ alkyl;

$R^2$ is hydrogen or $C_{1-6}$ alkyl;

$R^5$ is hydrogen or hydroxyl protecting group wherein the hydroxyl protecting group is selected from the group consisting of allyl, benzyl, methoxymethyl, ethoxyethyl, methyl thiomethyl, benzyloxymethyl, t-buty trityl, methoxytrityl, tetrahydropyranyl, 2-napthylmethyl, p-methoxybenzyl, o-nitrobenzyl, 9-Phenylxanthylphenylxanthyl, trimethylsilyl, triethylsilyl, trisopropylsilyl, t-butyldimethylsilyl, t-butyidiphenylsilyl, phenyldimiethylsily, formryl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl 4-bromobenzoyl, 4-nitrobenzoyl, benzenesulfonyl, and p-toluenesulfonyl;

$R^6$ is halogen;

$R^{10}$ is hydrogen or $C_{1-6}$ alkyl, and $R^{11}$ is $C_{1-6}$ alkyl, $C_{1-6}$ haloalkyl, or $C_{1-6}$ aminoalkyl, wherein $R^{11}$ comprises an in vivo imaging moiety;

b) scanning the brain of the subject for the in vivo imaging moiety;

c) locating the in vivo imaging moiety in the brain of the subject;

d) creating an image of the subject indicating the location of the in vivo imaging moiety indicating the presence of pre-formed fibrils (PFFs) of alpha-Synuclein; and e) diagnosing the subject with or at risk of developing Parkinson's disease.

7. A method of detecting pre-formed fibrils (PFFs) of alpha-Synuclein in the brain comprising:

a) administering a compound to a subject, wherein the compound is a compound of Formula V:

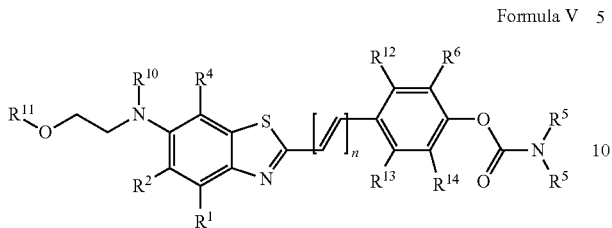

Formula V or a salt or solvate thereof, wherein:
  n is 1:
  $R_1$, $R^4$ and $R^{12-14}$ are each independently hydrogen, or an R group selected from the group consisting of $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, $C_{1-6}$ cyanoalkoxy, nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl;
  $R^2$ is hydrogen or $C_{1-6}$ alkyl;
  $R^5$ is, individually and independently at each occurrence, hydrogen, $C_{1-6}$ alkyl, $C_{2-6}$ alkenyl, or $C_{2-6}$ alkynyl;
  $R^6$ is halogen;
  $R^{10}$ is hydrogen or $C_{1-6}$ alkyl or an R group of formula V, and
  $R^{11}$ is $C_{1-6}$ haloalkyl, or $C_{1-6}$ aminoalkyl, wherein $R^{11}$ comprises an in vivo imaging moiety;
b) scanning the brain of the subject for the in vivo imaging moiety;
c) locating the in vivo imaging moiety in the brain of the subject; and
d) creating an image of the subject indicating the location of the in vivo imaging moiety indicating the presence of pre-formed fibrils (PFFs) of alpha-Synuclein.

8. A method of diagnosing a subject with or at risk of developing Parkinson's disease comprising:

a) administering a compound to a subject, wherein the compound is a compound of Formula V:

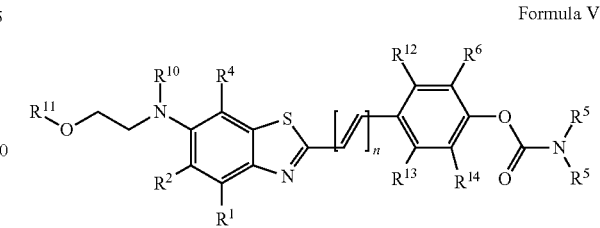

Formula V or a salt or solvate thereof, wherein:
  n is 1;
  $R_1$, $R^4$ and $R^{12-14}$ are each independently hydrogen, or an R group selected from the group consisting of $C_{1-6}$ alkyl, $C_{2-6}$ alkenyl, $C_{2-6}$ alkynyl, $C_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, carboxyl, $C_{1-6}$ carboxyalkyl, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, $C_{1-6}$ cyanoalkoxy, nitro, $C_{1-6}$ nitroalkyl, $C_{2-6}$ nitroalkenyl, $C_{2-6}$ nitroalkynyl, $C_{1-6}$ nitroalkoxy, and —OCH$_2$OR', wherein R' is H or $C_{1-6}$ alkyl;
  $R^2$ is hydrogen or $C_{1-6}$ alkyl;
  $R^5$ is individually and independently at each occurrence, hydrogen, $C_{1-6}$ alkyl, $C_{2-6}$ alkenyl, or $C_{1-6}$ alkynyl; and
  $R^6$ is halogen;
  $R^{10}$ is hydrogen or $C_{1-6}$ alkyl or an R group of formula V, and
  $R^{11}$ is $C_{1-6}$ alkyl, $C_{1-6}$ haloalkyl, or $C_{1-6}$ aminoalkyl, wherein $R^{11}$ comprises an in vivo imaging moiety;
b) scanning the brain of the subject for the in vivo imaging moiety;
c) locating the in vivo imaging moiety in the brain of the subject;
d) creating an image of the subject indicating the location of the in vivo imaging moiety indicating the presence of pre-formed fibrils (PFFs) of alpha-Synuclein; and
e) diagnosing the subject with or at risk of developing Parkinson's disease.

\* \* \* \* \*